US008486457B2

(12) United States Patent
Tripp et al.

(10) Patent No.: US 8,486,457 B2
(45) Date of Patent: *Jul. 16, 2013

(54) COMPOSITIONS THAT TREAT OR INHIBIT PATHOLOGICAL CONDITIONS ASSOCIATED WITH INFLAMMATORY RESPONSE

(75) Inventors: Matthew L. Tripp, Gig Harbor, WA (US); John G. Babish, Brooktondale, NY (US); Jeffrey S. Bland, Fox Island, WA (US); Gary Darland, Gig Harbor, WA (US); Robert Lerman, Gig Harbor, WA (US); Daniel O. Lukaczer, Gig Harbor, WA (US); DeAnn J. Liska, Tacoma, WA (US); Terrence Howell, Lansing, NY (US)

(73) Assignee: Metaproteomics, LLC., San Clemente, CA (US)

( * ) Notice: Subject to any disclaimer, the term of this patent is extended or adjusted under 35 U.S.C. 154(b) by 1249 days.

This patent is subject to a terminal disclaimer.

(21) Appl. No.: 10/532,388

(22) PCT Filed: Oct. 20, 2003

(86) PCT No.: PCT/US03/33362
§ 371 (c)(1),
(2), (4) Date: Mar. 21, 2007

(87) PCT Pub. No.: WO2004/037180
PCT Pub. Date: May 6, 2004

(65) Prior Publication Data
US 2007/0160692 A1  Jul. 12, 2007

Related U.S. Application Data

(60) Provisional application No. 60/420,383, filed on Oct. 21, 2002, provisional application No. 60/450,237, filed on Feb. 25, 2003.

(51) Int. Cl.
*A01N 65/00* (2009.01)
(52) U.S. Cl.
USPC ........................................................ 424/725
(58) Field of Classification Search
USPC ........................................................ 424/725
See application file for complete search history.

(56) References Cited

U.S. PATENT DOCUMENTS

| | | |
|---|---|---|
| 3,451,821 A | 6/1969 | Todd et al. |
| 3,552,975 A | 1/1971 | Worden |
| 3,720,517 A | 3/1973 | Bavisotto et al. |
| 3,932,603 A | 1/1976 | Haas |
| 3,933,919 A | 1/1976 | Wilkinson |
| 3,965,188 A | 6/1976 | Westermann et al. |
| 4,123,561 A | 10/1978 | Grant |
| 4,133,903 A | 1/1979 | Thiele et al. |
| 4,148,873 A | 4/1979 | Owades |
| 4,154,865 A | 5/1979 | Grant |
| 4,170,638 A | 10/1979 | Owades |
| 4,389,421 A | 6/1983 | Palamand |
| 4,401,684 A | 8/1983 | Versluys |
| 4,473,551 A | 9/1984 | Schinitsky |
| 4,554,170 A | 11/1985 | Panzner et al. |
| 4,644,084 A | 2/1987 | Cowles et al. |
| 4,692,280 A | 9/1987 | Spinelli |
| 4,758,445 A | 7/1988 | Klusters |
| 4,767,640 A | 8/1988 | Goldstein et al. |
| 4,857,554 A | 8/1989 | Kallimanis |
| 5,006,337 A | 4/1991 | Motitschke et al. |
| 5,013,571 A | 5/1991 | Hay |
| 5,041,300 A | 8/1991 | Todd et al. |
| 5,073,396 A | 12/1991 | Todd, Jr. |
| 5,082,975 A | 1/1992 | Todd, Jr. et al. |
| 5,155,276 A | 10/1992 | Paul |
| 5,166,449 A | 11/1992 | Todd, Jr. et al. |
| 5,264,236 A | 11/1993 | Ogasahara et al. |
| 5,286,506 A | 2/1994 | Millis et al. |
| 5,296,637 A | 3/1994 | Stegink et al. |
| 5,370,863 A | 12/1994 | Barney et al. |
| 5,387,425 A | 2/1995 | Hsu et al. |
| 5,604,263 A | 2/1997 | Tobe et al. |
| 5,641,517 A | 6/1997 | Eskeland et al. |
| 5,827,895 A | 10/1998 | Nutter et al. |
| 5,866,162 A | 2/1999 | Grattan |

(Continued)

FOREIGN PATENT DOCUMENTS

| | | |
|---|---|---|
| CN | 1203268 | 12/1998 |
| DE | 1901277 | 8/1970 |

(Continued)

OTHER PUBLICATIONS http://www.hopunion.com/education/componentsofhops.html 2005, 3pages.*
Abel-salam et al., Pharmacological Research, England 47(4), pp. 311-340 (Apr. 2003).
Albal, MV., et al., "Clinical evaluation of berberine in mycotic infections." Indian J. Ophthalmol 34:91-2 (1986).
Anto, et al., "Anti-inflammatory Activity of Natural and Synthetic Curcuminoids", Pharmacy and Pharmacology Communications, 4(2), pp. 103-106 (1998).
Baldermann et al., J. Chromatography A 1192(1):191-3 (May 23, 2008) (Epub Apr. 8, 2008); abstract only (1 page).
Bermejo, et al. Rev. Esp. Enferm. Dig. 95(9): 621-624 and 625-628 (2003).

(Continued)

*Primary Examiner* — Shirley V Gembeh
(74) *Attorney, Agent, or Firm* — McDermott Will & Emery LLP

(57) ABSTRACT

A natural formulation of compounds that would to modulate inflammation is disclosed. The formulation would also inhibit expression of COX-2, inhibit synthesis of prostaglandins selectively in target cells, and inhibit inflammatory response selectively in target cells. The compositions containing at least one fraction isolated or derived from hops. Other embodiments relate to combinations of components, including at least one fraction isolated or derived from hops, tryptanthrin and conjugates thereof, rosemary, an extract or compound derived from rosemary, a triterpene species, or a diterpene lactone or derivatives or conjugates thereof.

12 Claims, 14 Drawing Sheets

U.S. PATENT DOCUMENTS

| | | | |
|---|---|---|---|
| 5,919,813 A | 7/1999 | De Juan | |
| 5,968,539 A | 10/1999 | Beerse et al. | |
| 6,020,019 A | 2/2000 | Ting et al. | |
| 6,129,907 A | 10/2000 | Sreenivasan et al. | |
| 6,200,594 B1 | 3/2001 | Ernest et al. | |
| 6,210,701 B1 | 4/2001 | Darland et al. | |
| 6,224,871 B1 | 5/2001 | Hastings et al. | |
| 6,264,995 B1 | 7/2001 | Newmark et al. | |
| 6,291,483 B1 | 9/2001 | Upadhyay et al. | |
| 6,383,527 B1 | 5/2002 | Artman et al. | |
| 6,391,346 B1* | 5/2002 | Newmark et al. | 424/756 |
| 6,440,465 B1 | 8/2002 | Meisner | |
| 6,447,762 B1 | 9/2002 | Casado Galcerá | |
| 6,482,456 B1 | 11/2002 | Yokoo et al. | |
| 6,492,429 B1 | 12/2002 | Graus et al. | |
| 6,583,322 B1 | 6/2003 | Shahlai et al. | |
| 6,689,388 B2 | 2/2004 | Kuhrts | |
| 6,790,459 B1 | 9/2004 | Cheng et al. | |
| 6,801,860 B1 | 10/2004 | Dessen et al. | |
| 7,144,590 B2 | 12/2006 | Khurts | |
| 7,195,785 B2 | 3/2007 | Babish et al. | |
| 7,205,151 B2 | 4/2007 | Babish et al. | |
| 7,270,835 B2 | 9/2007 | Tripp et al. | |
| 7,279,185 B2 | 10/2007 | Babish et al. | |
| 7,332,185 B2 | 2/2008 | Babish et al. | |
| 7,431,948 B2 | 10/2008 | Tripp et al. | |
| 2002/0028852 A1 | 3/2002 | Ghai et al. | |
| 2002/0068098 A1* | 6/2002 | Babish et al. | 424/725 |
| 2002/0076452 A1 | 6/2002 | Babish et al. | |
| 2002/0077299 A1 | 6/2002 | Babish et al. | |
| 2002/0086062 A1 | 7/2002 | Kuhrts | |
| 2002/0086070 A1 | 7/2002 | Kuhrts | |
| 2002/0156087 A1 | 10/2002 | Nuss et al. | |
| 2003/0003212 A1 | 1/2003 | Chien et al. | |
| 2003/0008021 A1 | 1/2003 | Babish et al. | |
| 2003/0035851 A1 | 2/2003 | Chen | |
| 2003/0077313 A1 | 4/2003 | Schwartz et al. | |
| 2003/0096027 A1 | 5/2003 | Babish et al. | |
| 2003/0113393 A1 | 6/2003 | Babish et al. | |
| 2003/0133958 A1 | 7/2003 | Kuno et al. | |
| 2003/0180402 A1 | 9/2003 | Jia et al. | |
| 2003/0228369 A1 | 12/2003 | Kuhrts | |
| 2004/0072900 A1 | 4/2004 | Artman et al. | |
| 2004/0086580 A1 | 5/2004 | Tripp et al. | |
| 2004/0115290 A1 | 6/2004 | Tripp et al. | |
| 2004/0137096 A1 | 7/2004 | Kuhrts | |
| 2004/0151792 A1 | 8/2004 | Tripp et al. | |
| 2004/0219240 A1 | 11/2004 | Babish et al. | |
| 2005/0042317 A1 | 2/2005 | Babish et al. | |
| 2005/0129791 A1 | 6/2005 | Babish et al. | |
| 2005/0191375 A1 | 9/2005 | Babish et al. | |
| 2005/0192356 A1 | 9/2005 | Babish et al. | |
| 2006/0127511 A1 | 6/2006 | Tripp et al. | |
| 2006/0127512 A1 | 6/2006 | Tripp et al. | |
| 2006/0127513 A1 | 6/2006 | Tripp et al. | |
| 2006/0127514 A1 | 6/2006 | Tripp et al. | |
| 2006/0127515 A1 | 6/2006 | Tripp et al. | |
| 2006/0127516 A1 | 6/2006 | Tripp et al. | |
| 2006/0127517 A1 | 6/2006 | Tripp et al. | |
| 2006/0193933 A1 | 8/2006 | Tripp et al. | |
| 2006/0233902 A1 | 10/2006 | Yajima et al. | |
| 2007/0003646 A1 | 1/2007 | Kuhrts | |
| 2007/0020352 A1 | 1/2007 | Tripp et al. | |
| 2007/0160692 A1 | 7/2007 | Tripp et al. | |
| 2007/0166418 A1 | 7/2007 | Tripp et al. | |
| 2007/0172532 A1 | 7/2007 | Babish et al. | |
| 2007/0184133 A1 | 8/2007 | Tripp et al. | |
| 2008/0127720 A1 | 6/2008 | Pauli et al. | |
| 2008/0248131 A1 | 10/2008 | Tripp et al. | |
| 2009/0118373 A1 | 5/2009 | Tripp et al. | |

FOREIGN PATENT DOCUMENTS

| | | | |
|---|---|---|---|
| DE | 2212148 | 9/1972 | |
| DE | 3931147 | 3/1991 | |
| DE | 19841615 | 3/2000 | |
| EP | 0229022 | 7/1987 | |
| EP | 0606599 A1 | 7/1994 | |
| EP | 0681029 A2 | 11/1995 | |
| EP | 1481671 | 12/2004 | |
| EP | 1543834 | 6/2005 | |
| EP | 1 938 828 | 7/2008 | |
| GB | 2336363 | * 10/1990 | |
| GB | 2330076 | 4/1999 | |
| JP | 52145509 | 12/1977 | |
| JP | 58009084 | 2/1983 | |
| JP | 59059623 | 4/1984 | |
| JP | 363211219 | 9/1988 | |
| JP | 04202138 | 7/1992 | |
| JP | 6312924 | 11/1994 | |
| JP | 07165583 | 6/1995 | |
| JP | 07194351 | 8/1995 | |
| JP | 8073369 | 3/1996 | |
| JP | 08073369 | 3/1996 | |
| JP | 9067245 | 3/1997 | |
| JP | 09502202 | 3/1997 | |
| JP | 410025247 | 1/1998 | |
| JP | 10152428 | 6/1998 | |
| JP | 10179129 | 7/1998 | |
| JP | 11246399 | 9/1999 | |
| JP | 11513037 | 11/1999 | |
| JP | 11335231 | 12/1999 | |
| JP | 2001161338 | 6/2001 | |
| JP | 2002-12550 | 1/2002 | |
| JP | 2002-505296 | 2/2002 | |
| RU | 2045955 | 10/1995 | |
| SU | 1247011 | 7/1986 | |
| WO | WO 9507079 | 3/1995 | |
| WO | WO 97/31630 | 9/1997 | |
| WO | WO 9749405 | 12/1997 | |
| WO | WO 99/44623 | 9/1999 | |
| WO | WO 99/61038 | 12/1999 | |
| WO | WO-99/61038 | * 12/1999 | |
| WO | WO 00/68356 | 11/2000 | |
| WO | WO 00/74696 | 12/2000 | |
| WO | WO 02/02582 | 1/2002 | |
| WO | WO 02/32234 | 4/2002 | |
| WO | WO 03/000185 | 1/2003 | |
| WO | WO-03/000185 A3 | 1/2003 | |
| WO | WO 03/035007 | 5/2003 | |
| WO | WO 03/068205 | 8/2003 | |
| WO | WO-03/035007 A3 | 9/2003 | |
| WO | WO 03/075943 | 9/2003 | |
| WO | WO 03/082249 | 10/2003 | |
| WO | WO 2004/037180 | 5/2004 | |
| WO | WO 2004/062611 | 7/2004 | |
| WO | WO 2005/084230 | 9/2005 | |
| WO | WO 2006/053249 | 5/2006 | |
| WO | WO 2006/062681 | 6/2006 | |
| WO | WO 2007/067812 | 6/2007 | |
| ZA | 200000857 | 8/2001 | |

OTHER PUBLICATIONS

Bolick D et al., Endocrinology 144(12), pp. 5227-5231 (Dec. 2003).
Brown, et al. J. Chem. Soc. 545 (1959).
Byrne, et al. J. Chem. Soc. (C):2810 (1971).
Carroccio, et al. Clin. Chem. 49(6):861-867 (2003).
Carson, J. Am. Chem. Soc. 73:1850-1851 (1951).
Chandra, et al. Indian J. Medical Research 60(1):138-142 (1972).
Charlier, et al. Eur. J. Med. Chem. 38:645-659 (2003).
Chattopadhyay et al., Current Science, 87(1) (Jul. 10, 2004).
Chen Wei-Jen et al., Journal of Agricultural and Food Chemistry 52(1), pp. 55-64 (Jan. 1, 2004).
Chou et al. Eur. J. Biochem. 115:207-216 (1981).
Chou, et al. Adv enzyme regul 22:27-55 (1983).
Chou, et al. Eur. J. Biochem. 115:207-216 (1981).
Chou, et al. J. Biol. Chem. 252(18):6438-6442 (1977).
Chou, et al. J. Theor. Biol. 35:285-297 (1972).
Chou, J. Theor. Biol. 59:253-276 (1976).
Chou, et al., TIPS, pp. 450-454, Nov. 1983.
Cohen, Protein Kinases—the major drug targets of the twenty-first century? Nature Reviews, 1: 309-315 (2002).
Costa, et al. Digest. Liver Dis. 35:642-647 (2003).
Davies, WL. Abstract—Fertiliser, Feeding Stuffs and Farm Supplies J. 11:694 (1926).

De Keukeleire "Fundamentals of Beer and Hop Chemistry" Quimica Nova, 23(1) pp. 108-112 (2000).
Ding, et al. Biochem. Biophy. Res. Comm. 261:218-223 (1999).
EP Search Report for EP App. No. 07809709.4.
European Search Report EP 05 723 839.6.
European Search Report for corresponding EP Application No. 02737562.5 (4 pages).
European Search Report for related European Application No. 02784313.5.
Exercise as Treatment for Arthritis, Rheumatic and Immunologic Diseases, Cleveland Clinic, www.clevelandclinic.org, Mar. 14, 2000.
Extended European Search Report EP 10162893.1.
Extended European Search Report EP 07717798.8.
Extended European Search Report EP 07809708.6.
Foucault et al., J. Chromatography A 808(1-2):3-22 (May 29, 1998); abstract only (3 pages).
Friedman, et al. J Cutan Med. Surg. 6(5):449-459 (2002).
Gao et al., J. Food Sci. Nutr. vol. 9, pp. 240-244 (2004).
Gerhauser, Beer Constituents as Potential Cancer Chemopreventive Agents, EP Journal of Cancer 41; 1941-1954: (2005).
Germany, "The Absolutely German Drink," contents of beer, 2004, 5 pages.
Gilani, "Studies on Antihypertensive and Antispasmodic Activities of Methanol Extract of Acacia nilotica Pods", Phytotherapy Research 13: 665-669 (1999).
Goldstein, et al. Am. J. Gastroenterol. 96(4):1019-1027 (2001).
Halter, et al. Gut 49:443-453 (2001).
Hamberg, et al. J. Bio. Chem. 246(22):6713-6721 (1971).
Huang, et al. Cancer Res. 51:813-819 (1991).
Information on ArthroTrim™ product, downloaded from Internet Aug. 30, 2002.
Information on "Hops and Beer Flavours", IOB Technical Symposium, Apr. 2001, pp. 1-9.
Information on "Zyflamend and Zyflamend PM", downloaded from Internet Aug. 30, 2002.
International Search Report for Corresponding PCT Application No. PCT/US05/41018; 2pp.
International Search Report for PCT /US06/30920, Aug. 3, 2007, 3 pages.
International Search Report for PCT/US02/19617.
International Search Report for PCT/US04/16043.
International Search Report for PCT/US06/47196.
Jach, Przegl Dermatol. 65(4):379-381 (1978).
Jafri et al., Pakistan Journal of Science, vol. 61, No. 4, pp. 220-222 (Dec. 2009).
Kaltner, Investigation of formation of Hops Aroma and technological Measures for Products of Hops-Aromatic Beers, Technical University of Munich, 7 pp. corresponding to KalMer, D., Technische Universitat Munchen, (Nov. 30, 2000), pp. 1-193, plus Tabs. AH1-AH31.
Kanematsu, et al. J Bone Miner Res 12(11):1789-1796 (1997).
Konda, et al., Arthritis & Rheumatism 62(6): 1683-1692, (2010).
Lamy Virginie et al., Apoptosis, an Int'l Journal on Programmed Cell Death,13(10), pp. 1232-1242 (Aug. 25, 2008).
Lamy Virginie et al., Carcinogenesis, 28(7), pp. 1575-1581 (Jul. 2007).
Lerman et al, FASEB Journal, Fed. Of American Soc. For Experimental Biol., vol. 18, No. 4-5 (Jan. 1, 2004).
Lopes, Curr. Med Res Opin. 8(3):145-149 (1982).
Mannering et al., Food, Nutrition and Chemical Toxicity X(X), pp. 311-323 (Jan. 1, 1993).
Meling, et al. Scand. J. Gastroenterol. 31:339-344 (1996).
Minich et al., Journal of nutrition and Metabolism, vol. 2010, article ID 467316, pp. 1-11, (2010).
Newark, et al., "Beyond Aspirin", pp. 147-151, Hohm Press (2000).
Noreen, et al. J. Nat. Prod 61:2-7 (1998).
Office Action issued for U.S. Appl. No. 11/667,614 mailed Apr. 16, 2010.
Office Action issued for U.S. Appl. No. 11/667,615 mailed Mar. 16, 2010.
Office Action issued for U.S. Appl. No. 11/701,583 mailed Feb. 8, 2008.
Office Action issued for U.S. Appl. No. 11/701,583 mailed Jul. 6, 2009.
Office Action issued for U.S. Appl. No. 11/701,583 mailed Nov. 26, 2008.
Office Action issued in U.S. Appl. No. 10/464,834 on Aug. 3, 2010.
Office Action issued in U.S. Appl. No. 10/532,388 on Mar. 26, 2010.
Office Action issued in U.S. Appl. No. 10/590,301 on Aug. 19, 2010.
Office Action issued in U.S. Appl. No. 10/590,424 on Jun. 29, 2010.
Office Action issued in U.S. Appl. No. 10/789,814 on Jun. 11, 2010.
Office Action issued in U.S. Appl. No. 11/344,556 on Sep. 3, 2010.
Office Action issued in U.S. Appl. No. 11/344,556 on Dec. 16, 2009.
Office Action issued in U.S. Appl. No. 11/344,556 on Mar. 27, 2009.
Office Action issued in U.S. Appl. No. 11/344,557 on Mar. 25, 2010.
Office Action issued in U.S. Appl. No. 11/344,557 on Apr. 21, 2008.
Office Action issued in U.S. Appl. No. 11/344,557 on Aug. 28, 2009.
Office Action issued in U.S. Appl. No. 11/344,557 on Jan. 10, 2007.
Office Action issued in U.S. Appl. No. 11/344,557 on Sep. 26, 2007.
Office Action issued in U.S. Appl. No. 11/649,584 on Mar. 3, 2010.
Office Action issued in U.S. Appl. No. 11/344,552 on Sep. 8, 2010.
Office Action issued in U.S. Appl. No. 11/501,393 on Aug. 25, 2010.
Office Action issued in U.S. Appl. No. 12/030,335 on Oct. 21, 2010.
Office Action issued in U.S. Appl. No. 11/636,867 on Aug. 30, 2010.
Office Action issued in U.S. Appl. No. 11/729,696 on Mar. 25, 2010.
Pairet, et al. Inflamm. Res 47(supp. 2), s93-s101 (1998).
Panglisch, Monafsschrift fuer Brauwissen Schaft, 43(1), 4-16 (1990).
Parts per Milliion, 1 page, 2004.
Pippa, et al. Scand. J. Gastroenterol. Suppl. 167:32-35 (1989).
Plewig, et al. J Invest. Dermatol. 65(6):532-536 (1975).
Poullis ,et al. J. Gastroenterol. Hepatol. 18:756-762 (2003).
Provital Group, Rosemary-eco Botany, 2007, 9 pages.
Q & A, (what does ppm or ppb mean?) 3 pages, 2004.
Rahman, M.M., et al., "Conjugated linoleic acid inhibits osteoclast differentiation of RAW264.7 cells by modulating RANKL signaling" J. Lipid Res., 47(8): 1739-1748, (2006).
Ringbom, et al. J. Nat Prod 61:1212-1215 (1998).
Røseth, Digest. Liver Dis. 35:607-609 (2003).
Schjerven, et al. Br. J. Dermatol. 149:484-491 (2003).
Shah, et al. Gut 48:339-346 (2001).
Shimamura, et al. Biochem. Biophys. Res. Comm. 289:220-224 (2001).
Shureiqi, et al. Cancer Res. 61:6307-6312 (2001).
Sivri, Fundam. Clinic. Pharmacol. 18:23-31 (2004).
Smith, et al., Natural Foam Stabilizing and Bittering Compounds Derived From Hops, Journal of the American Society of Brewing Chemists, vol. 56, No. 2, 1998, pp. 52-57.
Stephan T E et al., Biochemical Pharmacology, 55(4), pp. 505-514, (Feb. 15, 1998).
Stevens, Xanthohumol and related Prenylflavonoids from Hops and Beer: To Your Good Health, Science Direct, 2pp (2004).
Subbaramaiah, et al. Cancer Res. 60:2399-2404 (2000).
Suh, et al. Cancer Res 58:717-723 (1988).
Supplemental European Search Report for EP 07845228.
Supplementary European Search Report from related EP Application No. 05851567, 8PP.
Supplementary Partial European Search Report for related European Patent Application No. 05723895.8, 5 pages (2007).
Tagashira M et al., Bioscience, Biotechnology, and Biochemistry, 59(4), pp. 740-742 (Apr. 1995).
The national. 3 pages (1999).
Tibble, et al. Drugs Today 37(2):85-96 (2001).
Tibble, et al. Gut 45:362-366 (1999).
Tobe, et al. Biosci. Biotech. Biochem 61(1):158-159 (1997).
Turmeric: The Ayurvedic Spice of Life, published at www.bioponic.com/pdfs/TurmericAyurveda.pdf (2003).
US News and world report re Palliative Care, 10 pages (2008).
Van Montfrans et al. Inflammatory Signal Transduction in Crohn's Disease and Novel Therapeutic Approaches. Science Direct, Jun. 2, 2002, 20 pages. Biochemical Pharmacology, vol. 64, issues 5-6.
Vanhoenacker, et al., Journal of Chromatography, vol. 1035, No. 1, (Apr. 30, 2004), pp. 53-61.
Verzele, et al. Chemistry and analysis of hop and beer bitter acids, Developments in food science, 27, pp. 44-51, 88-139 (1991).

Verzele and De Keukeleire (eds.) Chemistry and Analysis of Hop and Beer Bitter Acids; Elsevier, Chapters 5, 20 pages (1991).
Verzele and De Keukeleire (eds.) Chemistry and Analysis of Hop and Beer Bitter Acids; Elsevier, Chapters 6, 8 pages (1991).
Wang, et al. Free Radical Biology & Medicine 27:612-616 (1999).
Ward, et al., Therapeutic Potential of Phosphoinositide 3-Kinase Inhibitors, Chemistry & Biology, vol. 10, 207-210, Mar. 2003,.
Warner, et al. Proc Natl Acad Sci USA 96:7563-7568 (1999).
Written Opinion for corresponding PCT Application No. PCT/US05/41018; 3 pp.
Yamamoto, et al. Abstract—Prostaglandins & Other Lipid Mediators 59:1-235 (1999).
Yamamoto, FEBS Letters 465:103-106 (2000).
Yui, et al. Biol. Pharm. Bull. 26(6):753-760 (2003).
Zhao Feng et al., Biological and Pharmaceutical Bulletin, 26(1), pp. 61-65 (Jan. 2003).
Extended European Search Report issued in European Patent Application No. EP 10162891.5 dated Sep. 19, 2012.

* cited by examiner

[A]

[B]

[C]

COMPOSITIONS THAT TREAT OR INHIBIT PATHOLOGICAL CONDITIONS ASSOCIATED WITH INFLAMMATORY RESPONSE

RELATED APPLICATIONS

This application is the U.S. National Phase under 35 U.S.C. §371 of International Application No. PCT/US03/33362, filed on Oct. 20, 2003, which claims priority to U.S. application Ser. No. 10/464,410, filed on Jun. 18, 2003 (now U.S. Pat. No. 8,142,819), and U.S. application Ser. No. 10/464,834, filed on Jun. 18, 2003 (now abandoned), and U.S. application Ser. No. 10/400,293, filed on Mar. 26, 2003 (now abandoned), and U.S. application Ser. No. 10/401,283, filed on Mar. 26, 2003 (now abandoned), and U.S. Provisional Application No. 60/450,237, filed Feb. 25, 2003 (now expired), and U.S. Provisional Application No. 60/420,383, filed Oct. 21, 2002 (now expired). The disclosures of each of the above Applications is incorporated herein by reference in its entirety.

BACKGROUND OF THE INVENTION

1. Field of the Invention

The present invention relates generally to compositions that can be used to treat or inhibit pathological conditions associated with tissue-specific activation of inflammation and/or NFκB, to methods of modulating inflammation, including in cells, and to methods of modulating NFκB in cells. More specifically, the invention relates to a composition comprising hops extracts or derivatives thereof or a fraction isolated or derived from hops, which can optionally be combined with a second component, such as rosemary, an extract derived from rosemary, a compound derived from rosemary, a triterpene species, a diterpene lactone species, and tryptanthrin. The invention further relates to methods of using the compositions to inhibit expression of cyclooxygenase-2 (COX-2), inhibit synthesis of prostaglandins selectively in target cells, inhibit inflammatory responses selectively in target cells, and/or inhibit NFκB activation selectively in target cells.

2. Description of the Related Art

Cyclooxygenase (prostaglandin endoperoxide synthase, EC 1.14.991, COX) catalyzes the rate-limiting step in the metabolism of arachidonic acid to prostaglandin $H_2$ ($PGH_2$), which is further metabolized to various prostaglandins, prostacyclin and thromboxane A2 (c.f. FIG. 1). In the early 1990s, it was established that COX exists in two isoforms, commonly referred to as COX-1 and COX-2. It was subsequently determined that the COX-1 and COX-2 proteins are derived from distinct genes that diverged well before birds and mammals. Prostaglandins (PGs) generated via the COX-1 and COX-2 pathways are identical molecules and therefore have identical biological effects. COX-1 and COX-2, however, may generate a unique pattern and variable amounts of eicosanoids; therefore, relative differences in the activation of these isozymes may result in quite dissimilar biological responses. Differences in the tissue distribution and regulation of COX-1 and COX-2 are now considered crucial for the beneficial as well as adverse effects of COX inhibitors.

The generally held concept (COX dogma) is that COX-1 is expressed constitutively in most tissues whereas COX-2 is the inducible enzyme triggered by pro-inflammatory stimuli including mitogens, cytokines and bacterial lipopolysaccharide (LPS) in cells in vitro and in inflamed sites in vivo. Based primarily on such differences in expression, COX-1 has been characterized as a housekeeping enzyme and is thought to be involved in maintaining physiological functions such as cytoprotection of the gastric mucosa, regulation of renal blood flow, and control of platelet aggregation. COX-2 is considered to mainly mediate inflammation, although constitutive expression is found in brain, kidney and the gastrointestinal tract. Therefore, it would be desirable to down-regulate tissue-specific or cell-specific expression of COX-2.

Arachidonic acid serves as the primary substrate for the biosynthesis of all PGs. PGs are ubiquitous hormones that function as both paracrine and autocrine mediators to affect a myriad of physiological changes in the immediate cellular environment. The varied physiological effects of PGs include inflammatory reactions such as rheumatoid arthritis and osteoarthritis, blood pressure control, platelet aggregation, induction of labor and aggravation of pain and fever. The discovery 30 years ago that aspirin and other non-steroidal analgesics inhibited PG production identified PG synthesis as a target for drug development. There are at least 16 different PGs in nine different chemical classes, designated PGA to PGI. PGs are part of a larger family of 20-carbon-containing compounds called eicosanoids; they include prostacyclins, thromboxanes, and leukotrienes. The array of PGs produced varies depending on the downstream enzymatic machinery present in a particular cell type. For example, endothelial cells produce primarily $PGI_2$, whereas platelets mainly produce $TXA_2$.

Prostaglandins (PG) are believed to play an important role in maintenance of human gastric mucosal homeostasis. Current dogma is that COX-1 is responsible for PG synthesis in normal gastric mucosa in order to maintain mucosal homeostasis and that COX-2 is expressed by normal gastric mucosa at low levels, with induction of expression during ulcer healing, following endotoxin exposure or cytokine stimulation. It now appears that both COX-1 and COX-2 have important physiological roles in the normal gastric mucosa.

Compounds that inhibit the production of PGs by COX have become important drugs in the control of pain and inflammation. Collectively these agents are known as non-steroidal anti-inflammatory drugs (NSAIDs) with their main indications being osteoarthritis and rheumatoid arthritis. However, the use of NSAIDs, and in particular aspirin, has been extended to prophylaxis of cardiovascular disease. Over the last decade, considerable effort has been devoted to developing new molecules that are direct inhibitors of the enzymatic activity of COX-2, with the inference that these compounds would be less irritating to the stomach with chronic use. Therefore, it would be desirable to inhibit inflammation response selectively in target cells.

U.S. patent application 2002/0086070A1 of Kuhrts entitled, "ANTI-INFLAMMATORY AND CONNECTIVE TISSUE REPAIR FORMULATIONS" describes a hops component that has an $IC_{50}$-WHMA COX-2/COX-1 ratio ranging from about 0.23 to about 3.33. Example 1 of the application describes a composition containing an extract obtained through supercritical carbon dioxide extraction of whole hops ($CO_2$-extract) comprising 42% humulone.

U.S. Pat. No. 6,391,346 entitled, "ANTI-INFLAMMATORY, SLEEP-PROMOTING HERBAL COMPOSITION AND METHOD OF USE" describes an orally administered composition capable of reducing inflammation in animals, while promoting sleep for such animals. The composition contains hydroalcoholic extract of hops and supercritical carbon dioxide extract of hops which are used to promote sleep.

An ideal formulation for the treatment of inflammation would inhibit the induction and activity of COX-2 without inhibiting the synthesis of $PGE_2$ in gastric mucosal cells. However, conventional non-steroidal anti-inflammatory drugs lack the specificity of inhibiting COX-2 without affecting gastric $PGE_2$ synthesis and are at risk to cause damages on the gastrointestinal system, when used for extended periods. Indeed, even the newly developed, anti-inflammatory drugs such as rofecoxib and celexocib produce untoward gastric toxicity in the form of induced spontaneous bleeding and delay of gastric ulcer healing.

Thus, it would be useful to identify a formulation of compounds that would specifically inhibit or prevent the synthesis of prostaglandins by COX-2 with little or no effect on synthesis of $PGE_2$ in the gastric mucosa. Such a formulation, which would be useful for preserving the health of joint tissues, for treating arthritis or other inflammatory conditions, has not previously been discovered. The term "specific or selective COX-2 inhibitor" was coined to embrace compounds or mixtures of compounds that selectively inhibit COX-2 over COX-1. However, while the implication is that such a calculated selectivity will result in lower gastric irritancy, unless the test materials are evaluated in gastric cells, the term "selective COX-2 inhibitor" does not carry assurance of safety to gastrointestinal cells. Only testing of compound action in target tissues, inflammatory cells and gastric mucosal cells, will identify those agents with low potential for stomach irritation.

The major problem associated with ascertaining COX-2 selectivity (i.e. low gastric irritancy) is that differences in assay methodology can have profound effects on the results obtained. Depicted in Table 1 are the categories of the numerous in vitro assays that have been developed for testing and comparing the relative inhibitory activities of NSAID and natural compounds against COX-1 and COX-2. These test systems can be classified into three groups: (1) systems using animal enzymes, animal cells or cell lines, (2) assays using human cell lines, or human platelets and monocytes, and (3) currently evolving models using human cells that are representative of the target cells for the anti-inflammatory and adverse effects of NSAID and dietary supplements. Generally, models using human cell lines or human platelets and monocytes are the current standard and validated target cell models have not been forthcoming. A human gastric cell line capable of assessing potential for gastric irritancy is a need.

TABLE 1

Classification of test systems for in vitro assays assessing COX-2 selectivity of anti-inflammatory compounds†

TEST SYSTEMS

| ANIMAL | HUMAN | TARGET |
| --- | --- | --- |
| Enzymes | Enzymes | Human Gastric Mucosa Cells |
| Cells | Cells | Human Chondrocytes |
| Cell lines | Cell lines | Human Synoviocytes |

OTHER SYSTEM VARIABLES

1. Source of arachidonic acid - endogenous or exogenous;
2. Various expression systems for gene replication of COX-1 and COX-2;
3. The presence or absence of a COX-2 inducing agent;
4. COX-2 inducing agents are administered at different concentrations and for different periods of time;
5. Duration of incubation with the drug or with arachidonic acid;
6. Variation in the protein concentration in the medium.

†Adapted from Pairet, M. and van Ryn, J. (1998) Experimental models used to investigate the differential inhibition of cyclooxygenase-1 and cyclooxygenase-2 by non-steroidal anti-inflammatory drugs. Inflamm. Res 47, Supplement 2S93-S101 and incorporated herein by reference.

The enzymes used can be of animal or human origin, they can be native or recombinant, and they can be used either as purified enzymes, in microsomal preparations, or in whole-cell assays. Other system variables include the source of arachidonic acid. PG synthesis can be measured from endogenously released arachidonic acid or exogenously added arachidonic acid. In the later case, different concentrations are used in different laboratories.

Second, there are various expression systems for gene replication of recombinant COX-1 and COX-2 enzymes. In addition, the cells transfected with the Cox-1 or Cox-2 gene can be of diverse origins, for instance, insect cell lines or COS cells. Third, the absence or presence of a COX-2 inducing agent can vary. Cells that are stably transfected with the recombinant enzymes express this enzyme constitutively and no inducing agent is used. This is in fundamental contrast with other cells in which COX-2 has to be induced. Induction of COX-2 is commonly performed using bacterial LPS or various cytokines such as interleukin-1β or tumor necrosis factor. Additionally, these endotoxins and cytokines are administered at various concentrations.

Fourth, the duration of the incubation with the test agent, the COX-2 inducing agent, or with arachidonic acid varies among different laboratories. These differences can influence the quantitative outcome of the study, because the inhibition of COX-2 is time dependent. Finally, the protein concentration of the medium can vary; this is an issue for compounds that can bind avidly to plasma proteins.

A useful assay for COX-2 selectivity would have the following characteristics: (1) whole cells should be used that contain native human enzymes under normal physiological control regarding expression; (2) the cells should also be target cells for the anti-inflammatory and adverse effects of the compounds; (3) COX-2 should be induced, thereby simulating an inflammatory process, rather than being constitutively expressed; and (4) PG synthesis should be measured from arachidonic acid released from endogenous stores rather than from exogenously added arachidonic acid.

Differences in methodology can explain a dramatic difference in the results obtained for COX inhibition. For example, when assayed against the purified enzyme, ursolic acid exhibited an $IC_{50}$ of 130 µM, far outside of possible physiologically obtainable concentrations [Ringbom, T. et al. (1998) *Ursolic acid from Plantago major, a selective inhibitor of cyclooxygenase-2 catalyzed prostaglandin biosynthesis. J Nat Prod* 61, 1212-1215]. In the RAW 264.7 murine macrophage line, Suh et al. report an $IC_{50}$ for ursolic acid of approximately 40 µM [Suh, N., et al. (1998) *Novel triterpenoids suppress inducible nitric oxide synthase (iNOS) and inducible cyclooxygenase (COX-2) in mouse macrophages. Cancer Res* 58, 717-723]; and in phorbol 12-myristate 13-acetate stimulated human mammary cells, the approximate median inhibitory concentration of ursolic acid was 3.0 µM [Subbaramaiah, K. et al. (2000) Ursolic acid inhibits cyclooxygenase-2 transcription in human mammary epithelial cells. *Cancer Res* 60, 2399-2404].

No laboratory has, as yet, developed an ideal assay for COX-2 selectivity. The whole cell system most commonly used for Rx and OTC products is the human whole blood assay developed by the William Harvey Institute [Warner, T. D. et al. (1999) *Nonsteroid drug selectivities for cyclo-oxygenase-1 rather than cyclo-oxygenase-2 are associated with human gastrointestinal toxicity: a full in vitro analysis. Proc Natl Acad Sci USA* 96, 7563-7568]. To date, this assay format has developed more data supporting clinical relevance than any other. However, new research in the role of constitutive expression of COX-2 in normal gastric mucosa necessitates revisiting the relevance of the use of platelets to model COX-1 inhibition in the absence of COX-2. The extrapolation of gastrotoxicity from platelet studies is no longer on a sound molecular basis. The validation of a human gastric mucosal cell line for establishing the potential target tissue toxicity of cyclooxygenase inhibitors represents a critical need for the development of safe and effective anti-inflammatory agents.

NF-κB, a heterodimer of the proteins p50 and RelA, is an inducible eukaryotic DNA binding protein complex that is broadly expressed and plays a pivotal role in regulating multiple biological responses, such as the inflammatory and immune responses in mammalian cells. NF-κB regulate the expression of genes encoding cytokines, chemokines, adhesion molecules, and antimicrobial peptides. Targets of NF-κB include IL-2, the IL-2 receptor, and acute-phase proteins of the liver. In addition to its role in immune responses, NF-κB activation overrides the apoptotic response to TNF and Fas, allowing for proliferation instead.

As shown in FIG. 9, NF-κB is cytoplasmic when inactive, maintained there by IκB. Various stimuli lead to activation of IKK (IκB Kinase), which phosphorylates IκB, marking it for ubiquitination and degradation. Once IκB is degraded, NF-κB is freed to initiate transcription. Following transcriptional activation of a gene, NF-κB is also rapidly degraded.

Therefore, it would be useful to identify a composition that would modulate expression or activity of NF-κB at the onset of inflammation to decrease the inflammatory response. Additionally, compositions that act as modulators of NF-κB can affect a wide variety of disorders in a mammalian body. As a result of inhibiting NFκB, which is a transcription factor for COX-2, the expression of COX-2 can be down-regulated.

An ideal formulation for the treatment of inflammation would inhibit the induction and activity of COX-2 without inhibiting the synthesis of PGE2 in gastric mucosal cells. However, conventional non-steroidal anti-inflammatory drugs lack the specificity of inhibiting COX-2 without affecting gastric PGE2 synthesis and are at risk to cause damages on the gastrointestinal system, when used for extended periods. Indeed, even the newly developed, anti-inflammatory drugs such as rofecoxib (Vioxx®, Merck & Co., Inc.) and celexocib (Celebrex®, Pfizer, Inc.) produce untoward gastric toxicity in the form of induced spontaneous bleeding and delay of gastric ulcer healing.

Thus, it would be useful to identify a natural formulation of compounds that would specifically inhibit or prevent the synthesis of prostaglandins by COX-2 with little or no effect on synthesis of PGE2 in the gastric mucosa. Such a formulation, which would be useful for preserving the health of joint tissues, for treating arthritis or other inflammatory conditions, has not previously been discovered. The term "specific or selective COX-2 inhibitor" was coined to embrace compounds or mixtures of compounds that selectively inhibit COX-2 over COX-1. However, while the implication is that such a calculated selectivity will result in lower gastric irritancy, unless the test materials are evaluated in gastric cells, the term "selective COX-2 inhibitor" does not carry assurance of safety to gastrointestinal cells. Only testing of compound action in target tissues, inflammatory cells and gastric mucosal cells will identify those agents with low potential for stomach irritation.

While glucosamine is generally accepted as being effective and safe for treating osteoarthritis, medical intervention into the treatment of degenerative joint diseases is generally restricted to the alleviation of its acute symptoms. Physicians generally utilize non-steroidal and steroidal anti-inflammatory drugs for treatment of osteoarthritis. These drugs, however, are not suited for long-term therapy because they not only lack the ability to protect cartilage, they can actually lead to degeneration of cartilage or reduction of its synthesis. Moreover, most non-steroidal, anti-inflammatory drugs damage the gastrointestinal system when used for extended periods. Thus, new treatments for arthritis and osteoarthritis combining anti-inflammatory agents with cartilage rebuilding agents are urgently needed.

The joint-protective properties of glucosamine would make it an attractive therapeutic agent for osteoarthritis except for two drawbacks: (1) the rate of response to glucosamine treatment is slower than for treatment with anti-inflammatory drugs, and (2) glucosamine may fail to fulfill the expectation of degenerative remission. In studies comparing glucosamine with non-steroidal anti-inflammatory agents, for example, a double-blinded study comparing 1500 mg glucosamine sulfate per day with 1200 mg ibuprofen, demonstrated that pain scores decreased faster during the first two weeks in the ibuprofen patients than in the glucosamine-treated patients. However, the reduction in pain scores continued throughout the trial period in patients receiving glucosamine and the difference between the two groups turned significantly in favor of glucosamine by week eight. Lopes Vaz, A., Double-blind clinical evaluation of the relative efficacy of ibuprofen and glucosamine sulphate in the management of osteoarthritis of the knee in outpatients, 8 Curr. Med Res Opin. 145-149 (1982). Thus, glucosamine may relieve the pain and inflammation of arthritis, but at a slower rate than the available anti-inflammatory drugs.

An ideal formulation for the normalization of cartilage metabolism or treatment of osteoarthritis would provide adequate chondroprotection with potent anti-inflammatory activity. The optimal dietary supplement for osteoarthritis should enhance the general joint rebuilding qualities offered by glucosamine and attenuate the inflammatory response without introducing any harmful side effects. It should be inexpensively manufactured and comply with all governmental regulations.

However, the currently available glucosamine formulations have not been formulated to optimally attack and alleviate the underlying causes of osteoarthritis and rheumatoid arthritis. Moreover, as with many commercial herbal and dietary supplements, the available formulations do not have a history of usage, nor controlled clinical testing, that might ensure their safety and efficacy.

Therefore, it would be useful to identify a composition that would specifically inhibit or prevent the expression of COX-2 enzymatic activity in inflammatory cells, while having little or no effect on $PGE_2$ synthesis in gastric mucosal cells so that these formulations could be used with no gastrointestinal upset. Furthermore, such formulations should allow for healing of preexisting ulcerative conditions in the stomach.

SUMMARY OF THE INVENTION

Thus, it would be useful to identify a formulation of compounds that would modulate an inflammatory response. It would also be useful to identify a formulation of compounds that would modulate NFκB. Such a formulation has widespread applications.

It would also be useful to identify a formulation of compounds that would inhibit expression of COX-2, inhibit prostaglandin synthesis selectively in target cells, or inhibit inflammation response selectively in target cells. For example, it would also be useful to identify a formulation of compounds that would specifically inhibit or prevent the synthesis of prostaglandins by COX-2 in inflammatory cells with little or no effect on $PGE_2$ synthesis in gastric mucosal cells. Such a formulation, which would be useful for preserving the health of joint tissues, for treating arthritis or other inflammatory conditions, has not previously been discovered. Preferably, the formulations have a median effective concentration for COX-2 inhibition in inflammatory cells that is minimally ten times greater than the median effective concentration for the inhibition of $PGE_2$ synthesis in gastric cells. For example, if the median inhibitory concentration for COX-2 of a test formulation was 0.2 µg/mL in the murine macrophage RAW 264.7, the formulation would not be considered to have low potential for gastric irritancy unless the median inhibitory concentration for $PGE_2$ synthesis in gastric cells was equal to or greater than 2 µg/mL.

A preferred embodiment comprises compositions containing at least one fraction isolated or derived from hops (*Humulus lupulus*). Examples of fractions isolated or derived from hops are alpha acids, isoalpha acids, reduced isoalpha acids, tetra-hydroisoalpha acids, hexa-hydroisoalpha acids, beta acids, and spent hops. Preferred compounds of fractions isolated or derived from hops, include, but are not limited to, humulone, cohumulone, adhumulone, isohumulone, isocohumulone, isoadhumulone, dihydro-isohumulone, dihydro-isocohumulone, dihydro-adhumulone, tetrahydro-isohumulone, tetrahydro-isocohumulone, tetrahydro-adhumulone, hexahydro-isohumulone, hexahydro-isocohumulone, and hexahydro-adhumulone. Preferred compounds can also bear substituents, such as halogens, ethers, and esters.

Other embodiments relate to combinations of components. One embodiment relates to compositions that include, as a first component, an active ingredient isolated or derived from an extract of hops and as a second component at least one member selected from the group consisting of rosemary (*Rosmarinus officinalis* L.), an extract or compound derived from rosemary, a triterpene species or derivatives or conjugates thereof, a diterpene lactone species or derivatives or conjugates thereof, and tryptanthrin or conjugates thereof. Another embodiment relates to compositions that include, as a first component, tryptanthrin or conjugates thereof and as a second component at least one member selected from the group consisting of an active ingredient isolated or derived from an extract of hops, rosemary, an extract or compound derived from rosemary, a triterpene species or derivatives or conjugates thereof, and a diterpene lactone species or derivatives or conjugates thereof. As used herein, an extract refers to an extract containing an active ingredient that effects an activity, for example, inhibiting inflammation, inhibiting inducibility or activity of COX-2, inhibiting prostaglandin synthesis, modulating NFκB, and the like.

Preferred compositions can inhibit the inducibility or activity of COX-2. Compositions of the invention can also function to modulate NFκB. Preferred compositions also can inhibit prostaglandin synthesis selectively in target cells. Preferred compositions also can inhibit inflammation response selectively in target cells. As used herein, an extract refers to an extract containing an active ingredient that effects an activity, for example, inhibiting inflammation, inhibiting inducibility or activity of COX-2, inhibiting prostaglandin synthesis, modulating NFκB, and the like.

The compositions have widespread applications. Preferred compositions can be useful for treating conditions, such as cancer, autoimmune diseases, inflammatory diseases, or neurological diseases, and obesity. Preferred compositions are also believed to be useful for treating conditions, such as HIV-1 infections, rhinovirus infections, and cardiovascular diseases.

Preferred compositions would be useful for, but not limited to, the treatment of inflammation in a subject, and for treatment of other inflammation-associated disorders, such as an analgesic in the treatment of pain and headaches, or as an antipyretic for the treatment of fever. Preferred compositions would be useful to treat arthritis, including but not limited to rheumatoid arthritis, spondyloathopathies, gouty arthritis, osteoarthritis, systemic lupus erythematosis, and juvenile arthritis.

Preferred compositions would be useful in the treatment of asthma, bronchitis, menstrual cramps, tendonitis, bursitis, and skin-related conditions such as psoriasis, eczema, burns and dermatitis. Preferred compositions also would be useful to treat gastrointestinal conditions such as inflammatory bowel disease, Crohn's disease, gastritis, irritable bowel syndrome and ulcerative colitis and for the prevention or treatment of cancer such as colorectal cancer.

Further, preferred compositions would be useful in treating inflammation in such diseases as vascular diseases, migraine headaches, periarteritis nodosa, thyroiditis, aplastic anemia, Hodgkin's disease, sclerodma, rheumatic fever, type I diabetes, myasthenia gravis, multiple sclerosis, sacoidosis, nephrotic syndrome, Behchet's syndrome, polymyositis, gingivitis, hypersensitivity, swelling occurring after injury, myocardial ischemia, peridontal disease, fibromyalgia, atopic dermatitis, insulitis and the like.

Additionally, preferred compositions would also be useful in the treatment of ophthalmic diseases, such as retinopathies, conjunctivitis, uveitis, ocular photophobia, and of acute injury to the eye tissue. Preferred compositions would also be useful in the treatment of pulmonary inflammation, such as that associated with viral infections and cystic fibrosis.

Preferred compositions would also be useful for the treatment of certain nervous system disorders such as cortical dementias including Alzheimer's disease. As inhibitors of COX-2 mediated biosynthesis of $PGE_2$ in inflammatory cells, these compositions would also be useful in the treatment of allergic rhinitis, respiratory distress syndrome, endotoxin shock syndrome, atherosclerosis, and central nervous system damage resulting from stroke, ischemia and trauma.

Preferred embodiments further provides a composition to increase the rate at which glucosamine or chondrotin sulfate function to normalize joint movement or reduce the symptoms of osteoarthritis.

Preferred embodiments also provide for methods of identifying compositions that would specifically inhibit or prevent the synthesis of prostaglandins by COX-2 in inflammatory cells with little or no effect on $PGE_2$ synthesis in gastric mucosal cells.

In addition, the compositions of the invention would also be useful for the treatment of obesity, syndrome X, and the like, by reversing hyperglycemia, hyperinsulinemia, and dyslipidermia by normalizing activation of IkkB kinase beta and hence properly modulating its effect on transcription of NFκB-activated genes, effectively breaking the cytokine (for example, tumor necrosis factor alpha (TNFα) feed-back loop leading to these conditions and diseases.

BRIEF DESCRIPTION OF THE DRAWINGS

FIG. 6 [B] shows densitometric analysis of the immunoblots shown in FIG. 6A. Band intensities were evaluated through densitometric analysis, computed using ScanAnalysis® software (BIOSOFT, Ferguson, Mo.), and recorded as arbitrary Density Units (DU).

FIG. 7[B] is an estimate of the plasma concentrations of test material at each post-dosing time capable of inhibiting $PGE_2$ synthesis in LPS-stimulated RAW 264.7 cells assuming a constant 5:5:1 ratio of components.

DETAILED DESCRIPTION OF THE PREFERRED EMBODIMENT

Figure 1:
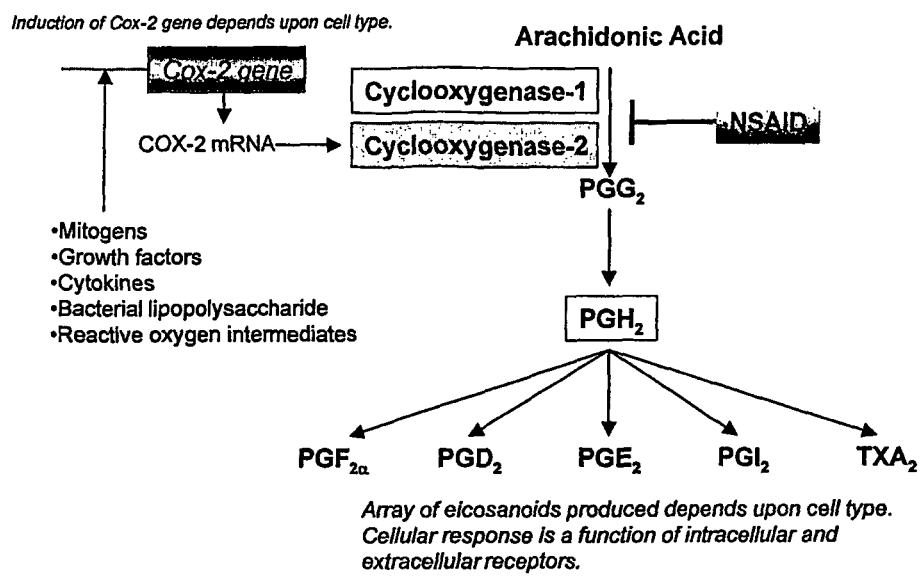
FIG. 1 depicts the induction of cyclooxygenase-2 and the metabolism of arachidonic acid to prostaglandins and other eicosanoids by the cyclooxygenase enzymes. The action of non-steroidal anti-inflammatory agents is through direct inhibition of the cyclooxygenase enzymes.

The present invention relates to the discovery that that a supragenus of components isolated or derived from hops and other compounds result in tissue-specific or cell-specific inhibition of COX-2 expression. Importantly, these compounds are not believed to directly inhibit COX-2 or other enzymes within the prostaglandin synthesis pathway. Preferred embodiments provide compositions and methods for inhibiting COX-2 expression, inhibiting prostanglandin synthesis selectively in target tissues or cells, or inhibiting inflammation response selectively in target tissues or cells. Compositions and methods of the invention can also modulate NFκB.

A preferred embodiment comprises compositions containing fractions or compounds isolated or derived from hops. Examples of fractions isolated or derived from hops are alpha acids, isoalpha acids, reduced isoalpha acids, tetra-hydroisoalpha acids, hexa-hydroisoalpha acids, beta acids, and spent hops. Preferred compounds of the fractions isolated or derived from hops can be represented by a supragenus below:

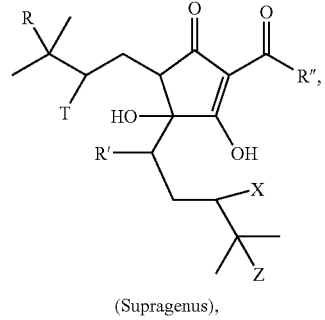

(Supragenus), wherein R' is selected from the group consisting of carbonyl, hydroxyl, OR, and OCOR, wherein R is alkyl; wherein R" is selected from the group consisting of CH(CH₃)₂, CH₂CH(CH₃)₂, and CH(CH₃)CH₂CH₃; and wherein R, T, X, and Z are independently selected from the group consisting of H, F, Cl, Br, I, and π orbital, with the proviso that if one of R, T, X, or Z is a π orbital, then the adjacent R, T, X, or Z is also a π orbital, thereby forming a double bond.

Other preferred compounds of the fractions isolated or derived from hops can be represented by a genus below:

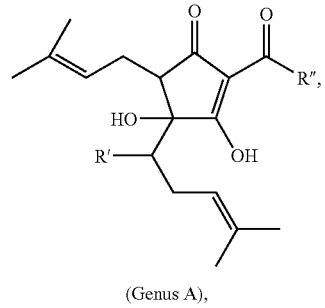

(Genus A), wherein R' is selected from the group consisting of carbonyl, hydroxyl, OR, and OCOR, wherein R is alkyl; and wherein R" is selected from the group consisting of CH(CH$_3$)$_2$, CH$_2$CH(CH$_3$)$_2$, and CH(CH$_3$)CH$_2$CH$_3$.

Other preferred compounds of the fractions isolated or derived from hops can be represented by a genus below:

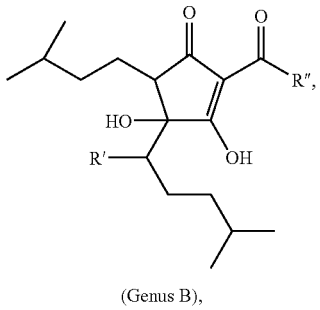

(Genus B), wherein R' is selected from the group consisting of carbonyl, hydroxyl, OR, and OCOR, wherein R is alkyl; and wherein R" is selected from the group consisting of CH(CH$_3$)$_2$, CH$_2$CH(CH$_3$)$_2$, and CH(CH$_3$)CH$_2$CH$_3$.

Examples of preferred compounds of an ingredient isolated or derived from hops, include, but are not limited to, humulone, cohumulone, adhumulone, isohumulone, isocohumulone, isoadhumulone, dihydro-isohumulone, dihydro-isocohumulone, dihydro-adhumulone, tetrahydro-isohumulone, tetrahydro-isocohumulone, tetrahydro-adhumulone, hexahydro-isohumulone, hexahydro-isocohumulone, and hexahydro-adhumulone. The preferred compounds can bear substituents, as shown in the formula above.

Another embodiment comprises composition containing tryptanthrin and conjugates thereof.

Other embodiments relate to combinations of components. In particular embodiments, the compositions of the invention can function to specifically inhibit COX-2 expression, to modulate NFκB, to inhibit prostaglandin synthesis selectively in target cells, or to inhibit inflammation response selectively in target cells. The compositions can exhibit synergistic activity.

One embodiment relates to compositions that include, as a first component, an active ingredient isolated or derived from an extract of hops and as a second component at least one member selected from the group consisting of rosemary, an extract or compound derived from rosemary, a triterpene species or derivatives or conjugates thereof, a diterpene lactone species or derivatives or conjugates thereof, and tryptanthrin or conjugates thereof. Another embodiment relates to compositions that include, as a first component, tryptanthrin or conjugates thereof and as a second component at least one member selected from the group consisting of an active ingredient isolated or derived from an extract of hops, rosemary, an extract or compound derived from rosemary, a triterpene species or derivatives or conjugates thereof, and a diterpene lactone species or derivatives or conjugates thereof.

As used herein, the term "dietary supplement" refers to compositions consumed to affect structural or functional changes in physiology. The term "therapeutic composition" refers to any compounds administered to treat or prevent a disease.

As used herein, the term "effective amount" means an amount necessary to achieve a selected result. Such an amount can be readily determined without undue experimentation by a person of ordinary skill in the art.

As used herein, the term "substantial" means being largely but not wholly that which is specified.

As used herein, the term "COX inhibitor" refers to a composition of compounds that is capable of inhibiting the activity or expression of COX-2 enzymes or is capable of inhibiting or reducing the severity, including pain and swelling, of a severe inflammatory response.

As used herein, the terms "derivatives" or a matter "derived" refer to a chemical substance related structurally to another substance and theoretically obtainable from it, i.e. a substance that can be made from another substance. Derivatives can include compounds obtained via a chemical reaction.

As used herein, the term "inflammatory cell" refers to those cellular members of the immune system, for example B and T lymphocytes, neutrophils or macrophages involved in synthesis of prostaglandins in response to inflammatory signals such as interleukins, tumor necrosis factor, bradykinin, histamine or bacterial-derived components.

As used herein, the term "target cells" refers to that cell population in which the inhibition of PGE$_2$ or other prostaglandin synthesis is desired, such as inflammatory cells, tumor cells, or pulmonary cells. Alternatively, "non-target cells" refers to that cell population in which the inhibition of PGE$_2$ or other prostaglandin synthesis is not desired, such as the gastric mucosal, neural or renal cells.

As used herein, the term "hop extract" refers to the solid material resulting from (1) exposing a hops plant product to a solvent, (2) separating the solvent from the hops plant products, and (3) eliminating the solvent.

As used herein, the term "solvent" refers to a liquid of aqueous or organic nature possessing the necessary characteristics to extract solid material from the hop plant product. Examples of solvents would include, but not limited to, water, steam, superheated water, methanol, ethanol, hexane, chloroform, liquid CO$_2$, liquid N$_2$ or any combinations of such materials.

As used herein, the term "CO$_2$ extract" refers to the solid material resulting from exposing a hops plant product to a liquid or supercritical CO$_2$ preparation followed by removing the CO$_2$.

As used herein, the term "spent hops" refers to the solid and hydrophilic residue from extract of hops.

As used herein, the term "alpha acid" refers to compounds refers to compounds collectively known as humulones and can be isolated from hops plant products including, among others, humulone, cohumulone, adhumulone, hulupone, and isoprehumulone.

As used herein, the term "isoalpha acid" refers to compounds isolated from hops plant products and subsequently have been isomerized. The isomerization of alpha acids can occur thermally, such as boiling. Examples of isoalpha acids include, but are not limited to, isohumulone, isocohumulone, and isoadhumulone.

As used herein, the term "reduced isoalpha acid" refers to alpha acids isolated from hops plant product and subsequently have been isomerized and reduced, including cis and trans forms. Examples of reduced isoalpha acids (RIAA) include, but are not limited to, dihydro-isohumulone, dihydro-isocohumulone, and dihydro-adhumulone.

As used herein, the term "tetra-hydroisoalpha acid" refers to a certain class of reduced isoalpha acid. Examples of tetrahydroisoalpha acid (THIAA) include, but are not limited to, tetra-hydro-isohumulone, tetra-hydro-isocohumulone and tetra-hydro-adhumulone.

As used herein, the term "hexa-hydroisoalpha acid" refers to a certain class of reduced isoalpha acid. Examples of hexa-hydroisoalpha acids (HHIAA) include, but are not limited to, hexa-hydro-isohumulone, hexa-hydro-isocohumulone and hexa-hydro-adhumulone.

As used herein, the term "beta-acid fraction" refers to compounds collectively known as lupulones including, among others, lupulone, colupulone, adlupulone, tetrahydroisohumulone, and hexahydrocolupulone.

As used herein, the term "essential oil fraction" refers to a complex mixture of components including, among others, myrcene, humulene, beta-caryophyleen, undecane-2-on, and 2-methyl-but-3-en-ol.

As used herein, "conjugates" of compounds means compounds covalently bound or conjugated to a member selected from the group consisting of mono- or di-saccharides, amino acids, sulfates, succinate, acetate, and glutathione. Preferably, the mono- or di-saccharide is a member selected from the group consisting of glucose, mannose, ribose, galactose, rhamnose, arabinose, maltose, and fructose.

As used herein, the term "fats" refers to triacylglyerol esters of fatty acids.

As used herein, the term "waxes" refers to triacylglycerol ethers of or esters of extremely long chain (>25 carbons) fatty alcohols or acids.

Hops

Hop extraction in one form or another goes back over 150 years to the early nineteenth century when extraction in water and ethanol was first attempted. Even today an ethanol extract is available in Europe, but by far the predominant extracts are organic solvent extracts (hexane) and $CO_2$ extracts (supercritical and liquid). $CO_2$ (typically at 60 bars pressure and 50 to 10° C.) is in a liquid state and is a relatively mild, non-polar solvent highly specific for hop soft resins and oils. Beyond the critical point, typically at 300 bars pressure and 60° C., $CO_2$ has the properties of both a gas and a liquid and is a much stronger solvent. The composition of the various extracts is compared in Table 2.

TABLE 2

Hop Extracts (Percent W/W)

| Component | Hops | Organic Solvent | Super-Critical $CO_2$ | Liquid $CO_2$ |
| --- | --- | --- | --- | --- |
| Total resins | 12-20 | 15-60 | 75-90 | 70-95 |
| Alpha-acids | 2-12 | 8-45 | 27-55 | 30-60 |
| Beta-acids | 2-10 | 8-20 | 23-33 | 15-45 |
| Essential oils | 0.5-1.5 | 0-5 | 1-5 | 2-10 |
| Hard resins | 2-4 | 2-10 | 5-11 | None |
| Tannins | 4-10 | 0.5-5 | 0.1-5 | None |
| Waxes | 1-5 | 1-20 | 4-13 | 0-10 |
| Water | 8-12 | 1-15 | 1-7 | 1-5 |

At its simplest, hop extraction involves milling, pelleting and re-milling the hops to spread the lupulin, passing a solvent through a packed column to collect the resin components and finally, removal of the solvent to yield a whole or "pure" resin extract.

The main organic extractants are strong solvents and in addition to virtually all the lupulin components, they extract plant pigments, cuticular waxes, water and water-soluble materials.

Supercritical $CO_2$ is more selective than the organic solvents and extracts less of the tannins and waxes and less water and hence water-soluble components. It does extract some of the plant pigments like chlorophyll but rather less than the organic solvents do. Liquid $CO_2$ is the most selective solvent used commercially for hops and hence produces the most pure whole resin and oil extract. It extracts hardly the hard resins or tannins, much lower levels of plant waxes, no plant pigments and less water and water-soluble materials.

As a consequence of this selectivity and the milder solvent properties, the absolute yield of liquid $CO_2$ extract per unit weight of hops is less than when using the other mentioned solvents. Additionally, the yield of alpha acids with liquid $CO_2$ (89-93%) is lower than that of supercritical $CO_2$ (91-94%) or the organic solvents (93-96%). Following extraction there is the process of solvent removal, which for organic solvents involves heating to cause volatilization. Despite this, trace amounts of solvent do remain in the extract. The removal of $CO_2$, however, simply involves a release of pressure to volatize the $CO_2$.

Figure 2:
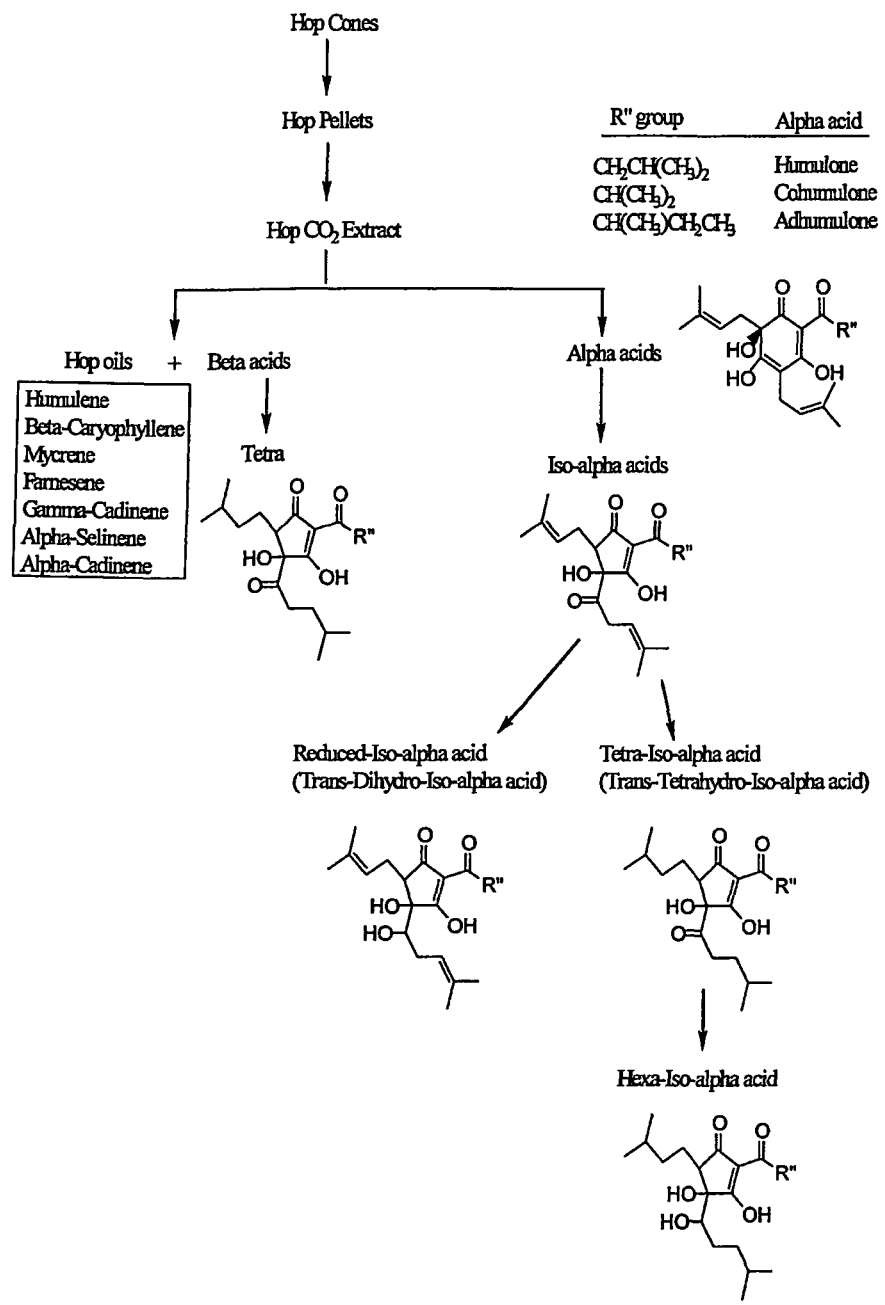
FIG. 2 shows an outline of fractions and compounds that can be obtained from hops.

As shown in FIG. 2, hops $CO_2$ extracts can be fractionated into components, including hops oils, beta acids, and alpha acids. Hops oils include, but not limited to, humulene, beta-caryophyllene, mycrene, farnescene, gamma-cadinene, alpha-selinene, and alpha-cadinene. Beta acids include, but are not limited to, lupulone, colupulone, adlupulone, tetrahydroisohumulone, and hexahydrocolupulone, collectively known as lupulones. Beta acids can be isomerized and reduced. Beta acids are reduced to give tetra-beta acids. Alpha acids include, but are not limited to, humulone, cohumulone, adhumulone, hulupone, and isoprehumulone. Alpha acids can be isomerized to give isoalpha acids. Iso-alpha acids can be reduced to give reduced-isoalpha acids, tetra-hydroisoalpha acids, and hexa-hydroisoalpha acids.

A preferred embodiment comprises compositions containing fractions or compounds isolated or derived from hops. Examples of fractions isolated or derived from hops are alpha acids, isoalpha acids, reduced isoalpha acids, tetra-hydroisoalpha acids, hexa-hydroisoalpha acids, beta acids, and spent hops. Preferred compounds of the fractions isolated or derived from hops can be represented by a supragenus below:

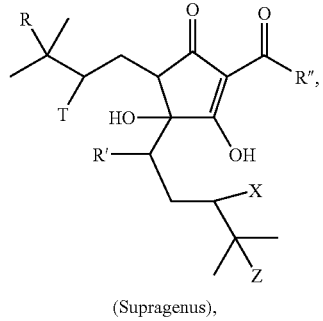

(Supragenus), wherein R' is selected from the group consisting of carbonyl, hydroxyl, OR, and OCOR, wherein R is alkyl; wherein R" is selected from the group consisting of $CH(CH_3)_2$, $CH_2CH(CH_3)_2$, and $CH(CH_3)CH_2CH_3$; and wherein R, T, X, and Z are independently selected from the group consisting of H, F, Cl, Br, I, and π orbital, with the proviso that if one of R, T, X, or Z is a π orbital, then the adjacent R, T, X, or Z is also a π orbital, thereby forming a double bond.

Other preferred compounds of the fractions isolated or derived from hops can be represented by a genus below:

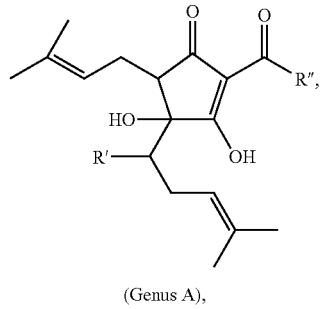

(Genus A), wherein R' is selected from the group consisting of carbonyl, hydroxyl, OR, and OCOR, wherein R is alkyl; and wherein R" is selected from the group consisting of CH(CH$_3$)$_2$, CH$_2$CH(CH$_3$)$_2$, and CH(CH$_3$)CH$_2$CH$_3$.

Other preferred compounds of the fractions isolated or derived from hops can be represented by a genus below:

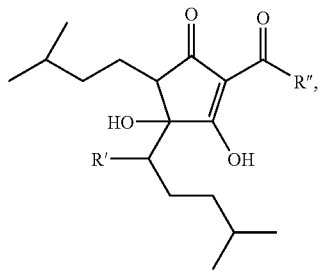

(Genus B), wherein R' is selected from the group consisting of carbonyl, hydroxyl, OR, and OCOR, wherein R is alkyl; and wherein R" is selected from the group consisting of CH(CH$_3$)$_2$, CH$_2$CH(CH$_3$)$_2$, and CH(CH$_3$)CH$_2$CH$_3$.

Figure 3:
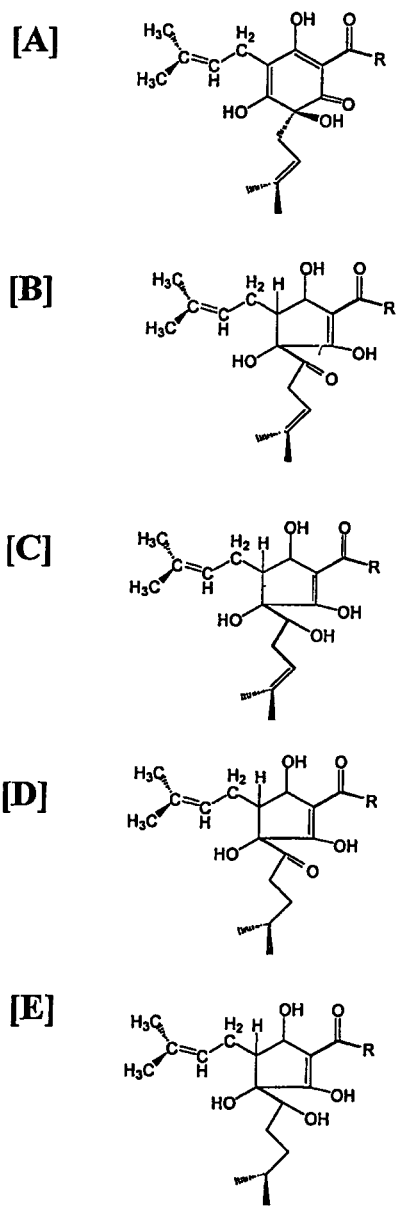
FIG. 3 illustrates [A] the alpha-acid genus (AA) and representative species humulone (R=—$CH_2CH(CH_3)_2$), cohumulone (R=, —$CH(CH_3)_2$), and adhumulone (R=—$CH(CH_3)CH_2CH_3$); [B] the isoalpha acid genus (IAA) and representative species isohumulone (R=—$CH_2CH(CH_3)_2$), isocohumulone (R=, —CH(CH₃)₂), and isoadhumulone (R=—CH(CH₃)CH₂CH₃); [C] the reduced isomerized isoalpha acid genus (RIAA) and representative species dihydro-isohumulone (R=—CH₂CH(CH₃)₂) dihydro-isocohumulone (R=, —CH(CH₃)₂), and dihydro-adhumulone (R=—CH(CH₃)CH₂CH₃); [D] the tetra-hydroisoalpha acid genus (THIAA) and representative species tetra-hydro-isohumulone (R=—CH₂CH(CH₃)₂), tetra-hydro-isocohumulone ((R=, —CH(CH₃)₂), and tetra-hydro-adhumulone R=—CH(CH₃)CH₂CH₃); [E] and the hexa-hydroisoalpha acid (HHIAA) genus with representative species hexa-hydro-isohumulone (R=—CH₂CH(CH₃)₂) hexa-hydro-isocohumulone (R=, —CH(CH₃)₂), and hexa-hydro-adhumulone (R=—CH(CH₃)CH₂CH₃).

As shown in FIG. 3, examples of preferred compounds of an ingredient isolated or derived from hops, include, but are not limited to, humulone, cohumulone, adhumulone, isohumulone, isocohumulone, isoadhumulone, dihydro-isohumulone, dihydro-isocohumulone, dihydro-adhumulone, tetrahydro-isohumulone, tetrahydro-isocohumulone, tetrahydro-adhumulone, hexahydro-isohumulone, hexahydro-isocohumulone, and hexahydro-adhumulone. The preferred compounds can bear substituents, as shown in the formula above.

The identification of humulone from hops extract as an inhibitor of bone resorption is reported in Tobe, H. et al. 1997. (Bone resorption Inhibitors from hop extract. Biosci. Biotech. Biochem 61(1)158-159.) Tobe et al. merely discloses the use of humulone, cohumulone, adhumulone, isohumulone, isocohumulone, and isoadhumulone for treating osteoporosis. Later studies by the same group characterized the mechanism of action of humulone as inhibition of COX-2 gene transcription following TNFalpha stimulation of MC3T3, E1 cells [Yamamoto, K. 2000. Suppression of cyclooxygenase-2 gene transcription by humulon of beer hop extract studied with reference to the glucocorticoid receptor. FEBS Letters 465: 103-106]. The authors concluded that the action of humulone (also humulon) was similar to that of glucocorticoids, but that humulone did not function through the glucocorticoid receptor. While these results establish that humulone inhibits PGE$_2$ synthesis in MC3T3 cells (osteoblasts) at the gene level, one skilled in the art would not assume that these results would necessarily occur in immune inflammatory cells or other cell lines. Example 5 herein demonstrates the high degree of tissue selectivity of hops compounds and derivatives.

Preferred embodiments provide compositions and methods for inhibiting expression of COX-2, modulating NFκB tissue specifically and cell specifically, inhibiting synthesis of prostaglandins selectively in target cells, and inhibiting inflammatory response selectively in target cells. Preferred methods comprise a step of administering to a mammal a composition of the preferred embodiments. Preferred embodiments comprise a fraction isolated or derived from hops. A certain composition comprises alpha acids, isoalpha acids, reduced isoalpha acids, tetra-hydroisoalpha acids, hexa-hydroisoalpha acids, beta acids, or spent hops from hops extract or derivatives thereof. Preferred compounds of the fractions isolated or derived from hops can be represented by a supragenus below:

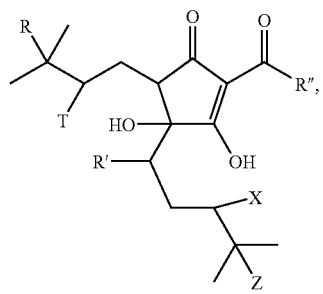

(Supragenus), wherein R' is selected from the group consisting of carbonyl, hydroxyl, OR, and OCOR, wherein R is alkyl; wherein R" is selected from the group consisting of CH(CH$_3$)$_2$, CH$_2$CH(CH$_3$)$_2$, and CH(CH$_3$)CH$_2$CH$_3$; and wherein R, T, X, and Z are independently selected from the group consisting of H, F, Cl, Br, I and π orbital, with the proviso that if one of R, T, X, or Z is a π orbital, then the adjacent R, T, X, or Z is also a π orbital, thereby forming a double bond. Other preferred compounds of the fractions isolated or derived from hops can be represented by a genus below:

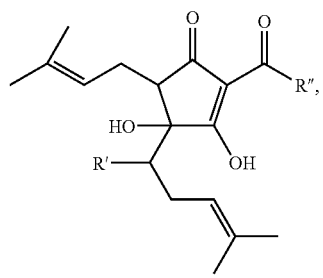

(Genus A), wherein R' is selected from the group consisting of carbonyl, hydroxyl, OR, and OCOR, wherein R is alkyl; and wherein R" is selected from the group consisting of CH(CH$_3$)$_2$, CH$_2$CH(CH$_3$)$_2$, and CH(CH$_3$)CH$_2$CH$_3$. Other preferred compounds of the fractions isolated or derived from hops can be represented by a genus below:

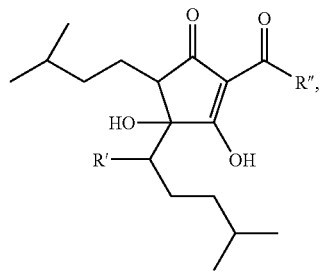

(Genus B), wherein R' is selected from the group consisting of carbonyl, hydroxyl, OR, and OCOR, wherein R is alkyl; and wherein R" is selected from the group consisting of $CH(CH_3)_2$, $CH_2CH(CH_3)_2$, and $CH(CH_3)CH_2CH_3$. The preferred embodiments contemplate compositions comprising beta acids or isomerized or reduced beta acids. Preferably, the alpha acid, isoalpha acid, reduced isoalpha acid, tetra-hydroisoalpha acid, hexa-hydroisoalpha acid, beta acid, or spent hops of the preferred embodiments is made from hops extract. More preferably, the alpha acid, isoalpha acid, reduced isoalpha acid, tetra-hydroisoalpha acid, hexa-hydroisoalpha acid, beta acid, or spent hops of the preferred embodiments is made from $CO_2$ extract of hops.

Tryptanthrin

Preferred embodiments can provide compositions and methods for inhibiting expression of COX-2, modulating NFκB tissue specifically and cell specifically inhibiting synthesis of prostaglandins selectively in target cells, and inhibiting inflammatory response selectively in target cells. Preferred methods comprise a step of administering to a mammal a composition of the preferred embodiments. A certain composition comprises tryptanthrin and conjugates thereof.

Figure 4:
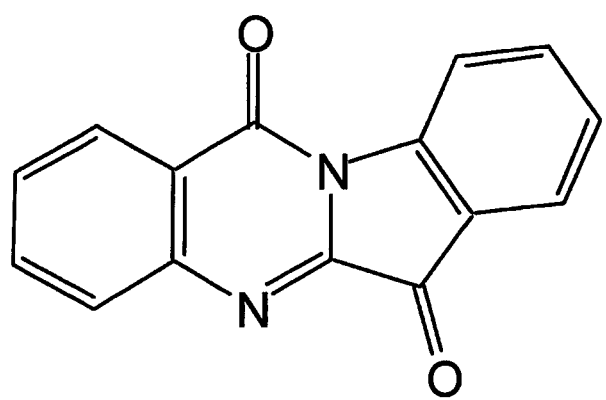
FIG. 4 illustrates the chemical structure of tryptanthrin.

Depicted in FIG. 4, tryptanthrin is a natural compound found in certain herbs, such as *Polygonum tinctorium* and *Isatis tinctoria*. In traditional Chinese medicine this herb is known as Da Qing Ye or Qing Dai. The herb has demonstrated antibacterial and antiviral activity. It has antipyretic, anti-inflammatory and choleretic properties. Increased phagocytic activity of leukocytes and relaxation of intestinal smooth muscle are additional properties of Qing Dai.

Rosemary

Certain of preferred embodiments also include delivering an effective amount of rosemary, rosemary extract, or compounds derived from rosemary with the fraction isolated or derived from hops or tryptanthrin. Preferred additions include, but are not limited to, rosemary, rosemary extract, or those compounds known to be found in rosemary or extracts of rosemary. These include 1,8-cineole, 19-alpha-hydroxyursolic acid, 2-β-hydroxyoleanolic acid, 3-O-acetyloleanolic acid, 3-O-acetylursolic acid, 6-methoxy-luteolin-7-glucoside, 6-methoxyluteolin, 6-methoxyluteolin-7-glucoside, methoxyluteolin-7-methylether, 7-ethoxy-rosmanol, 7-methoxy-rosmanol, alpha-amyrin, alpha-humulene, alpha-hydroxyhydrocaffeic acid, alpha-pinene, alpha-terpinene, alpha-terpinenyl acetate, alpha-terpineol, alpha-thujone, apigenin, apigenin-7-glucoside, curcumene, benzyl-alcohol, β-amyrenone, β-amyrin, β-elemene, β-pinene, betulin, betulinic acid, borneol, bornyl-acetate, caffeic acid, camphene, camphor, carnosic acid, carnosol, carvacrol, carvone, caryophyllene, caryophyllene-oxide, chlorogenic acid, diosmetin**, gamma-terpinene, hesperidin, isoborneol, limonene*, luteolin*, luteolin-3'-O-(3"-O-acetyl)-β-D-glucuronide, luteolin-3'-O-(4"-O-acetyl)-β-D-glucuronide, luteolin-3'-O-β-D-glucuronide, luteolin-7-glucoside, methyl-eugenol, myrcene, neo-chlorogenic acid, nepetin, octanoic acid, oleanolic acid, p-cymene, piperitenone, rosmanol, rosmaric acid, rosmaricine, rosmaridiphenol, rosemarinic acid, rosmarinol, rosmariquinone, sabinene, sabinyl acetate, salicylates, salicylic acid-2-β-D-glucoside, squalene, terpinen-4-ol, terpinolene, thymol, trans-anethole, trans-carveol, ursolic acid, verbenone, and zingiberene. Of the species listed, those containing at least one asterisk (*) are preferred and those containing two asterisks (**) are particularly preferred.

Triterpenes and Diterpene Lactones

Certain of preferred embodiments also include delivering an effective amount of a triterpene species or diterpene lactone species with the fraction isolated or derived from hops or tryptanthrin. Preferred triterpenes include oleanolic acid, and ursolic acid. Both ursolic and oleanolic acid are found in a wide variety of botanicals. Diterpene lactones, such as andrographolide, can be obtained from *Andrographis paniculata*.

Diterpene lactone species, such as andrographolide, and triterpenes, such as ursolic acid and oleanolic acid, are commonly found in plants and are used for their anti-inflammatory properties. The anti-inflammatory effects of these compounds have been described in the literature since 1960. Their mechanism of action is believed to be due (i) to the inhibition of histamine release from mast cells or (ii) to the inhibition of lipoxygenase and cyclooxygenase activity thereby reducing the synthesis of inflammatory factors produced during the arachidonic acid cascade. Since andrographolide and oleanolic acid have been found to promote the healing of stomach ulcers, it is unlikely that the cyclooxygenase activity that is inhibited is COX-1. Also, andrographolide and oleanolic acid are potent antioxidants, capable of inhibiting the generation of reactive oxygen intermediates and restoring tissue glutathione levels following stress.

For example, botanical sources for ursolic acid can be selected from the group consisting of *Adina piluifera, Agrimonia eupatoria, Arbutus unedo, Arctostaphylos uva-ursi, Artocarpus heterophyllus, Catalpa bignoniodes, Catharanthus roseus, Chimaphila umbellata, Cornus florida, Cornus officinalis, Crataegus cuneata, Crataegus laevigata, Crataegus pinnatifida, Cryptostegia grandifolia, Elaeagnus pungens, Eriobotrya japonica, Eucalyptus citriodora, Forsythia suspensa, Gaultheria fragrantissima, Glechoma hederacea, Hedyotis diffusa, Helichrysum angustifolium, Humulus lupulus, Hyssopus officinalis, Ilex paraguariensis, Lavandula angustifolia, Lavandula latifolia, Leonurus cardiaca, Ligustrum japonicum, Limonia acidissima, Lycopus europeus, Malus domestica, Marubium vulgare, Melaleuca leucadendra, Melissa officinalis, Mentha spicata, Menthaxrotundifolia, Monarda didyma, Nerium oleander, Ocimum basilicum, Ocimum basilicum, Ocimum basilicum, Ocimum baslicum, Ocimum canum, Origanum majorana, Origanum vulgare, Plantago asiatica, Plantago major, Plectranthus amboinicus, Prunell vulgaris, Prunella vulgaris, Prunus cerasus, Prunus laurocerasus, Prunus persica, Prunus serotina* spp *serotina, Psidium guajava, Punica granatum, Pyrus communis, Rhododendron dauricum, Rhododendron ferrugineum, Rhododendron ponticum, Rosmarinus officinalis, Rubus fruticosus, Salvia officinalis, Salvia sclarea, Salvia triloba, Sambucus nigra, Sanguisorba officinalis, Satureja hortensis, Satureja montana, Sorbus aucubaria, Syringa vulgaris, Teucrium chamaedrys Teucrium polium, Teucrium* spp, *Thevetia peruviana, Thymus serpyllum, Thymus vulgaris, Uncaria tomentosa, Vaccinium corymobosum, Vaccinium myrtillus, Vaccinium vitis idaea, Verbena officinalis, Viburnum opulus* var. *opulus, Viburnum prunifolium, Vinca minor* and *Zizyphus jujuba*.

Similarly, oleanolic acid is found in *Achyranthes aspera, Achyranthes bidentiata, Adina piluifera, Ajpocynum cannabinum, Akebia quinata, Allium cepa, Allium sativum, Arctostaphylos uva-ursi, Calendula officinalis, Catharanthus roseus, Centaurium erythraea, Chenopodium album, Citrullus colocynthis, Cnicus benedictus, Cornus officinalis, Crataegus pinnatifida Cyperus rotundus, Daemonorops draco, Diospyros kaki, Elaeagnus pungens, Eleutherococcus senticosus, Eriobotrya japonica, Eugenia caryophyllata, Forsythia suspensa, Glechoma hederacea, Harpagophtum procumbens, Hedera helix, Hedyotis diffusa, Helianthus annuus, Hemsleys amabilis, Humulus lupulus, Hyssopus officinalis, Ilex rotunda, Lavandula latifolia, Leonurus cardiaca, Ligustrum japonicum, Ligustrum lucidum, Liquidambar orientalis, Liquidambar styraciflua, Loranthus parasiticus, Luffa aegyptiaca, Melaleuca leucadendra, Melissa officinalis, Mentha spicata, Menthaxrotundifolia, Momordica cochinchinensis, Myristica fragrans, Myroxylon balsamum, Nerium oleander,*

Ocimum suave, Ociumum basilicum, Olea europaea, Origanum majorana, Origanum vulgare, Paederia scandens, Panax ginseng, Panax japonicus, Panax quinquefolius, Patrinia scabiosaefolia, Phytolacca americana, Plantago major, Plectranthus amboinicus, Prunella vulgaris, Prunus cerasus, Psidium guajava, Pulsatilla chinenisis, Quisqualis indica, Rosmarinus officinalis, Salvaia officinalis, Salvia sclarea, Salvia triloba, Sambucus nigra, Satureja hortensis, Satureja montana, Swertia chinensis, Swertia diluta, Swertia mileensis, Syzygium aromaticum, Thymus serpyllum, Thymus vulgaris, Trachycarpus fortunei, Uncaria tomentosa, Vaccinium corymbosum, Vaccinium myrtillus, Viburnum prunifolium, Viscum album, Vitis vinifera, or Zizyphus jujuba.

The preferred botanical sources for ursolic acid is a member selected from the group consisting of Ligustrum japonicum, Plantago asiatica, Plantago major, Prunus species, Uncaria tomentosa, Zizyphus jujuba, Cornus officinalis, Eucalyptus citriodora, Forsythia suspensa, Lavandula latifolia, Malus domestica, Nerium oleander, Ocimum baslicum, Punica granatum, Pyrus communis, Rosmarinus officinalis, Salvia triloba, Sorbus aucubaria, Vaccinium myrtillus, Vaccinium vitis-idaea, and Viburnum opulus var. opulus. The most preferred botanical sources for ursolic acid is a member selected from the group consisting of Ligustrum japonicum, Plantago asiatica, Plantago major, Prunus species, Uncaria tomentosa, and Zizyphus jujuba.

The preferred botanical source for oleanolic acid is a member selected from the group consisting of Eleutherococcus senticosus, Ligustrum japonicum, Ligustrum lucidum, Panax ginseng, Panax japonicus, Panax quinquefolius, Plantago major, Prunella vulgaris, Vitis vinifera, Zizyphus jujuba, Achyranthes bidentiata, Allium cepa, Allium sativum, Cornus officinalis, Daemonorops draco, Forsythia suspensa, Prunus cerasus, Quisqualis indica, Rosmarinus officinalis, Salvia triloba, Syzygium aromaticum, Thymus vulgaris, Uncaria tomentosa, Vaccinium corymbosum, and Vaccinium myrtillus. The most preferred botanical source for oleanolic acid is a member selected from the group consisting of Eleutherococcus senticosus, Ligustrum japonicum, Ligustrum lucidum, Panax ginseng, Panax japonicus, Panax quinquefolius, Plantago major, Prunella vulgaris Vitis vinifera and Zizyphus jujuba.

Figure 5:
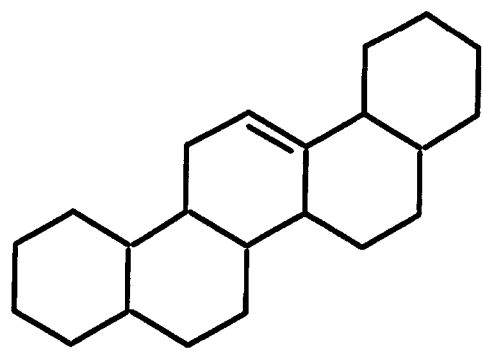
FIG. 5 illustrates the general chemical structures of the triterpene genus [A] and ursolic acid [B] and oleanolic acid [C] as a species within that genus.
Figure 5:
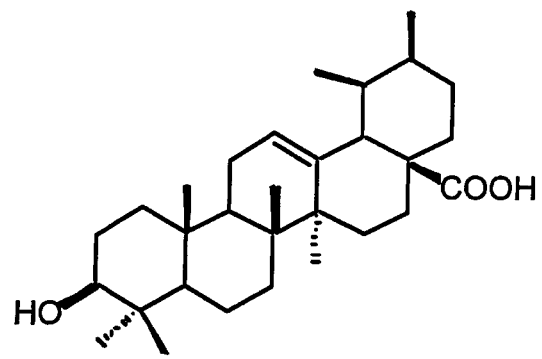
Figure 5:
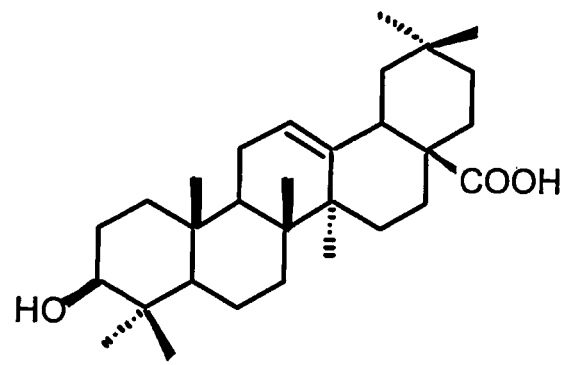

FIG. 5 illustrates the general chemical structures of the triterpene genus and ursolic acid and oleanolic acid as a species within that genus. Representative terpenoids within the genus are 18-a-glycyrrhetinic acid, 18-β-glycyrrhetinic acid, 2-a-3-a-dihydrooxyurs-12-3n-28-onic acid*, 3-a-hydroxyursolic acid*, 3-oxo-ursolic acid*, betulin, betulinic acid, celastrol*, eburicoic acid, friedelin*, glycyrrhizin, gypsogenin, oleanolic acid, oleanolic acid-3-acetate, pachymic acid, pinicolic acid, sophoradiol, soyasapogenol A, soyasapogenol B, tripterin, triptophenolide*, tumulosic acid, ursolic acid**, ursolic acid-3-acetate, uvaol*, and β-sitosterol. Of the species listed, those containing at least one asterisk (*) are preferred and those containing two asterisks (**) are particularly preferred.

Examples of diterpene lactone species include, but is not limited to, andrographolide, dehydroandrographolide, deoxyandrographolide, neoandrographolide, selenoandrographolide, homoandrographolide, andrographan, amdrographon, andrographosterin, 14-deoxy-11-oxoandrographolide, 14-deoxy-11,12-didehydroandrographolide, andrographiside, and edelin lactone.

Compositions and Synergistic Combinations

Preferred compositions can function to specifically inhibit COX-2 expression, to modulate NFκB, to inhibit prostaglandin synthesis selectively in target cells, or to inhibit inflammation response selectively in target cells. Preferred embodiments include compositions containing fractions or compounds isolated or derived from hops or compositions containing tryptanthrin and conjugates thereof.

A preferred embodiment comprises compositions containing fractions or compounds isolated or derived from hops. Examples of fractions isolated or derived from hops are alpha acids, isoalpha acids, reduced isoalpha acids, tetra-hydroisoalpha acids, hexa-hydroisoalpha acids, beta acids, and spent hops. Preferred compounds of the fractions isolated or derived from hops can be represented by a supragenus below:

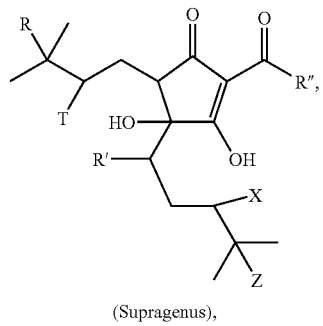

(Supragenus), wherein R' is selected from the group consisting of carbonyl, hydroxyl, OR, and OCOR, wherein R is alkyl; wherein R'' is selected from the group consisting of $CH(CH_3)$, $CH_2CH(CH_3)_2$, and $CH(CH_3)CH_2CH_3$; and wherein R, T, X, and Z are independently selected from the group consisting of H, F, Cl, Br, I and π orbital, with the proviso that if one of R, T, X, or Z is a π orbital, then the adjacent R, T, X, or Z is also a π orbital, thereby forming a double bond.

Other preferred compounds of the fractions isolated or derived from hops can be represented by a genus below:

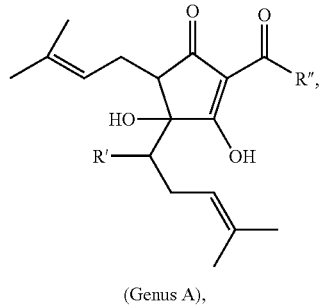

(Genus A), wherein R' is selected from the group consisting of carbonyl, hydroxyl, OR, and OCOR, wherein R is alkyl; and wherein R'' is selected from the group consisting of $CH(CH_3)_2$, $CH_2CH(CH_3)_2$, and $CH(CH_3)CH_2CH_3$.

Other preferred compounds of the fractions isolated or derived from hops can be represented by a genus below:

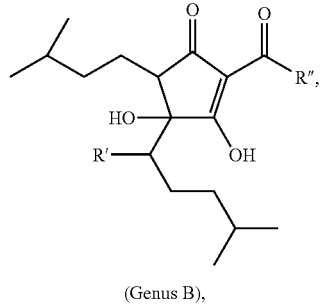

(Genus B), wherein R' is selected from the group consisting of carbonyl, hydroxyl, OR, and OCOR, wherein R is alkyl; and wherein R'' is selected from the group consisting of $CH(CH_3)_2$, $CH_2CH(CH_3)_2$, and $CH(CH_3)CH_2CH_3$.

Examples of preferred compounds of an ingredient isolated or derived from hops, include, but are not limited to, humulone, cohumulone, adhumulone, isohumulone, isocohumulone, isoadhumulone, dihydro-isohumulone, dihydro-isocohumulone, dihydro-adhumulone, tetrahydro-isohumulone, tetrahydro-isocohumulone, tetrahydro-adhumulone, hexahydro-isohumulone, hexahydro-isocohumulone, and hexahydro-adhumulone. The preferred compounds can bear substituents, as shown in the formula above.

Another embodiment comprises composition containing tryptanthrin and conjugates thereof.

Other embodiments relate to combinations of components. Preferred compositions can function to specifically inhibit COX-2 expression, to modulate NFκB, to inhibit prostaglandin synthesis selectively in target cells, or to inhibit inflammation response selectively in target cells, including synergistic effects.

One embodiment relates to compositions that include, as a first component, an active ingredient isolated or derived from an extract of hops and as a second component at least one member selected from the group consisting of rosemary, an extract or compound derived from rosemary, a triterpene species or derivatives or conjugates thereof, a diterpene lactone species or derivatives or conjugates thereof, and tryptanthrin or conjugates thereof. Another embodiment relates to compositions that include, as a first component, tryptanthrin or conjugates thereof and as a second component at least one member selected from the group consisting of an active ingredient isolated or derived from an extract of hops, rosemary, an extract or compound derived from rosemary, a triterpene species or derivatives or conjugates thereof, a diterpene lactone species or derivatives or conjugates thereof.

Dosage

The selected dosage level will depend upon activity of the particular composition, the route of administration, the severity of the condition being treated or prevented, and the condition and prior medical history of the patient being treated. However, it is within the skill of the art to start doses of the composition at levels lower than required to achieve the desired therapeutic effect and to gradually increase the dosage until the desired effect is achieved. If desired, the effective daily dose may be divided into multiple doses for purposes of administration, e.g., two to four separate doses per day. It will be understood, however, that the specific dose level for any particular patient will depend upon a variety of factors including body weight, general health, diet, time and route of administration, combination with other compositions and the severity of the particular condition being treated or prevented.

Preferred embodiments include delivering an effective amount of hops fractions, hops compounds, or hops derivatives alone or with in combination with other active ingredients. Preferably, a daily dose of preferred compositions would be formulated to deliver about 0.5 to 10,000 mg of alpha acid, isoalpha acid, reduced isoalpha acid, tetra-hydroisoalpha acid, hexa-hydroisoalpha acid, beta acid, or spent hops per day. More preferably, an effective daily dose of preferred compositions would be formulated to deliver about 50 to 7500 mg, about 100 to 5000 mg, about 200 to 3000 mg, or about 500 to 2000 mg of alpha acids, isoalpha acid, reduced isoalpha acid, tetra-hydroisoalpha acid, hexa-hydroisoalpha acid, beta acid, or spent hops per day. Preferably, the effective daily dose is administered once or twice a day. A certain embodiment provides a composition comprising about 0.5 to 800 mg of isoalpha acid or reduced isoalpha acid, more preferably about 50 to 400 mg or about 100 to 200 mg of isoalpha acid or reduced isoalpha acid per day. Another certain embodiment provides a composition comprising about 10 to 3000 mg of reduced isoalpha acid, tetra-hydroisoalpha acid, or hexa-hydroisoalpha acid per day, more preferably about 50 to 2000 mg, about 100 to 1500 mg, or about 200 to 1000 mg, of reduced isoalpha acid, tetra-hydroisoalpha acid, or hexa-hydroisoalpha acid per day. Yet another certain embodiment provides a composition comprising about 50 to 7500 mg of spent hops per day, preferably about 100 to 6000 mg, about 200 to 5000 mg, or about 500 to 3000 mg of spent hops per day.

Preferred embodiments include delivering an effective amount of tryptanthrin or conjugates thereof alone or with in combination with other active ingredients. Preferably, a daily dose of preferred compositions would be formulated to deliver about 0.0005 to 50 mg tryptanthrin/kg body weight per day. More preferably, an effective daily dose of preferred compositions would be formulated to deliver about 0.01 to 10 mg or about 0.1 to 5 mg tryptanthrin/kg body weight per day. Preferably, a daily dose of preferred compositions would be formulated to deliver about 0.035 to 3500 mg of tryptanthrin per day. More preferably, an effective daily dose of preferred composition would be formulated to deliver about 0.7 to 700 mg, about 1 to 500 mg or about 10 to 100 mg of tryptanthrin per day. Preferably, the effective daily dose is administered once or twice a day.

Preferred embodiments include delivering an effective amount of rosemary or an extract or compound derived from rosemary in combination with other active ingredients. Preferably, a daily dose of preferred compositions would be formulated to deliver about 0.5 to 5000 mg of rosemary, an extract of rosemary, or rosemary-derived compound per day. More preferably, an effective daily dose of preferred composition would be formulated to deliver about 5 to 2000 mg or about 100 to 1000 mg of rosemary, an extract of rosemary, or rosemary-derived compound per day. Preferably, the effective daily dose is administered once or twice a day. A certain embodiment provides a composition comprising about 75 mg of rosemary extract or rosemary-derived compound or derivative, to be administered once or twice a day.

Preferred embodiments include delivering an effective amount of a triterpene or diterpene lactone species or derivatives or conjugates thereof in combination with other active ingredients. Preferably, a daily dose of preferred compositions would be formulated to deliver about 0.0005 to 50 mg triterpene or diterpene lactone/kg body weight per day. More preferably, an effective daily dose of preferred compositions would be formulated to deliver about 0.01 to 10 mg or about 0.1 to 1 mg triterpene or diterpene lactone/kg body weight per day. Preferably, a daily dose of preferred compositions would be formulated to deliver about 0.035 to 3500 mg of triterpene or diterpene lactone species per day. More preferably, an effective daily dose of preferred composition would be formulated to deliver about 0.7 to 700 mg of triterpene or diterpene lactone species per day. Preferably, the effective daily dose is administered once or twice a day.

Preferably, an embodiment provides a composition containing an extract of rosemary and a triterpene, such as oleanolic acid, along with an active ingredient, such as a fraction isolated or derived from hops or tryptanthrin or conjugate thereof. Preferably, an embodiment provides a composition comprising about 0.01 to 500 mg of rosemary extract and about 0.01 to 500 mg of oleanolic acid. Preferably, an embodiment provides a composition capable of producing concentrations in target tissues of 0.1 to 10 μg/g tissue of rosemary extract and about 0.1 to 25 μg/g tissue of oleanolic acid.

A composition of preferred embodiments for topical application would contain about 0.001 to 10 weight percent, preferably about 0.1 to 1 weight percent of a hops extract component or derivative or tryptanthrin or conjugate thereof. Preferred embodiments would produce serum concentrations in the ranges of about 0.0001 to 10 µM, preferably about 0.01 to 1 µM of a fraction isolated or derived from hops or tryptanthrin or conjugate thereof. The preferred embodiments for topical application can further comprise an additional ingredient selected from rosemary, an extract or compound derived from rosemary, a triterpene species or derivatives or conjugates thereof a diterpene lactone species or derivatives or conjugates thereof, a fraction isolated or derived from hops or tryptanthrin or conjugates thereof at concentrations of each component of 0.001 to 10 weight percent, preferably 0.1 to 1 weight percent Preferred embodiments would produce serum concentrations in the ranges of about 0.001 to 50 µM, preferably about 0.1 µM to 5 µM of the additional ingredient.

A certain composition comprises a first component selected from a fraction isolated or derived from hops and a second component comprising an extract or compound derived from rosemary, an extract or compound derived from rosemary, a triterpene species or derivatives or conjugates thereof a diterpene lactone species or derivatives or conjugates thereof, or tryptanthrin or conjugates thereof. Preferably, the weight ratio of the first component, i.e. a fraction isolated or derived from hops to the second component, i.e. an extract or compound derived from rosemary, an extract or compound derived from rosemary, a triterpene species or derivatives or conjugates thereof, a diterpene lactone species or derivatives or conjugates thereof or tryptanthrin or conjugates thereof, is within a range of about 100:1 to about 1:100; preferably about 50:1 to about 1:50; more preferably about 10:1 to about 1:10.

A certain composition comprises a first component of tryptanthrin and conjugates thereof, and a second component comprising hops fraction, hops compound, hops derivative, rosemary, an extract or compound derived from rosemary, a triterpene species or derivatives or conjugates thereof, or a diterpene lactone species or derivatives or conjugates thereof. Preferably, the weight ratio of the first component, i.e. tryptanthrin and conjugates thereof, to the second component, i.e. hops fraction, hops compound, hops derivative, rosemary, an extract or compound derived from rosemary, a triterpene species or derivatives or conjugates thereof, or a diterpene lactone species or derivatives or conjugates thereof, is within a range of about 100:1 to about 1:100; preferably about 50:1 to about 1:50; more preferably about 10:1 to about 1:10; even more preferably about 1:1. It is understood that one skilled in art can readily use the amounts described above or appropriate intermediate amounts that are effective for a desired activity.

Applications of Preferred Compositions

As stated previously, the generally held concept (COX dogma) is that COX-1 is expressed constitutively in most tissues whereas COX-2 is the inducible enzyme triggered by pro-inflammatory stimuli including mitogens, cytokines and bacterial lipopolysaccharide (LPS) in cells in vitro and in inflamed sites in vivo. Based primarily on such differences in expression, COX-1 has been characterized as a housekeeping enzyme and is thought to be involved in maintaining physiological functions such as cytoprotection of the gastric mucosa, regulation of renal blood flow, and control of platelet aggregation. COX-2 is considered to mainly mediate inflammation, although constitutive expression is found in brain, kidney and the gastrointestinal tract. Therefore, it would be desirable to down-regulate expression of COX-2 tissue-specifically or cell-specifically. Such down-regulation can be achieved by modulating NFκB. Examples of target cells include, but are not limited to, inflammatory cells, pulmonary cells, microglia and tumor cells. Examples of nontarget cells include, but are not limited to, gastric mucosal, neural, and renal cells.

The compositions have widespread applications. Preferred compositions can be useful for treating conditions, such as cancer, autoimmune diseases, inflammatory diseases, neurological diseases. Preferred compositions are also believed to be useful for treating conditions, such as HIV-1 infections, rhinovirus infections, and cardiovascular diseases.

Preferred embodiments would be useful for, but not limited to a number of inflammatory conditions and can include conditions associated with tissue-specific activation of NFκB. Thus, the invention includes treatment of inflammation in a subject, and treatment of other inflammation-associated disorders, such as, as an analgesic in the treatment of pain and headaches, or as an antipyretic for the treatment of fever. Additional examples of such preferred embodiments would be useful to treat arthritis, including but not limited to rheumatoid arthritis, spondyloathopathies, gouty arthritis, osteoarthritis, systemic lupus erythematosis, and juvenile arthritis. Such preferred embodiments would be useful in the treatment of asthma, bronchitis, menstrual cramps, tendonitis, bursitis, and skin related conditions such as psoriasis, eczema, burns and dermatitis. Preferred embodiments also would be useful to treat gastrointestinal conditions such as inflammatory bowel disease, Crohn's disease, gastritis, irritable bowel syndrome and ulcerative colitis and for the prevention or treatment of cancer such as colorectal cancer. Preferred embodiments would be useful in treating inflammation in such diseases as vascular diseases, migraine headaches, periarteritis nodosa, thyroiditis, aplastic anemia, Hodgkin's disease, sclerodma, rheumatic fever, type I diabetes, myasthenia gravis, multiple sclerosis, sacoidosis, nephrotic syndrome, Behchet's syndrome, polymyositis, gingivitis, hypersensitivity, swelling occurring after injury, myocardial ischemia, periodontal disease, insulitis and the like.

Preferred embodiments would also be useful in the treatment of ophthalmic diseases, such as retinopathies, conjunctivitis, uveitis, ocular photophobia, and of acute injury to the eye tissue. Preferred embodiments would also be useful in the treatment of pulmonary inflammation, such as that associated with viral infections and cystic fibrosis. Preferred embodiments would also be useful in the treatment of asthma. Preferred embodiments would also be useful for the treatment of certain nervous system disorders such as cortical dementias including Alzheimer's disease. Preferred embodiments are useful as anti-inflammatory agents, such as for the treatment of arthritis, with the additional benefit of having significantly less harmful side effects. As inhibitors of COX-2 mediated biosynthesis of $PGE_2$, these compositions would also be useful in the treatment of allergic rhinitis, respiratory distress syndrome, endotoxin shock syndrome, atherosclerosis, and central nervous system damage resulting from stroke, ischemia and trauma. The preferred embodiments would also be useful for the treatment of fibromyalgia.

Since COX-2 can also play a role in the regulation of osteoblastic function, preferred embodiments can also be useful for treating and preventing osteoporosis. Kanematsu et al. (J Bone Miner Res 1997 November; 12(11):1789-96.) discloses that interleukin 1 (IL-1) and tumor necrosis factor alpha (TNF-alpha) have been implicated in the pathogenesis of osteoporosis. These proinflammatory cytokines induce both COX-2 and nitric oxide synthase (iNOS) with the release of $PGE_2$ and NO, respectively. They determined the interaction between COX and NOS pathways and their role in the regulation of osteoblastic function in MC3T3-E1 cells.

According to preferred embodiments, the animal may be a member selected from the group consisting of humans, non-human primates, dogs, cats, birds, horses, ruminants or other warm blooded animals. Preferred embodiments are directed primarily to the treatment of human beings. Administration can be by any method available to the skilled artisan, for example, by oral, topical, transdermal, transmucosal, or parenteral routes.

Besides being useful for human treatment, preferred embodiments are also useful for treatment of other animals, including horses, dogs, cats, birds, sheep, pigs, etc. A certain formulation for the treatment of inflammation would inhibit the induction and activity of COX-2 with little effect on the synthesis of $PGE_2$ in the gastric mucosa. Historically, the NSAIDs used for treatment of inflammation lacked the specificity of inhibiting COX-2 without affecting $PGE_2$ synthesis in gastric mucosal cells. Therefore, these drugs irritated and damaged the gastrointestinal system when used for extended periods.

Preferred compositions can also modulate NF-κB. Modulation of NF-κB can include regulating levels of NF-κB to treat or inhibit a pathological condition in a mammal. For example, abnormal levels, such as increased levels, of NF-κB can be associated with diseases and undesirable conditions. NF-κB is implicated in neuronal survival, inflammatory response, and cancer. NF-κB regulates COX-2 gene expression. Therefore, preferred compositions that modulate NF-κB can also affect the expression of COX-2.

Results presented herein indicate that modulation of NF-κB results in modulation of COX-2 expression in target cells only, without any significant direct inhibition of COX-2 or other enzymes with PG pathway. Therefore, for example, preferred compositions offer the advantage of anti-inflammatory effects without the side effects of damaging gastric mucosa, which are present in many existing NSAIDs. Existing NSAIDs, such as rofecoxib and celxobib, are supposed to inhibit the synthesis of prostanglandins by selectively inhibiting the COX-2 enzyme. However, side effects still occur with these existing NSAIDs because of lack of total selective inhibition of COX-2. Existing NSAIDs can still be promiscuous and affect enzymes other than COX-2 to result in side effects. By modulating NF-κB, compositions of preferred embodiments act at an upstream position and can inhibit the synthesis of COX-2 selectively in target cells. Without COX-2 in target cells, the synthesis of prostaglandins directed to inflammatory reactions can also be inhibited. Therefore, the inflammatory reaction can be prevented or halted. While COX-2 in target cells is affected, COX-1 and COX-2 in non-target cells remain unaffected and continues to maintain physiological functions, such as cytoprotection of gastric mucosa, regulation of renal blood flow, and control of platelet aggregation.

Since preferred compositions can affect NF-κB, preferred embodiments can also be useful for treating and preventing a variety of disorders including, but not limited to, autoimmune, inflammatory, neurological and cardiovascular diseases, and cancer.

Preferred embodiments can be useful for treating and preventing a pathological condition associated with tissue-specific activation of NF-κB. NF-κB can be found in numerous cell types and is found to be activated by a wide range of inducers. Upon activation and transport to the nuclei, NF-κB can initiate or regulate early-response gene transcription by binding to motifs found in the promoter or enhancer regions of specific genes.

The NF-κB response occurs in virtually all cell types in combination with a variety of co-activators. However, because NF-κB alone is not capable of activating its genes when bound to DNA, the exact genes activated will vary depending on the cellular context. Co-activators are believed to link enhancer-bound transcription factors, like NF-κB, to components of the basal transcription machinery, which then transcribe the gene to generate the mRNA copy. Therefore, NF-κB can be modulated tissue- or cell-specifically so as to treat and/or inhibit a variety of pathological conditions.

Therefore, compositions that inhibit or activate specific targets in the NF-κB pathway provide new approaches in the treatment or prevention of a number of serious diseases, including cancer and inflammatory disorders. NF-κB is a transcription factor that is involved in a range of cellular phenomena, including inflammation, antigen presentation, immunity, cytokine production, apoptosis and cancer. For example, as NF-κB affects pulmonary cells, a pathological condition can be manifested as asthma, and/or other pulmonary conditions. NF-κB is also involved in colorectal, mammary, and prostate conditions, such as cancer, as mediated by $PGE_2$. NF-κB is involved in these cancers and other cancers, as mediated by cell-to-cell adhesion. NF-κB is also involved in HIV-1 replication, colds, and flus. As stated above, NF-κB has been implicated in conditions, such as autoimmune, inflammatory, neurological and cardiovascular diseases, and cancer.

Formulations

Preferred compositions can be administered in the form of a dietary supplement or therapeutic composition. The compositions may be administered orally, topically, transdermally, transmucosally, parenterally, etc., in appropriate dosage units, as desired.

Preferred compositions for dietary application may include various additives such as other natural components of intermediary metabolism, vitamins and minerals, as well as inert ingredients such as talc and magnesium stearate that are standard excipients in the manufacture of tablets and capsules. For example, one embodiment comprises active ingredients of preferred compositions in combination with glucosamine or chondrotin sulfate.

As used herein, "pharmaceutically acceptable carrier" includes any and all solvents, dispersion media, coatings, isotonic and absorption delaying agents, sweeteners and the like. These pharmaceutically acceptable carriers may be prepared from a wide range of materials including, but not limited to, diluents, binders and adhesives, lubricants, disintegrants, coloring agents, bulking agents, flavoring agents, sweetening agents and miscellaneous materials such as buffers and absorbents that may be needed in order to prepare a particular therapeutic composition. The use of such media and agents for pharmaceutically active substances is well known in the art. Except insofar as any conventional media or agent is incompatible with the active ingredients, its use in preferred compositions is contemplated. In one embodiment, talc, and magnesium stearate are included in the formulation. Other ingredients known to affect the manufacture of this composition as a dietary bar or functional food can include flavorings, sugars, amino-sugars, proteins and/or modified starches, as well as fats and oils.

Dietary supplements, lotions or therapeutic compositions of preferred embodiments can be formulated in any manner known by one of skill in the art. In one embodiment, the composition is formulated into a capsule or tablet using techniques available to one of skill in the art. In capsule or tablet form, the recommended daily dose for an adult human or animal would preferably be contained in one to six capsules or tablets. However, preferred compositions can also be formulated in other convenient forms, such as an injectable solution or suspension, a spray solution or suspension, a lotion, gum, lozenge, food or snack item. Food, snack, gum or lozenge items can include any ingestible ingredient, including sweeteners, flavorings, oils, starches, proteins, fruits or fruit extracts, vegetables or vegetable extracts, grains, animal fats or proteins. Thus, preferred compositions can be formulated into cereals, snack items such as chips, bars, gumdrops, chewable candies or slowly dissolving lozenges. Preferred embodiments contemplate treatment of all types of inflammation-based diseases, both acute and chronic. Preferred formulations reduce the inflammatory response and thereby promotes healing of, or prevents further damage to, the affected tissue. A pharmaceutically acceptable carrier can also be used in the preferred compositions and formulations.

Assay Using AGS Cell Line

In order to identify selective COX-2 drugs, it has been common practice to use the Modified Whole Blood/Cell Assay of T. D. Warner et al., *Nonsteroid drug selectivities for cyclooxygenase-1 rather than cyclooxygenase-2 are associated with human gastrointestinal toxicity: A full in vitro analysis*, Proc. Natl. Sci. USA 96:7563-7568(1999). When hop fractions are tested according to this procedure, hops extracts do not yield $IC_{50}$ values in the necessary µg/mL range, since they are not direct inhibitors of COX-2. This lack of direct inhibition of COX-2 was demonstrated by Tobe, H. et al. 1997. (*Bone resorption Inhibitors from hop extract*. Biosci. Biotech. Biochem 61(1)158-159) using purified COX-2 enzyme. Similarly, EXAMPLE 4 of this application demonstrates that, when tested according to the Modified Whole Blood/Cell Assay, hops compounds and derivatives produce median inhibitory concentrations greater than 25 µg/mL. Such high median inhibitory concentrations are pharmacologically unsuitable. Therefore, the Modified Whole Blood Assay as described by Warner is an invalid procedure for formulating potentially therapeutically effective combinations containing hops or hops derivatives.

The discovery of COX-2 has made possible the design of drugs that reduce inflammation without removing the protective PGs in the stomach and kidney made by COX-1. One of our approaches is to screen compositions of the preferred embodiments using in vitro animal cells to assess COX-2 and COX-1 inhibitory activity employing $PGE_2$, which has cytoprotective actions and play a role in maintaining the integrity of the gastrointestinal mucosa, as an endpoint. Secondarily, different cell types are used to confirm results. The screening process would indicate compositions that have specific COX-2 activity and limited COX-1 inhibition. Compositions of preferred embodiments can be tested in two cell types: 1) human pulmonary cells or other cell line to determine and identify optimal amounts and ratios for compositions comprising more than one component; and 2) human gastric epithelial cells (AGS cell line), a gastrointestinal tract cell line and a model system for assessing toxicity which is typically related to inhibition of COX-1 which is required for wound healing (such as ulcers). Hence, compositions of preferred embodiments that can inhibit COX-2 or COX-2 induction can be screened by selecting compositions that have low or no activity in AGS cells and good activity in human pulmonary cells or other cell line.

In particular embodiments, the invention provides a composition comprising, as a first component, a fraction derived from hops; and as a second component, at least one member selected from the group consisting of rosemary, an extract derived from rosemary, a compound derived from rosemary, a triterpene species, a diterpene lactone species, and tryptanthrin. The fraction derived from hops can be extracted with $CO_2$. The fraction derived from hops can also be selected from the group consisting of isoalpha acids, reduced isoalpha acids, tetra-hydroisoalpha acids, hexa-hydroisoalpha acids, and spent hops.

In another embodiment, a composition of the invention can contain a fraction derived from hops comprising a compound of a supragenus having the formula:

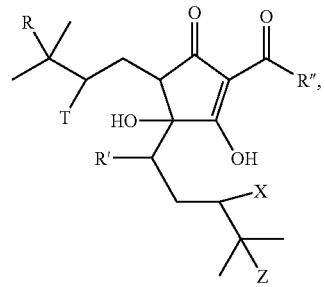

wherein R' is selected from the group consisting of carbonyl, hydroxyl, OR, and OCOR, wherein R is allyl;
wherein R" is selected from the group consisting of $CH(CH_3)_2$, $CH_2CH(CH_3)_2$, and $CH(CH_3)CH_2CH_3$; and
wherein R, T, X, and Z are independently selected from the group consisting of H, F, Cl, Br, I, and π orbital, with the proviso that if one of R, T, X, or Z is a π orbital, then the adjacent R, T, X, or Z is also a π orbital, thereby forming a double bond.

In yet another embodiment, the fraction derived from hops can comprise a compound of Genus A having the formula:

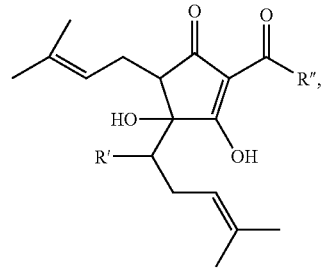

wherein R' is selected from the group consisting of carbonyl, hydroxyl, OR, and OCOR, wherein R is alkyl; and
wherein R" is selected from the group consisting of $CH(CH_3)_2$, $CH_2CH(CH_3)_2$, and $CH(CH_3)CH_2CH_3$.

In yet another embodiment, the fraction derived from hops can comprise a compound of Genus B having the formula:

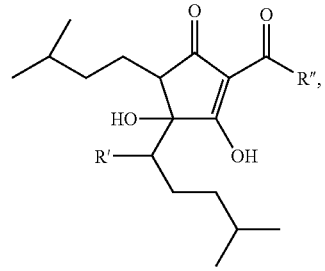

wherein R' is selected from the group consisting of carbonyl, hydroxyl, OR, and OCOR, wherein R is alkyl; and
wherein R" is selected from the group consisting of $CH(CH_3)_2$, $CH_2CH(CH_3)_2$, and $CH(CH_3)CH_2CH_3$.

In a composition of the invention, the fraction derived from hops can comprise a compound selected from the group consisting of cohumulone, adhumulone, isohumulone, isocohumulone, isoadhumulone, dihydro-isohumulone, dihydro-isocohumulone, dihydro-adhumulone, tetrahydro-isohumulone, tetrahydro-isocohumulone, tetrahydro-adhumulone, hexahydro-isohumulone, hexahydro-isocohumulone, and hexahydro-adhumulone.

In a composition of the invention, a second component can be a compound derived from rosemary that is selected from the group consisting of 1,8-cineole, 19-alpha-hydroxyursolic acid, 2-β-hydroxyoleanolic acid, 3-O-acetyloleanolic acid, 3-O-acetylursolic acid, 6-methoxy-luteolin-7-glucoside, 6-methoxyluteolin, 6-methoxyluteolin-7-glucoside, methoxyluteolin-7-methylether, 7-ethoxy-rosmanol, 7-methoxy-rosmanol, alpha-amyrin, alpha-humulene, alpha-hydroxyhydrocaffeic acid, alpha-pinene, alpha-terpinene, alpha-terpinenyl acetate, alpha-terpineol, alpha-thujone, apigenin, apigenin-7-glucoside, curcumene, benzyl-alcohol, β-amyrenone, β-amyrin, β-elemene, β-pinene, betulin, betulinic acid, borneol, bornyl-acetate, caffeic acid, camphene, camphor, carnosic acid, carnosol, carvacrol, carvone, caryophyllene, caryophyllene-oxide, chlorogenic acid, diosmetin, gamma-terpinene, hesperidin, isoborneol, limonene, luteolin, luteolin-3'-O-(3''-O-acetyl)-β-D-glucuronide, luteolin-3'-O-(4''-O-acetyl)-β-D-glucuronide, luteolin-3'-O-β-D-glucuronide, luteolin-7-glucoside, methyl-eugenol, myrcene, neo-chlorogenic acid, nepetin, octanoic acid, oleanolic acid, p-cymene, piperitenone, rosmanol, rosmaric acid, rosmaricine, rosmaridiphenol, rosemarinic acid, rosmarinol, rosmariquinone, sabinene, sabinyl acetate, salicylates, salicylic acid-2-β-D-glucoside, squalene, terpinen-4-ol, terpinolene, thymol, trans-anethole, trans-carveol, ursolic acid, verbenone, and zingiberene.

In another embodiment, the second component can be a compound derived from rosemary that is selected from the group consisting of betulin, betulinic acid, carnosic acid, carnosol, carvacrol, chlorogenic acid, diosmetin, limonene, and luteolin. In still a further embodiment, the second component can be a triterpene species that is selected from the group consisting of 18-a-glycyrrhetinic acid, 18-β-glycyrrhetinic acid, 2-a-3-a-dihydrooxyurs-12-3n-28-onic acid, 3-a-hydroxyursolic acid, 3-oxo-ursolic acid, betulin, betulinic acid, celastrol, eburicoic acid, friedelin, glycyrrhizin, gypsogenin, oleanolic acid, oleanolic acid-3-acetate, pachymic acid, pinicolic acid, sophoradiol, soyasapogenol A, soyasapogenol B, tripterin, triptophenolide, tumulosic acid, ursolic acid, ursolic acid-3-acetate, uvaol, and β-sitosterol. Furthermore, the second component can be a triterpene species that is selected from the group consisting of 18-a-glycyrrhetinic acid, 18-β-glycyrrhetinic acid, 2-a-3-a-dihydrooxyurs-12-3n-28-onic acid, 3-a-hydroxyursolic acid, 3-oxo-ursolic acid, betulin, betulinic acid, celastrol, friedelin, oleanolic acid, tripterin, triptophenolide, ursolic acid, and uvaol. In addition, the second component can be tryptanthrin, a triterpene species, or a diterpene lactone species that is conjugated to a member selected from the group consisting of mono- or disaccharides, amino acids, sulfates, succinate, acetate, and glutathione.

A composition of the invention can also comprise about 0.5 to 10000 mg of the fraction isolated or derived from hops or about 50 to 7500 mg of the fraction isolated or derived from hops. A composition of the invention can additionally comprise about 0.035 to 3500 mg of tryptanthrin, or about 0.7 to 700 mg of tryptanthrin, wherein the second component is tryptanthrin. A composition of the invention can also comprise about 0.5 to 5000 mg of the second component, or about 5 to 2000 mg of the second component, wherein the second component is selected from the group consisting of rosemary, extract derived from rosemary, and a compound derived from rosemary. Additionally, a composition of the invention can comprise about 0.035 to 3500 mg of a triterpene species, or about 0.7 to 700 mg of a triterpene species, wherein the second component is a triterpene species.

In still another embodiment, a composition can comprise about 0.001 to 10 weight percent of the first component, or about 0.1 to 1 weight percent of the first component. In addition, a composition can comprise about 0.001 to 10 weight percent of the second component, or about 0.1 to 1 weight percent of the second component. In a composition of the invention, the ratio of the first component to the second component can be in the range of about 100:1 to about 1:100, or about 50:1 to about 1:50. Any of the compositions of the invention can further comprise a pharmaceutically acceptable carrier, and such a composition comprising a pharmaceutically acceptable carrier can be used in the methods of the invention.

The invention also provides a composition comprising as a first component, a fraction isolated or derived from hops; and as a second component, at least one member selected from the group consisting of rosemary, an extract derived from rosemary, a compound derived from rosemary, and tryptanthrin. The fraction isolated or derived from hops can be extracted with $CO_2$. The fraction isolated or derived from hops can be selected from the group consisting of alpha acids, isoalpha acids, reduced isoalpha acids, tetra-hydroisoalpha acids, hexa-hydroisoalpha acids, beta acids, and spent hops.

The fraction isolated or derived from hops can comprise a compound of a supragenus having the formula:

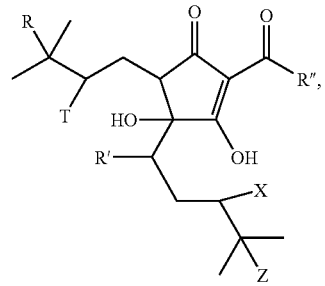

wherein R' is selected from the group consisting of carbonyl, hydroxyl, OR, and OCOR, wherein R is alkyl;

wherein R'' is selected from the group consisting of $CH(CH_3)_2$, $CH_2CH(CH_3)_2$, and $CH(CH_3)CH_2CH_3$; and wherein R, T, X, and Z are independently selected from the group consisting of H, F, Cl, Br, I, and π orbital, with the proviso that if one of R, T, X or Z is a π orbital, then the adjacent R, T, X, or Z is also a π orbital, thereby forming a double bond.

The fraction isolated or derived from hops can also comprise a compound of Genus A having the formula:

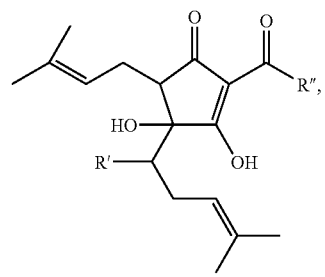

wherein R' is selected from the group consisting of carbonyl, hydroxyl, OR, and OCOR, wherein R is alkyl; and wherein R" is selected from the group consisting of CH(CH₃)₂, CH₂CH(CH₃)₂, and CH(CH₃)CH₂CH₃.

The fraction isolated or derived from hops can additionally comprise a compound of Genus B having the formula:

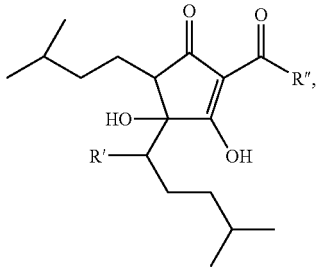

wherein R' is selected from the group consisting of carbonyl, hydroxyl, OR, and OCOR, wherein R is alkyl; and
wherein R" is selected from the group consisting of CH(CH₃)₂, CH₂CH(CH₃)₂, and CH(CH₃)CH₂CH₃.

The fraction isolated or derived from hops can additionally comprise a compound selected from the group consisting of humulone, cohumulone, adhumulone, isohumulone, isocohumulone, isoadhumulone, dihydro-isohumulone, dihydro-isocohumulone, dihydro-adhumulone, tetrahydro-isohumulone, tetrahydro-isocohumulone, tetrahydro-adhumulone, hexahydro-isohumulone, hexahydro-isocohumulone, and hexahydro-adhumulone.

Furthermore, the second component of such a composition can be a compound derived from rosemary that is selected from the group consisting of 1,8-cineole, 19-alpha-hydroxyursolic acid, 2-β-hydroxyoleanolic acid, 3-O-acetyloleanolic acid, 3-O-acetylursolic acid, 6-methoxy-luteolin-7-glucoside, 6-methoxyluteolin, 6-methoxyluteolin-7-glucoside, methoxyluteolin-7-methylether, 7-ethoxy-rosmanol, 7-methoxy-rosmanol, alpha-amyrin, alpha-humulene, alpha-hydroxyhydrocaffeic acid, alpha-pinene, alpha-terpinene, alpha-terpinenyl acetate, alpha-terpineol, alpha-thujone, apigenin, apigenin-7-glucoside, curcumene, benzyl-alcohol, β-amyrenone, β-amyrin, β-elemene, β-pinene, betulin, betulinic acid, borneol, bornyl-acetate, caffeic acid, camphene, camphor, carnosic acid, carnosol, carvacrol, carvone, caryophyllene, caryophyllene-oxide, chlorogenic acid, diosmetin, gamma-terpinene, hesperidin, isoborneol, limonene, luteolin, luteolin-3'-O-(3"-O-acetyl)-β-D-glucuronide, luteolin-3'-O-(4"-O-acetyl)-β-D-glucuronide, luteolin-3'-β-D-glucuronide, luteolin-7-glucoside, methyl-eugenol, myrcene, neochlorogenic acid, nepetin, octanoic acid, oleanolic acid, p-cymene, piperitenone, rosmanol, rosmaric acid, rosmaricine, rosmaridiphenol, rosemarinic acid, rosmarinol, rosmariquinone, sabinene, sabinyl acetate, salicylates, salicylic acid-2-β-D-glucoside, squalene, terpinen-4-ol, terpinolene, thymol, trans-anethole, trans-carveol, ursolic acid, verbenone, and zingiberene. The second component can also be a compound derived from rosemary that is selected from the group consisting of betulin, betulinic acid, carnosic acid, carnosol, carvacrol, chlorogenic acid, diosmetin, limonene, and luteolin. Additionally, the second component can be tryptanthrin that is conjugated to a member selected from the group consisting of mono- or di-saccharides, amino acids, sulfates, succinate, acetate, and glutathione.

In a particular embodiment, the composition can comprise about 0.5 to 10000 mg or about 50 to 7500 mg of the fraction isolated or derived from hops. In addition, the composition can comprise about 0.35 to 3500 mg of tryptanthrin, or about 0.7 to 700 mg of tryptanthrin, wherein the second component is tryptanthrin. Moreover, the composition can comprise about 0.5 to 5000 mg of the second component, or about 5 to 2000 mg of the second component, wherein the second component is selected from the group consisting of rosemary, extract derived from rosemary, and a compound derived from rosemary. In addition, the composition can comprise about 0.001 to 10 weight percent of the first component, or about 0.1 to 1 weight percent of the first component. Also, the composition can comprise about 0.001 to 10 weight percent of the second component, about 0.1 to 1 weight percent of the second component. In another embodiment, a ratio of the first component to the second component can be in the range of about 100:1 to about 1:100, or in the range of about 50:1 to about 1:50. The composition can further comprise a pharmaceutically acceptable carrier.

In still another embodiment, the invention provides a method of modulating inflammatory response in cells, the method comprising contacting the cells with a composition of the invention. For example, the method can be carried out using a composition comprising a fraction isolated or derived from hops and a second component selected from the group consisting of rosemary, an extract derived from rosemary, a compound derived from rosemary, a triterpene species, a diterpene lactone species, and tryptanthrin. The invention also provides a method of treating or inhibiting a pathological condition in a mammal associated with tissue-specific activation of inflammation, the method comprising administering to the mammal a composition comprising a fraction isolated or derived from hops and a second component selected from the group consisting of rosemary, an extract derived from rosemary, a compound derived from rosemary, a triterpene species, a diterpene lactone species, and tryptanthrin.

In such a method of treating or inhibiting a pathological condition, the composition can contain a fraction isolated or derived from hops can be selected from the group consisting of alpha acids, isoalpha acids, reduced isoalpha acids, tetrahydroisoalpha acids, hexa-hydroisoalpha acids, beta acids, and spent hops. In another embodiment of the method, the fraction isolated or derived from hops comprises a compound of a supragenus having the formula:

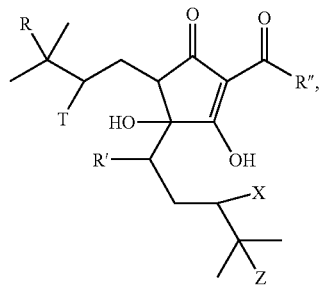

wherein R' is selected from the group consisting of carbonyl, hydroxyl, OR, and OCOR, wherein R is alkyl;
wherein R" is selected from the group consisting of CH(CH₃)₂, CH₂CH(CH₃)₂, and CH(CH₃)CH₂CH₃; and
wherein R, T, X, and Z are independently selected from the group consisting of H, F, Cl, Br, L and π orbital, with the proviso that if one of R, T, X, or Z is a π orbital, then the adjacent R, T, X, or Z is also a π orbital, thereby forming a double bond.

In the method, the fraction isolated or derived from hops can also comprise a compound of Genus A having the formula:

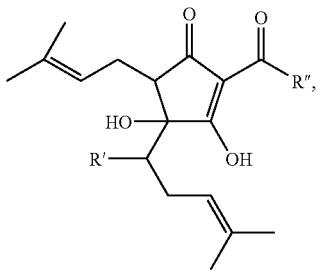

wherein R' is selected from the group consisting of carbonyl, hydroxyl, OR, and OCOR, wherein R is alkyl; and wherein R" is selected from the group consisting of $CH(CH_3)_2$, $CH_2CH(CH_3)_2$, and $CH(CH_3)CH_2CH_3$.

In yet another embodiment of the method, the fraction isolated or derived from hops can additionally comprise a compound of Genus B having the formula:

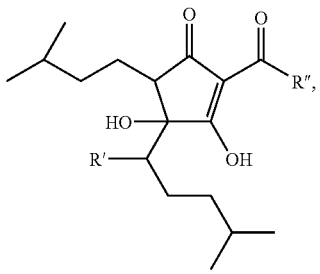

wherein R' is selected from the group consisting of carbonyl, hydroxyl, OR, and OCOR, wherein R is alkyl; and wherein R" is selected from the group consisting of $CH(CH_3)_2$, $CH_2CH(CH_3)_2$, and $CH(CH_3)CH_2CH_3$.

In still another embodiment of the method, the fraction isolated or derived from hops comprises a compound selected from the group consisting of humulone, cohumulone, adhumulone, isohumulone, isocohumulone, isoadhumulone, dihydro-isohumulone, dihydro-isocohumulone, dihydro-adhumulone, tetrahydro-isohumulone, tetrahydro-isocohumulone, tetrahydro-adhumulone, hexahydro-isohumulone, hexahydro-isocohumulone, and hexahydro-adhumulone. In a particular embodiment, the composition can comprise about 0.5 to 10000 mg or about 50 to 7500 mg of the fraction isolated or derived from hops. Furthermore, the composition can comprise about 0.001 to 10 weight percent or about 0.1 to 1 weight percent of the fraction isolated or derived from hops. In a particular embodiment, the second component is rosemary. In another embodiment the second component is an extract derived from rosemary. In still another embodiment, the second component is a triterpene species. In a method of the invention, the composition can further comprise a third component different from the second component, where the third component is selected from the group consisting of rosemary, an extract derived from rosemary, a compound derived from rosemary, a triterpene species, a diterpene lactone species, and tryptanthrin. In a particular embodiment, the second and third components are an extract derived from rosemary and tryptanthrin, respectively.

In another embodiment of the method, the second component can be a compound derived from rosemary that is selected from the group consisting of 1,8-cineole, 19-alpha-hydroxyursolic acid, 2-β-hydroxyoleanolic acid, 3-O-acetyloleanolic acid, 3-O-acetylursolic acid, 6-methoxy-luteolin-7-glucoside, 6-methoxyluteolin, 6-methoxyluteolin-7-glucoside, methoxyluteolin-7-methylether, 7-ethoxy-rosmanol, 7-methoxy-rosmanol, alpha-amyrin, alpha-humulene, alpha-hydroxyhydrocaffeic acid, alpha-pinene, alpha-terpinene, alpha-terpinenyl acetate, alpha-terpineol, alpha-thujone, apigenin, apigenin-7-glucoside, curcumene, benzyl-alcohol, β-amyrenone, β-amyrin, β-elemene, β-pinene, betulin, betulinic acid, borneol, bornyl-acetate, caffeic acid, camphene, camphor, carnosic acid, carnosol, carvacrol, carvone, caryophyllene, caryophyllene-oxide, chlorogenic acid, diosmetin, gamma-terpinene, hesperidin, isoborneol, limonene, luteolin, luteolin-3'-O-(3"-O-acetyl)-β-D-glucuronide, luteolin-3'-O-(4"-O-acetyl)-β-D-glucuronide, luteolin-3'-O-β-D-glucuronide, luteolin-7-glucoside, methyl-eugenol, myrcene, neo-chlorogenic acid, nepetin, octanoic acid, oleanolic acid, p-cymene, piperitenone, rosmanol, rosmaric acid, rosmaricine, rosmaridiphenol, rosemarinic acid, rosmarinol, rosmariquinone, sabinene, sabinyl acetate, salicylates, salicylic acid-2-β-D-glucoside, squalene, terpinen-4-ol, terpinolene, thymol, trans-anethole, trans-carveol, ursolic acid, verbenone, and zingiberene.

In such a method of the invention, the second component can also be a compound derived from rosemary that is selected from the group consisting of betulin, betulinic acid, carnosic acid, carnosol, carvacrol, chlorogenic acid, diosmetin, limonene, and luteolin. The composition used in the method can comprise about 0.5 to 5000 mg of the second component, or about 5 to 2000 mg of the second component, wherein the second component is selected from the group consisting of rosemary, extract derived from rosemary, and a compound derived from rosemary. In still another embodiment, the second component used in a method of the invention can be a triterpene species or a diterpene lactone species that is conjugated to a member selected from the group consisting of mono- or di-saccharides, amino acids, sulfates, succinate, acetate, and glutathione.

In yet another embodiment of a method of the invention, the second component can be a triterpene species that is selected from the group consisting of 18-a-glycyrrhetinic acid, 18-β-glycyrrhetinic acid, 2-a-3-a-dihydrooxyurs-12-3n-28-onic acid, 3-a-hydroxyursolic acid, 3-oxo-ursolic acid, betulin, betulinic acid, celastrol, eburicoic acid, friedelin, glycyrrhizin, gypsogenin, oleanolic acid, oleanolic acid-3-acetate, pachymic acid, pinicolic acid, sophoradiol, soyasapogenol A, soyasapogenol B, tripterin, triptophenolide, tumulosic acid, ursolic acid, ursolic acid-3-acetate, uvaol, and β-sitosterol. In addition, the second component can be a triterpene species that is selected from the group consisting of 18-a-glycyrrhetinic acid, 18-β-glycyrrhetinic acid, 2-a-3-a-dihydrooxyurs-12-3n-28-onic acid, 3-a-hydroxyursolic acid, 3-oxo-ursolic acid, betulin, betulinic acid, celastrol, friedelin, oleanolic acid, tripterin, triptophenolide, ursolic acid, and uvaol.

In a particular embodiment of a method of the invention, the composition can comprise about 0.035 to 3500 mg of a triterpene species or about 0.7 to 700 mg of a triterpene species, wherein the second component is a triterpene species. In another embodiment of the method, the second component is tryptanthrin that is conjugated to a member selected from the group consisting of mono- or di-saccharides, amino acids, sulfates, succinate, acetate, and glutathione. In still another embodiment of a method of the invention, the composition can comprise about 0.035 to 3500 mg of tryptanthrin, or about 0.7 to 700 mg of tryptanthrin, wherein the second component is tryptanthrin. In addition, the composition used in a method can comprise about 0.001 to 10 weight percent of the second component or about 0.1 to 1 weight percent of the second component. Furthermore, a ratio of the first component to the second component can be in the range of about 100:1 to about 1:100 or in the range of about 50:1 to about 1:50.

In such a method of treating or inhibiting a pathological condition, the pathological condition can be selected from the group consisting of autoimmune diseases, inflammatory diseases, neurological diseases, and cancer. In addition, the pathological condition can be selected from the group consisting of inflammation, inflammation-associated disorders, arthritis, asthma, bronchitis, menstrual cramps, tendonitis, bursitis, skin-related conditions, gastrointestinal conditions, cancer, ophthalmic diseases, pulmonary inflammation, nervous system disorders, allergic rhinitis, respiratory distress syndrome, endotoxin shock syndrome, atherosclerosis, and central nervous damage. In methods of the invention, the composition can be administered in a variety of ways, including orally, topically, parenterally, or rectally.

The invention further provides a method of modulating the amount of cyclooxygenase-2 (COX-2) activity in target cells without substantially modulating COX-2 activity in non-target cells, the method comprising contacting the cells with a composition comprising a fraction isolated or derived from hops and a second component selected from the group consisting of rosemary, an extract derived from rosemary, a compound derived from rosemary, a triterpene species, a diterpene lactone species, and tryptanthrin. In such a method of the invention, the non-target cells can also be contacted with a fraction isolated or derived from hops. The contacting step can be performed in vivo. In a method of the invention, the COX-2 activity can be modulated by inhibition of the COX-2 gene.

Additionally, the invention provides a method of treating or inhibiting a pathological condition in a mammal involving inhibiting inducibility or activity of cyclooxygenase-2 (COX-2), the method comprising administering to the mammal a composition comprising a fraction isolated or derived from hops and a second component selected from the group consisting of rosemary, an extract derived from rosemary, a compound derived from rosemary, a triterpene species, a diterpene lactone, and tryptanthrin. In such a method of the invention, the fraction isolated or derived from hops can be selected from the group consisting of alpha acids, isoalpha acids, reduced isoalpha acids, tetra-hydroisoalpha acids, hexa-hydroisoalpha acids, beta acids, and spent hops.

If desired in such a method of the invention, the fraction isolated or derived from hops comprises a compound of a supragenus having the formula:

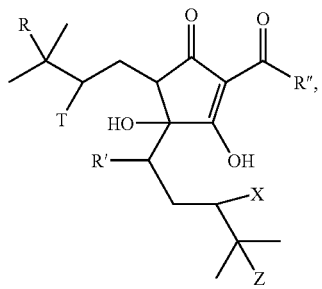

wherein R' is selected from the group consisting of carbonyl, hydroxyl, OR, and OCOR, wherein R is alkyl;
wherein R" is selected from the group consisting of $CH(CH_3)_2$, $CH_2CH(CH_3)_2$, and $CH(CH_3)CH_2CH_3$; and wherein R, T, X, and Z are independently selected from the group consisting of H, F, Cl, Br, I, and π orbital, with the proviso that if one of R, T, X, or Z is a π orbital, then the adjacent R, T, X, or Z is also a π orbital, thereby forming a double bond.

In such a method of the invention, the fraction isolated or derived from hops can also comprise a compound of Genus A having the formula:

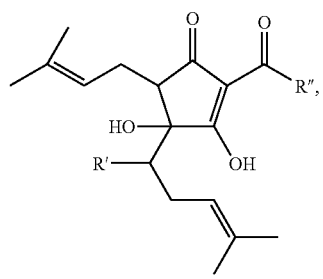

wherein R' is selected from the group consisting of carbonyl, hydroxyl, OR, and OCOR, wherein R is alkyl; and
wherein R" is selected from the group consisting of $CH(CH_3)_2$, $CH_2CH(CH_3)_2$, and $CH(CH_3)CH_2CH_3$.

In such a method of the invention, the fraction isolated or derived from hops can also comprise a compound of Genus B having the formula:

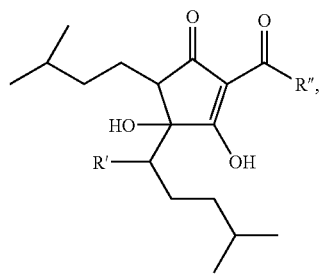

wherein R' is selected from the group consisting of carbonyl, hydroxyl, OR, and OCOR, wherein R is alkyl; and
wherein R" is selected from the group consisting of $CH(CH_3)_2$, $CH_2CH(CH_3)_2$, and $CH(CH_3)CH_2CH_3$.

In such a method of the invention, the fraction isolated or derived from hops can comprise a compound selected from the group consisting of humulone, cohumulone, adhumulone, isohumulone, isocohumulone, isoadhumulone, dihydro-isohumulone, dihydro-isocohumulone, dihydro-adhumulone, tetrahydro-isohumulone, tetrahydro-isocohumulone, tetrahydro-adhumulone, hexahydro-isohumulone, hexahydro-isocohumulone, and hexahydro-adhumulone. In addition, the second component can be an extract derived from rosemary. Furthermore, the second component can be a triterpene species.

In another embodiment of a method of the invention, the composition further can comprise a third component different from the second component, the third component being selected from the group consisting of rosemary, an extract derived from rosemary, a compound derived from rosemary, a triterpene species, a diterpene lactone, and tryptanthrin. In a particular embodiment, the second and third components are an extract derived from rosemary and tryptanthrin, respectively.

In yet another embodiment of such a method of the invention, the second component is a compound derived from rosemary that is selected from the group consisting of 1,8-cineole, 19-alpha-hydroxyursolic acid, 2-β-hydroxyoleanolic acid, 3-O-acetyloleanolic acid, 3-O-acetylursolic acid, 6-methoxy-luteolin-7-glucoside, 6-methoxyluteolin, 6-methoxyluteolin-7-glucoside, methoxyluteolin-7-methylether, 7-ethoxy-rosmanol, 7-methoxy-rosmanol, alpha-amyrin, alpha-humulene, alpha-hydroxyhydrocaffeic acid, alpha-pinene, alpha-terpinene, alpha-terpinenyl acetate, alpha-terpineol, alpha-thujone, apigenin, apigenin-7-glucoside, curcumene, benzyl-alcohol, β-amyrenone, β-amyrin, β-elemene, β-pinene, betulin, betulinic acid, borneol, bornyl-acetate, caffeic acid, camphene, camphor, carnosic acid, carnosol, carvacrol, carvone, caryophyllene, caryophyllene-oxide, chlorogenic acid, diosmetin, gamma-terpinene, hesperidin, isoborneol, limonene, luteolin, luteolin-3'-O-(3"-O-acetyl)-β-D-glucuronide, luteolin-3'-O-(4"-O-acetyl)-β-D-glucuronide, luteolin-3'-O-β-D-glucuronide, luteolin-7-glucoside, methyl-eugenol, myrcene, neo-chlorogenic acid, nepetin, octanoic acid, oleanolic acid, p-cymene, piperitenone, rosmanol, rosmaric acid, rosmaricine, rosmaridiphenol, rosemarinic acid, rosmarinol, rosmariquinone, sabinene, sabinyl acetate, salicylates, salicylic acid-2-β-D-glucoside, squalene, terpinen-4-ol, terpinolene, thymol, trans-anethole, trans-carveol, ursolic acid, verbenone, and zingiberene.

In another embodiment of such a method of the invention, the second component can be a triterpene species or a diterpene lactone species that is conjugated to a member selected from the group consisting of mono- or di-saccharides, amino acids, sulfates, succinate, acetate, and glutathione. Additionally, the second component can be a triterpene species that is selected from the group consisting of 18-a-glycyrrhetinic acid, 18-β-glycyrrhetinic acid, 2-a-3-a-dihydrooxyurs-12-3n-28-onic acid, 3-a-hydroxyursolic acid, 3-oxo-ursolic acid, betulin, betulinic acid, celastrol, eburicoic acid, friedelin, glycyrrhizin, gypsogenin, oleanolic acid, oleanolic acid-3-acetate, pachymic acid, pinicolic acid, sophoradiol, soyasapogenol A, soyasapogenol B, tripterin, triptophenolide, tumulosic acid, ursolic acid, ursolic acid-3-acetate, uvaol, and β-sitosterol. Also, the second component can be tryptanthrin that is conjugated to a member selected from the group consisting of mono- or di-saccharides, amino acids, sulfates, succinate, acetate, and glutathione. If desired in such a method of the invention, a ratio of the first component to the second component can be in the range of about 100:1 to about 1:100 or in the range of about 50:1 to about 1:50.

In a particular embodiment of a method of the invention, the pathological condition involving inhibiting inducibility or activity of COX-2 can be selected from the group consisting of inflammation, inflammation-associated disorders, arthritis, asthma, bronchitis, menstrual cramps, tendonitis, bursitis, skin-related conditions, gastrointestinal conditions, cancer, ophthalmic diseases, pulmonary inflammation, nervous system disorders, allergic rhinitis, respiratory distress syndrome, endotoxin shock syndrome, atherosclerosis, and central nervous damage.

Also, the invention provides a method of inhibiting prostaglandin synthesis selectively in target cells, the method comprising contacting the cells with a fraction isolated or derived from hops and a second component selected from the group consisting of rosemary, an extract derived from rosemary, a compound derived from rosemary, a triterpene species, a diterpene lactone, and tryptanthrin. In such a method of the invention, the fraction isolated or derived from hops can be selected from the group consisting of alpha acids, isoalpha acids, reduced isoalpha acids, tetra-hydroisoalpha acids, hexa-hydroisoalpha acids, beta acids, and spent hops.

In addition in such a method of the invention, the fraction isolated or derived from hops can comprise a compound of a supragenus having the formula:

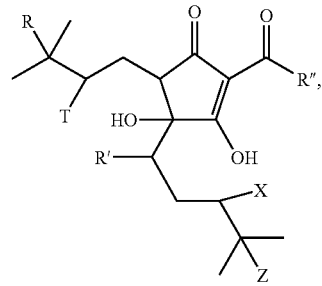

wherein R' is selected from the group consisting of carbonyl, hydroxyl, OR, and OCOR, wherein R is alkyl;
wherein R" is selected from the group consisting of $CH(CH_3)_2$, $CH_2CH(CH_3)_2$, and $CH(CH_3)CH_2CH_3$; and
wherein R, T, X, and Z are independently selected from the group consisting of H, F, Cl, Br, I, and π orbital, with the proviso that if one of R, T, X, or Z is a π orbital, then the adjacent R, T, X, or Z is also a π orbital, thereby forming a double bond.

In another embodiment of the method of the invention, the fraction isolated or derived from hops can comprise a compound of Genus A having the formula:

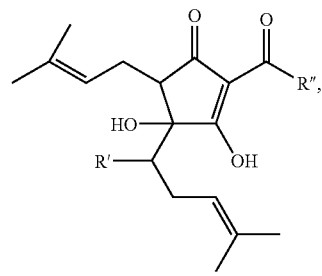

wherein R' is selected from the group consisting of carbonyl, hydroxyl, OR, and OCOR, wherein R is alkyl; and
wherein R" is selected from the group consisting of $CH(CH_3)_2$, $CH_2CH(CH_3)_2$, and $CH(CH_3)CH_2CH_3$.

In still another embodiment of such a method of the invention, the fraction isolated or derived from hops comprises a compound of Genus B having the formula:

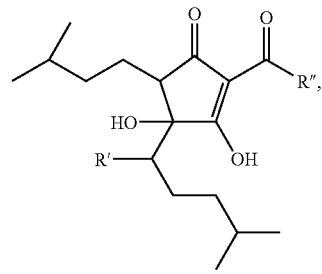

wherein R' is selected from the group consisting of carbonyl, hydroxyl, OR, and OCOR, wherein R is alkyl; and wherein R" is selected from the group consisting of CH(CH$_3$)$_2$, CH$_2$CH(CH$_3$)$_2$, and CH(CH$_3$)CH$_2$CH$_3$.

In another embodiment of such a method of the invention, the fraction isolated or derived from hops can comprise a compound selected from the group consisting of humulone, cohumulone, adhumulone, isohumulone, isocohumulone, isoadhumulone, dihydro-isohumulone, dihydro-isocohumulone, dihydro-adhumulone, tetrahydro-isohumulone, tetrahydro-isocohumulone, tetrahydro-adhumulone, hexahydro-isohumulone, hexahydro-isocohumulone, and hexahydro-adhumulone.

In a further embodiment, the invention provides a method of inhibiting an inflammatory response selectively in target cells, the method comprising contacting the cells with a fraction isolated or derived from hops and a second component selected from the group consisting of rosemary, an extract derived from rosemary, a compound derived from rosemary, a triterpene species, a diterpene lactone, and tryptanthrin. In such a method, the fraction isolated or derived from hops can be selected from the group consisting of alpha acids, isoalpha acids, reduced isoalpha acids, tetra-hydroisoalpha acids, hexa-hydroisoalpha acids, beta acids, and spent hops.

In such a method, the fraction isolated or derived from hops can comprise a compound of a supragenus having the formula:

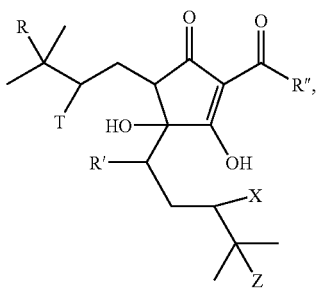

wherein R' is selected from the group consisting of carbonyl, hydroxyl, OR, and OCOR, wherein R is alkyl;
wherein R" is selected from the group consisting of CH(CH$_3$)$_2$, CH$_2$CH(CH$_3$)$_2$, and CH(CH$_3$)CH$_2$CH$_3$; and
wherein R, T, X, and Z are independently selected from the group consisting of H, F, Cl, Br, I, and π orbital, with the proviso that if one of R, T, X, or Z is a π orbital, then the adjacent R, T, X, or Z is also a π orbital, thereby forming a double bond.

In another embodiment of such a method, the fraction isolated or derived from hops can comprise a compound of Genus A having the formula:

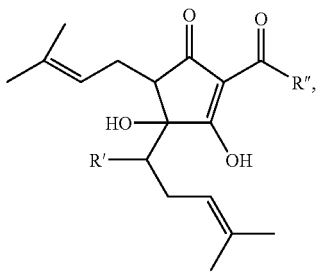

wherein R' is selected from the group consisting of carbonyl, hydroxyl, OR, and OCOR, wherein R is alkyl; and
wherein R" is selected from the group consisting of CH(CH$_3$)$_2$, CH$_2$CH(CH$_3$)$_2$, and CH(CH$_3$)CH$_2$CH$_3$.

In still another embodiment of such a method, the fraction isolated or derived from hops can comprise a compound of Genus B having the formula:

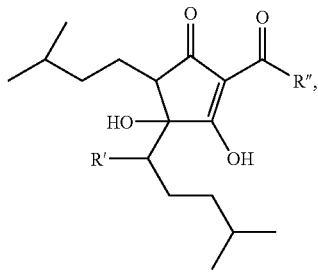

wherein R' is selected from the group consisting of carbonyl, hydroxyl, OR, and OCOR, wherein R is alkyl; and
wherein R" is selected from the group consisting of CH(CH$_3$)$_2$, CH$_2$CH(CH$_3$)$_2$, and CH(CH$_3$)CH$_2$CH$_3$.

In such a method of the invention, the fraction isolated or derived from hops can comprise a compound selected from the group consisting of humulone, cohumulone, adhumulone, isohumulone, isocohumulone, isoadhumulone, dihydro-isohumulone, dihydro-isocohumulone, dihydro-adhumulone, tetrahydro-isohumulone, tetrahydro-isocohumulone, tetrahydro-adhumulone, hexahydro-isohumulone, hexahydro-isocohumulone, and hexahydro-adhumulone.

In yet another embodiment, the invention provides a method of modulating the inflammatory response in cells, the method comprising contacting the cells with a composition comprising a fraction isolated or derived from hops. In an additional embodiment, the invention provides a method of treating or inhibiting a pathological condition in a mammal associated with tissue-specific activation of inflammation, the method comprising administering to the mammal a composition comprising a fraction derived from hops. In such a method, the fraction derived from hops can be selected from the group consisting of isoalpha acids, reduced isoalpha acids, tetra-hydroisoalpha acids, hexa-hydroisoalpha acids, beta acids, and spent hops.

In an embodiment of such a method, the fraction derived from hops can comprise a compound of a supragenus having the formula:

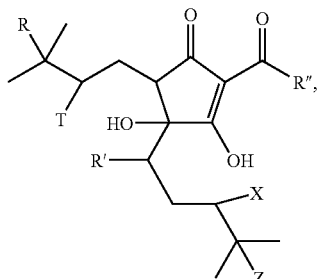

wherein R' is selected from the group consisting of carbonyl, hydroxyl, OR, and OCOR, wherein R is alkyl;
wherein R" is selected from the group consisting of CH(CH$_3$)$_2$, CH$_2$CH(CH$_3$)$_2$, and CH(CH$_3$)CH$_2$CH$_3$; and
wherein R, T, X, and Z are independently selected from the group consisting of H, F, Cl, Br, I, and π orbital, with the proviso that if one of R, T, X, or Z is a π orbital, then the adjacent R, T, X, or Z is also a π orbital, thereby forming a double bond.

In another embodiment of such a method of the invention, the fraction derived from hops can comprise a compound of Genus A having the formula:

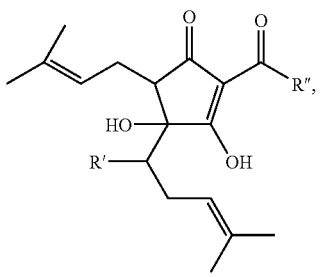

wherein R' is selected from the group consisting of carbonyl, hydroxyl, OR, and OCOR, wherein R is alkyl; and wherein R" is selected from the group consisting of $CH(CH_3)_2$, $CH_2CH(CH_3)_2$, and $CH(CH_3)CH_2CH_3$.

In addition in such a method, the fraction derived from hops can comprise a compound of Genus B having the formula:

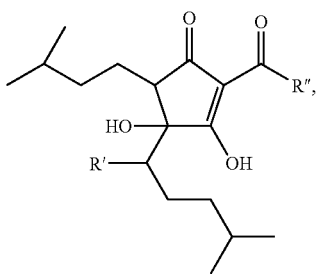

wherein R' is selected from the group consisting of carbonyl, hydroxyl, OR, and OCOR, wherein R is alkyl; and wherein R" is selected from the group consisting of $CH(CH_3)_2$, $CH_2CH(CH_3)_2$, and $CH(CH_3)CH_2CH_3$.

In another embodiment of such a method of the invention, the fraction derived from hops can comprise a compound selected from the group consisting of cohumulone, adhumulone, isohumulone, isocohumulone, isoadhumulone, dihydro-isohumulone, dihydro-isocohumulone, dihydro-adhumulone, tetrahydro-isohumulone, tetrahydro-isocohumulone, tetrahydro-adhumulone, hexahydro-isohumulone, hexahydro-isocohumulone, and hexahydro-adhumulone. In a particular embodiment of the method, the composition can comprise about 0.5 to 10000 mg or about 50 to 7500 mg of the fraction derived from hops. In addition, the composition can comprise about 0.001 to 10 weight percent or about 0.1 to 1 weight percent of the fraction is derived from hops.

In such a method of the invention, the pathological condition can be selected from the group consisting of autoimmune diseases, inflammatory diseases, neurological diseases, and cancer. In another embodiment, the pathological condition can be selected from the group consisting of inflammation, inflammation-associated disorders, arthritis, asthma, bronchitis, menstrual cramps, tendonitis, bursitis, skin-related conditions, gastrointestinal conditions, cancer, ophthalmic diseases, pulmonary inflammation, nervous system disorders, allergic rhinitis, respiratory distress syndrome, endotoxin shock syndrome, atherosclerosis, and central nervous damage.

In still another embodiment, the invention provides a method of modulating the amount of cyclooxygenase-2 (COX-2) activity in target cells without substantially modulating COX-2 activity in non-target cells, the method comprising contacting the cells with a fraction derived from hops. In such a method of the invention, the non-target cells can also be contacted with a fraction derived from hops. The contacting step can be performed in vivo. In the method of the invention, the COX-2 activity can be modulated by inhibition of COX-2 gene.

In yet another embodiment, the invention provides a method of treating or inhibiting a pathological condition in a mammal involving inhibiting inducibility or activity of cyclooxygenase-2 (COX-2), the method comprising administering to the mammal a composition comprising a fraction derived from hops. In such a method, the fraction derived from hops can be selected from the group consisting of isoalpha acids, reduced isoalpha acids, tetra-hydroisoalpha acids, hexa-hydroisoalpha acids, beta acids, and spent hops.

In another embodiment of the method, the fraction derived from hops can comprise a compound of a supragenus having the formula:

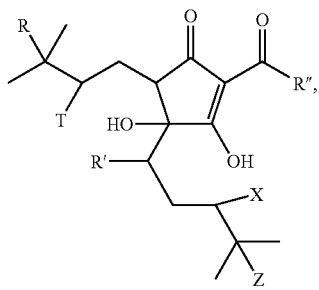

wherein R' is selected from the group consisting of carbonyl, hydroxyl, OR, and OCOR, wherein R is alkyl;
wherein R" is selected from the group consisting of $CH(CH_3)_2$, $CH_2CH(CH_3)_2$, and $CH(CH_3)CH_2CH_3$; and
wherein R, T, X, and Z are independently selected from the group consisting of H, F, Cl, Br, I, and π orbital, with the proviso that if one of R, T, X, or Z is a π orbital, then the adjacent R, T, X, or Z is also a π orbital, thereby forming a double bond.

In such a method, the fraction derived from hops can comprise a compound of Genus A having the formula:

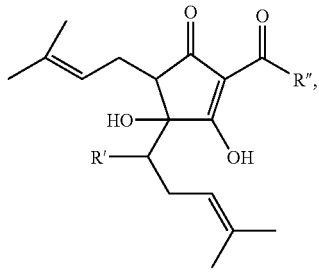

wherein R' is selected from the group consisting of carbonyl, hydroxyl, OR, and OCOR, wherein R is alkyl; and wherein R" is selected from the group consisting of CH(CH₃)₂, CH₂CH(CH₃)₂, and CH(CH₃)CH₂CH₃.

In another embodiment of the method, the fraction derived from hops can comprise a compound of Genus B having the formula:

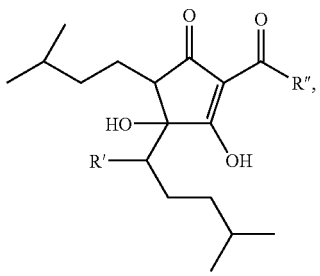

wherein R' is selected from the group consisting of carbonyl, hydroxyl, OR, and OCOR, wherein R is alkyl; and
wherein R" is selected from the group consisting of CH(CH₃)₂, CH₂CH(CH₃)₂, and CH(CH₃)CH₂CH₃.

In still another embodiment of the method, the fraction derived from hops can comprise a compound selected from the group consisting of cohumulone, adhumulone, isohumulone, isocohumulone, isoadhumulone, dihydro-isohumulone, dihydro-isocohumulone, dihydro-adhumulone, tetrahydro-isohumulone, tetrahydro-isocohumulone, tetrahydro-adhumulone, hexahydro-isohumulone, hexahydro-isocohumulone, and hexahydro-adhumulone.

In such a method of the invention, the pathological condition can be selected from the group consisting of wherein the pathological condition is selected from the group consisting of inflammation, inflammation-associated disorders, arthritis, asthma, bronchitis, menstrual cramps, tendonitis, bursitis, skin-related conditions, gastrointestinal conditions, cancer, ophthalmic diseases, pulmonary inflammation, nervous system disorders, allergic rhinitis, respiratory distress syndrome, endotoxin shock syndrome, atherosclerosis, and central nervous damage.

Moreover, the invention provides a method of inhibiting prostaglandin synthesis selectively in target cells, the method comprising contacting the cells with a fraction derived from hops. In such a method, the fraction derived from hops can be selected from the group consisting of isoalpha acids, reduced isoalpha acids, tetra-hydroisoalpha acids, hexa-hydroisoalpha acids, beta acids, and spent hops.

In another embodiment of the method, the fraction derived from hops can comprise a compound of a supragenus having the formula:

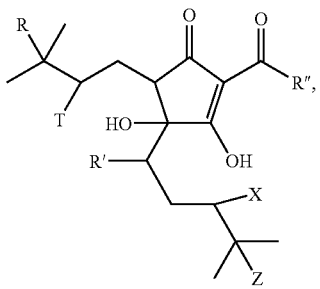

wherein R' is selected from the group consisting of carbonyl, hydroxyl, OR, and OCOR, wherein R is alkyl;

wherein R" is selected from the group consisting of CH(CH₃)₂, CH₂CH(CH₃)₂, and CH(CH₃)CH₂CH₃; and
wherein R, T, X, and Z are independently selected from the group consisting of H, F, Cl, Br, L and π orbital, with the proviso that if one of R, T, X, or Z is a π orbital, then the adjacent R, T, X, or Z is also a π orbital, thereby forming a double bond.

In still another embodiment of the method, the fraction derived from hops comprises a compound of Genus A having the formula:

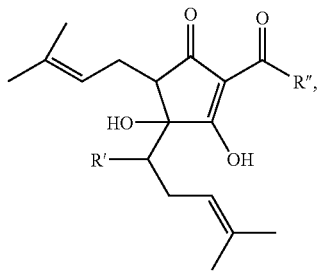

wherein R' is selected from the group consisting of carbonyl, hydroxyl, OR, and OCOR, wherein R is alkyl; and
wherein R" is selected from the group consisting of CH(CH₃)₂, CH₂CH(CH₃)₂, and CH(CH₃)CH₂CH₃.

In yet another embodiment of the method, the fraction derived from hops can comprise a compound of Genus B having the formula:

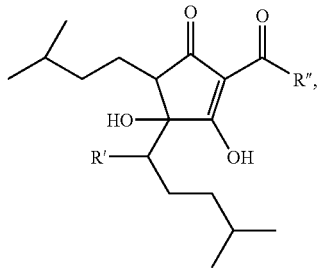

wherein R' is selected from the group consisting of carbonyl, hydroxyl, OR, and OCOR, wherein R is alkyl; and
wherein R" is selected from the group consisting of CH(CH₃)₂, CH₂CH(CH₃)₂, and CH(CH₃)CH₂CH₃.

In a further embodiment of the method, the fraction derived from hops can comprise a compound selected from the group consisting of cohumulone, adhumulone, isohumulone, isocohumulone, isoadhumulone, dihydro-isohumulone, dihydro-isocohumulone, dihydro-adhumulone, tetrahydro-isohumulone, tetrahydro-isocohumulone, tetrahydro-adhumulone, hexahydro-isohumulone, hexahydro-isocohumulone, and hexahydro-adhumulone.

The invention further provides a method of modulating NF-κB in cells not associated with bone resorption, the method comprising contacting the cells with a composition comprising a fraction isolated or derived from hops. The invention additionally provides a method of treating or inhibiting a pathological condition other than osteoporosis in a mammal associated with tissue-specific activation of NF-κB, the method comprising administering to the mammal a composition comprising a fraction isolated or derived from hops. In such a method, the fraction can be derived from hops and selected from the group consisting of isoalpha acids, reduced isoalpha acids, tetra-hydroisoalpha acids, hexa-hydroisoalpha acids, beta acids, and spent hops.

In another embodiment of the method, the fraction can be derived from hops and can comprise a compound of a supragenus having the formula:

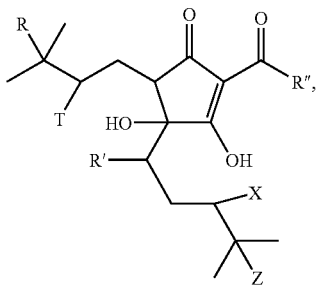

wherein R' is selected from the group consisting of carbonyl, hydroxyl, OR, and OCOR, wherein R is alkyl;
wherein R" is selected from the group consisting of $CH(CH_3)_2$, $CH_2CH(CH_3)_2$, and $CH(CH_3)CH_2CH_3$; and
wherein R, T, X and Z are independently selected from the group consisting of H, F, Cl, Br, I, and π orbital, with the proviso that if one of R, T, X, or Z is a π orbital, then the adjacent R, T, X, or Z is also a π orbital, thereby forming a double bond.

In another embodiment of the method, the fraction is derived from hops and comprises a compound of Genus A having the formula:

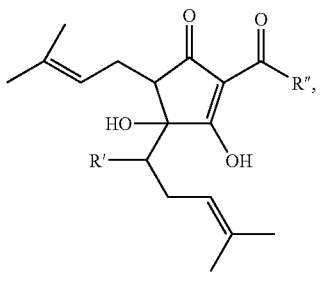

wherein R' is selected from the group consisting of carbonyl, hydroxyl, OR, and OCOR, wherein R is alkyl; and
wherein R" is selected from the group consisting of $CH(CH_3)_2$, $CH_2CH(CH_3)_2$, and $CH(CH_3)CH_2CH_3$.

In still another embodiment of the method, the fraction is derived from hops and comprises a compound of Genus B having the formula:

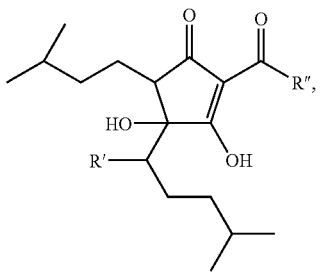

wherein R' is selected from the group consisting of carbonyl, hydroxyl, OR, and OCOR, wherein R is alkyl; and wherein R" is selected from the group consisting of $CH(CH_3)_2$, $CH_2CH(CH_3)_2$, and $CH(CH_3)CH_2CH_3$.

In yet another embodiment of the method, the fraction is derived from hops and comprises a compound selected from the group consisting of cohumulone, adhumulone, isohumulone, isocohumulone, isoadhumulone, dihydro-isohumulone, dihydro-isocohumulone, dihydro-adhumulone, tetrahydro-isohumulone, tetrahydro-isocohumulone, tetrahydro-adhumulone, hexahydro-isohumulone, hexahydro-isocohumulone, and hexahydro-adhumulone.

In a particular embodiment of the method, the composition used in a method of the invention can comprise about 0.5 to 10000 mg or about 50 to 7500 mg of the fraction isolated or derived from hops. Also, the composition can comprise about 0.001 to 10 weight percent or about 0.1 to 1 weight percent of the fraction isolated or derived from hops.

In a method of the invention modulating NFκB, the pathological condition can be selected from the group consisting of autoimmune diseases, inflammatory diseases, neurological diseases, cardiovascular diseases, and cancer. Also, the pathological condition in a method of modulating NFκB can be selected from the group consisting of asthma, HIV-1 replication, cold, and flu.

In another embodiment, the invention provides a method of modulating the amount of cyclooxygenase-2 (COX-2) activity in target cells not associated with bone resorption without substantially modulating COX-2 activity in non-target cells, the method comprising contacting the cells with a fraction isolated or derived from hops. In the method, the non-target cells can also be contacted with a fraction isolated or derived from hops. The contacting step can be performed in vivo. In the method, the COX-2 activity can be modulated by inhibition of the COX-2 gene.

Additionally, the invention provides a method of treating or inhibiting a pathological condition other than osteoporosis in a mammal involving inhibiting inducibility or activity of cyclooxygenase-2 (COX-2), the method comprising administering to the mammal a composition comprising a fraction isolated or derived from hops. In a particular embodiment, the fraction can be derived from hops and selected from the group consisting of isoalpha acids, reduced isoalpha acids, tetra-hydroisoalpha acids, hexa-hydroisoalpha acids, beta acids, and spent hops.

In another embodiment of the method, the fraction is derived from hops and comprises a compound of a supragenus having the formula:

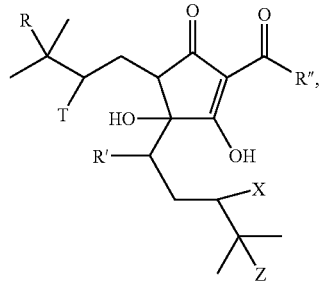

wherein R' is selected from the group consisting of carbonyl, hydroxyl, OR, and OCOR, wherein R is alkyl;
wherein R" is selected from the group consisting of $CH(CH_3)_2$, $CH_2CH(CH_3)_2$, and $CH(CH_3)CH_2CH_3$; and
wherein R, T, X, and Z are independently selected from the group consisting of H, F, Cl, Br, I, and a π orbital, with the proviso that if one of R, T, X, or Z is a π orbital, then the adjacent R, T, X, or Z is also a π orbital, thereby forming a double bond.

In still another embodiment of the method, the fraction is derived from hops and comprises a compound of Genus A having the formula:

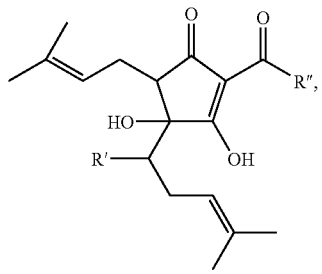

wherein R' is selected from the group consisting of carbonyl, hydroxyl, OR, and OCOR, wherein R is alkyl; and
wherein R" is selected from the group consisting of $CH(CH_3)_2$, $CH_2CH(CH_3)_2$, and $CH(CH_3)CH_2CH_3$.

In yet another embodiment of the method, the fraction can be derived from hops and comprise a compound of Genus B having the formula:

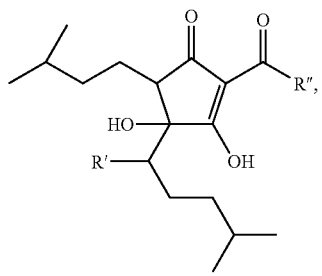

wherein R' is selected from the group consisting of carbonyl, hydroxyl, OR, and OCOR, wherein R is alkyl; and
wherein R" is selected from the group consisting of $CH(CH_3)_2$, $CH_2CH(CH_3)_2$, and $CH(CH_3)CH_2CH_3$.

In a particular embodiment of the method, the fraction can be derived from hops and can comprise a compound selected from the group consisting of cohumulone, adhumulone, isohumulone, isocohumulone, isoadhumulone, dihydro-isohumulone, dihydro-isocohumulone, dihydro-adhumulone, tetrahydro-isohumulone, tetrahydro-isocohumulone, tetrahydro-adhumulone, hexahydro-isohumulone, hexahydro-isocohumulone, and hexahydro-adhumulone.

In another embodiment of the method, the pathological condition can be selected from the group consisting of inflammation, inflammation-associated disorders, arthritis, asthma, bronchitis, menstrual cramps, tendonitis, bursitis, skin-related conditions, gastrointestinal conditions, cancer, ophthalmic diseases, pulmonary inflammation, nervous system disorders, allergic rhinitis, respiratory distress syndrome, endotoxin shock syndrome, atherosclerosis, and central nervous damage.

Also, the invention provides a method of inhibiting prostaglandin synthesis selectively in target cells, the method comprising contacting the cells with a fraction derived from hops. In such a method, the fraction derived from hops can be selected from the group consisting of isoalpha acids, reduced isoalpha acids, tetra-hydroisoalpha acids, hexa-hydroisoalpha acids, beta acids, and spent hops.

In such a method, the fraction derived from hops can comprise a compound of a supragenus having the formula:

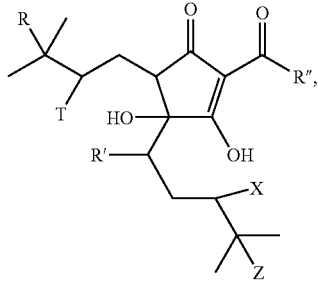

wherein R' is selected from the group consisting of carbonyl, hydroxyl, OR, and OCOR, wherein R is alkyl;
wherein R" is selected from the group consisting of $CH(CH_3)_2$, $CH_2CH(CH_3)_2$, and $CH(CH_3)CH_2CH_3$; and
wherein R, T, X, and Z are independently selected from the group consisting of H, F, Cl, Br, I, and π orbital, with the proviso that if one of R, T, X, or Z is a π orbital, then the adjacent R, T, X, or Z is also a π orbital, thereby forming a double bond.

In another embodiment of the method, the fraction derived from hops can comprise a compound of Genus A having the formula:

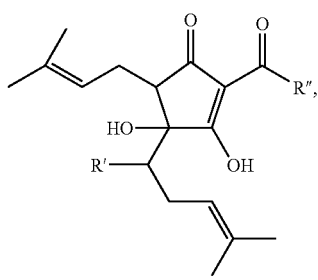

wherein R' is selected from the group consisting of carbonyl, hydroxyl, OR, and OCOR, wherein R is alkyl; and
wherein R" is selected from the group consisting of $CH(CH_3)_2$, $CH_2CH(CH_3)_2$, and $CH(CH_3)CH_2CH_3$.

In yet another embodiment of the method, the fraction derived from hops comprises a compound of Genus B having the formula:

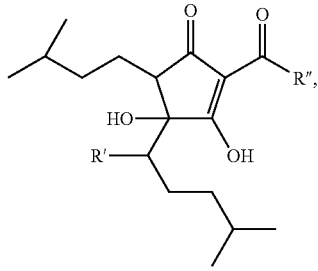

wherein R' is selected from the group consisting of carbonyl, hydroxyl, OR, and OCOR, wherein R is alkyl; and
wherein R" is selected from the group consisting of $CH(CH_3)_2$, $CH_2CH(CH_3)_2$, and $CH(CH_3)CH_2CH_3$.

In still another embodiment of the method, the fraction derived from hops can comprise a compound selected from the group consisting of cohumulone, adhumulone, isohumulone, isocohumulone, isoadhumulone, dihydro-isohumulone, dihydro-isocohumulone, dihydro-adhumulone, tetrahydro-isohumulone, tetrahydro-isocohumulone, tetrahydro-adhumulone, hexahydro-isohumulone, hexahydro-isocohumulone, and hexahydro-adhumulone.

Moreover, the invention provides a method of inhibiting an inflammatory response selectively in target cells, the method comprising contacting the cells with a fraction derived from hops. In such a method, the fraction derived from hops can be selected from the group consisting of isoalpha acids, reduced isoalpha acids, tetra-hydroisoalpha acids, hexa-hydroisoalpha acids, beta acids, and spent hops.

In such a method, the fraction derived from hops can comprise a compound of a supragenus having the formula:

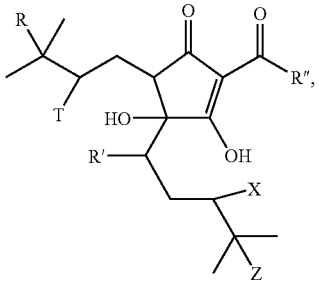

wherein R' is selected from the group consisting of carbonyl, hydroxyl, OR, and OCOR, wherein R is alkyl;
wherein R" is selected from the group consisting of $CH(CH_3)_2$, $CH_2CH(CH_3)_2$, and $CH(CH_3)CH_2CH_3$; and
wherein R, T, X, and Z are independently selected from the group consisting of H, F, Cl, Br, L and π orbital, with the proviso that if one of R, T, X, or Z is a π orbital, then the adjacent R, T, X, or Z is also a π orbital, thereby forming a double bond.

In another embodiment of the method, the fraction derived from hops can comprise a compound of Genus A having the formula:

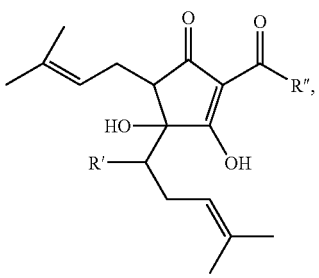

wherein R' is selected from the group consisting of carbonyl, hydroxyl, OR, and OCOR, wherein R is alkyl; and
wherein R" is selected from the group consisting of $CH(CH_3)_2$, $CH_2CH(CH_3)_2$, and $CH(CH_3)CH_2CH_3$.

In still another embodiment of the method, the fraction derived from hops can comprise a compound of Genus B having the formula:

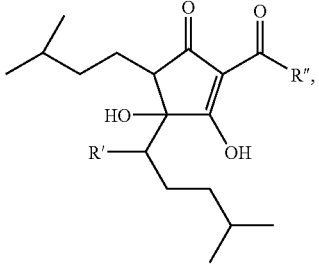

wherein R' is selected from the group consisting of carbonyl, hydroxyl, OR, and OCOR, wherein R is alkyl; and
wherein R" is selected from the group consisting of $CH(CH_3)_2$, $CH_2CH(CH_3)_2$, and $CH(CH_3)CH_2CH_3$.

In such a method of the invention, the fraction derived from hops can comprise a compound selected from the group consisting of cohumulone, adhumulone, isohumulone, isocohumulone, isoadhumulone, dihydro-isohumulone, dihydro-isocohumulone, dihydro-adhumulone, tetrahydro-isohumulone, tetrahydro-isocohumulone, tetrahydro-adhumulone, hexahydro-isohumulone, hexahydro-isocohumulone, and hexahydro-adhumulone. It is understood that compositions of the invention disclosed herein can be used in the various methods of the invention, as disclosed herein.

The invention additional provides a method of treating or inhibiting obesity in a mammal, the method comprising administering to the mammal a composition comprising a fraction isolated or derived from hops and a second component selected from the group consisting of rosemary, an extract derived from rosemary, a compound derived from rosemary, a triterpene species, a diterpene lactone, and tryptanthrin or other compositions of the invention, as disclosed herein.

As disclosed herein in Examples 1, 2 and 27, the AGS gastric mucosal cell line can function as a model system for determining potential gastrointestinal toxicity of anti-inflammatory agents. In AGS cells, COX-1 is expressed four times greater than COX-2. A lower inhibition of $PGE_2$ in AGS cells is favorable because the AGS cell line expresses more COX-1, which maintains mucosal homeostasis. The invention thus also provides a method of determining potential gastrointestinal toxicity of an anti-inflammatory agent. The method can include the steps of contacting an AGS gastric mucosal cell with an anti-inflammatory agent; contacting a target inflammatory cell, for example, an A549 cell, with the anti-inflammatory agent; determining the 50% inhibitory concentration ($IC_{50}$) of prostaglandin $E_2$ ($PGE_2$) expression for the anti-inflammatory agent in each of the AGS cell and target inflammatory cell; and determining the ratio of the $IC_{50}$ value of the AGS cell to the $IC_{50}$ value of the target inflammatory cell, wherein a ratio greater than 1 indicates decreased potential gastrointestinal toxicity and a ratio less than 1 indicates increased potential gastrointestinal toxicity.

As disclosed herein, reduced isomerized alpha acids and isomerized alpha acids appear to inhibit COX-2 expression rather than directly on $PGE_2$ (see Example 25). Further as disclosed herein, hops has no significant dose-related effect on COX-1 or COX-2 enzyme activity, supporting that hops and/or fractions isolated or derived from hops affect COX-2 expression (see Example 26).

The description below is of specific examples setting forth preferred embodiments and are not intended to limit the scope.

Example 1

AGS Gastric Mucosal Cells Constitutively Express Both Cyclooxygenase-1 and Cyclooxygenase-2

Summary

This example demonstrates that the AGS human gastric mucosal cell line, possessing constitutive expression of COX-1 and COX-2, has excellent potential to serve as a model for assessing the gastrointestinal toxicity of cyclooxygenase-inhibiting compounds.

Equipment used in this example included: an OHAS Model #E01140 analytical balance, a Form a Model #F1214 biosafety cabinet (Marietta, Ohio), various pipettes to deliver 0.1 to 100 μL (VWR, Rochester, N.Y.), a cell hand tally counter (VWR Catalog #23609-102, Rochester, N.Y.), a Form a Model #F3210 $CO_2$ incubator (Marietta, Ohio), a hemacytometer (Hausser Model #1492, Horsham, Pa.), a Leica Model #DM IL inverted microscope (Wetzlar, Germany), a PURELAB Plus Water Polishing System (U.S. Filter, Lowell, Mass.), a 4° C. refrigerator (Form a Model #F3775, Marietta, Ohio), a vortex mixer (VWR Catalog #33994-306, Rochester, N.Y.), and a 37° C. water bath (Shel Lab Model #1203, Cornelius, Oreg.).

Chemicals and Reagents

Prostaglandin $E_2$ EIA kit Monoclonal was purchased from Cayman Chemical (Ann Arbor, Mich.). Anti-COX-1 and anti-COX-2 rabbit polygonal antisera were obtained from Upstate Biotechnology (CITY, N.Y.); donkey anti-goat IgG-HRP was procured from Santa Cruz Biotechnology (City, Calif.). Heat inactivated Fetal Bovine Serum (FBS-HI Cat. #35-011CV), and Dulbeco's Modification of Eagle's Medium (DMEM Cat #10-013CV) was purchased from Mediatech (Herndon, Va.). All standard reagents were obtained from Sigma (St. Louis, Mo.) and were the purest commercially available.

Cell Culture

The human gastric mucosal cell line AGS was obtained from the American Type Culture Collection (ATCC number CRL-1739; Manassas, Va.) and sub-cultured according to the instructions of the supplier. The cells were routinely cultured at 37° C. with 5% $CO_2$ in RPMI 1640 containing 10% FBS, with 50 units penicillin/mL, 50 µg streptomycin/mL, 5% sodium pyruvate, and 5% L-glutamine. Exponentially growing cells were seeded into 6-well plates and grown to confluence. A 20 µL aliquot of the supernatant media was sampled for determination of $PGE_2$ content. Cells were then washed in PBS, scraped and lysed for immunoblotting.

Protein Assay

Protein concentrations of cell lysates were determined using the NanoOrange Protein Quantitation Kit with bovine serum albumin as the standard (Molecular Probes, Eugene, Oreg.) according to the procedure supplied by the manufacturer. Fluorescence was determined using a Packard FluoroCount, Model BF 10000 fluorometer with the excitation filter set at 485 nm and emission filter set at 570 nm using Packard PlateReader version 3.0 software. The I-Smart program provided with the Packard PlateReader was used to calculate the protein concentration.

Immunoblotting

Western blotting of COX-1 and COX-2 was performed using PAGEr™ Gold Precast Gels (Bio Whittaker Molecular Applications (Rockland, Me.). AGS cell lysates containing approximately 60 µg protein were loaded with Laemmli Sample Buffer into the wells of the gel in a total volume of 30 µL. The vertical minigel electrophoresis chambers were made by Savant Instruments Inc. (Holbrook, N.Y.), model MV 120. Gels were run at 40 mA/plate (constant current) at room temperature until the bromophenol blue stain reached the bottom of the gel, about one h. Gels were then blotted on the polyvinyl fluoride transfer membranes (Pall Corporation, Ann Arbor, Mich.), overnight, at 500 mA and 4° C. Precision Protein Standard molecular weight markers, unstained, broad range (BioRad, Hercules, Calif.) were used. The BioWest™ Extended duration chemiluminescent substrate, a non-isotopic, horseradish peroxidase substrate kit for Western blot detection (BioImaging Systems, Upland, Calif.) was used for protein visualization. Images of western blots were acquired using a UVP Epi Chemi II Darkroom (BioImaging Systems), analyzed and enhanced by LabWorks™ Image Acquisition and Analysis Software (BioImaging Systems).

$PGE_2$ Assay

A commercial, non-radioactive procedure for quantification of $PGE_2$ was employed (Caymen Chemical, Ann Arbor, Mich.) and the recommended procedure of the manufacturer was used without modification. Briefly, 25 µL of the medium, along with a serial dilution of $PGE_2$ standard samples, were mixed with appropriate amounts of acetylcholinesterase-labeled tracer and $PGE_2$ antiserum, and incubated at room temperature for 18 h. After the wells were emptied and rinsed with wash buffer, 200 µL of Ellman's reagent containing substrate for acetylcholinesterase were added. The reaction was carried out on a slow shaker at room temperature for 1 h and the absorbance at 415 nm was determined. The $PGE_2$ concentration was represented as picograms per $10^5$ cells.

Results

Figure 6:
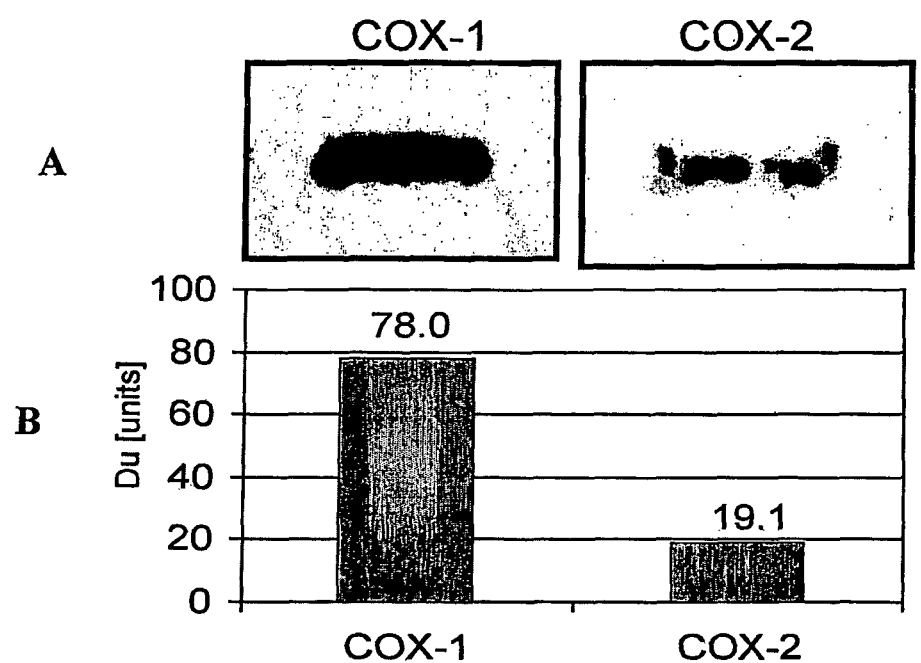
FIG. 6 [A] shows representative immunoblots demonstrating constitutive COX-1 and COX-2 expression in AGS human gastric mucosal cells. The AGS human gastric cell line was cultured in 6-well plates at 37° C. with 5% $CO_2$ in a humidified incubator for 24 hours. Cells were lysed on ice in lysis buffer and protein concentration determined. Fifty μg of cell lysate were solubilized, fractionated on a 10% polyacrylamide gel containing sodium dodecylsulfate (SDS), and transferred onto a nitrocellulose membrane. The membranes were incubated in a blocking buffer and then incubated with the respective primary antibody for 1 h at room temperature. Following primary antibody incubation, the blots were washed three times with Tris-buffered saline and then incubated with the secondary antibody for 1 h. Protein bands were visualized using enhanced chemiluminescence.

As seen in FIG. 6, the AGS cell line constitutively expresses both COX-1 and COX-2, with COX-1 expression approximately 4-times greater than COX-2 expression. $PGE_2$ synthesis in AGS cells over 18 h was 660 pg/$10^5$ cells. Thus, this example demonstrates that the AGS human gastric mucosal cell line, possessing constitutive expression of COX-1 and COX-2, has excellent potential to serve as a model for assessing the gastrointestinal toxicity of cyclooxygenase-inhibiting compounds.

In the past, the classical COX-2 hypothesis has downplayed the role of COX-2 expression in the gastrointestinal mucosa. While in normal gastric mucosa COX-1 is the predominant COX isozyme, as demonstrated in this example and in the literature, there is increasing evidence that detectable amount of COX-2 mRNA and protein are both constitutively expressed and inducible in specific locations of the gastric mucosa in both animals and humans [Halter, F., et al. (2001) *Cyclooxygenase 2-implications on maintenance of gastric mucosal integrity and ulcer healing: controversial issues and perspectives*. Gut 49, 443-453]. Recent studies in rats have shown that whereas selective inhibition of COX-1 or COX-2 is not ulcerogenic, combined inhibition of both COX-1 and COX-2 induces severe lesions in the stomach and small intestine comparable with the effects of NSAID such as indomethacin. This observation suggests an important contribution of COX-2 to the maintenance of gastrointestinal mucosal integrity.

Example 2

Inhibition of $PGE_2$ Synthesis in Gastric Mucosal Cells by Nonsteroidal Anti-Inflammatory Drugs Summary This example illustrates that inhibition of $PGE_2$ synthesis in AGS gastric cells by NSAIDs correlates with their observed clinical gastric irritation.

Chemicals

Rofecoxib and celexocib were obtained. Diisofluorophosphate (DIFP), nimensulide, ibuprofen, salicylic acid, aspirin, indomethacin and acetaminophen were purchased from Sigma (St Louis, Mo.). All other chemicals were obtained from suppliers as described in Example 1.

Cells

A549 (human pulmonary epithelial; ATCC number CCL-185) and AGS cells (human gastric mucosa; ATCC number CRL-1739) were obtained from the American Type Culture Collection (Manassas, Va.) and sub-cultured according to the instructions of the supplier. The cells were routinely cultured at 37° C. with 5% $CO_2$ in RPMI 1640 containing 10% FBS, with 50 units penicillin/mL, 50 µg streptomycin/mL, 5% sodium pyruvate, and 5% L-glutamine. On the day of the experiments, exponentially growing cells were harvested and washed with serum-free RPMI 1640.

The log phase A549 and AGS cells were plated at $8 \times 10^4$ cells per well in 0.2 mL growth medium per well in a 96-well tissue culture plate. For the determination of $PGE_2$ inhibition by the test compounds in A549 cells, the procedure of Warner et al., also known as the WHMA-COX-2 protocol Warner, T. D., et al. (1999) *Nonsteroid drug selectivities for cyclo-oxygenase-1 rather than cyclo-oxygenase-2 are associated with human gastrointestinal toxicity: a full in vitro analysis*. Proc Natl Acad Sci USA 96, 7563-7568.] was followed with no modifications. Briefly, 24 hours after plating of the A549 cells, interleukin-1β (10 ng/mL) was added to induce the expression of COX-2. After 24 hr, the cells were washed with serum-free RPMI 1640 and the test materials, dissolved in DMSO and serum-free RPMI, were added to the wells to achieve final concentrations of 25, 5.0, 0.5 and 0.05 µg/mL. Each concentration was run in duplicate. DMSO was added to the control wells in an equal volume to that contained in the test wells. Sixty minutes later, A23187 (50 µM) was added to the wells to release arachidonic acid. Twenty-five µL of media were sampled from the wells 30 minutes later for $PGE_2$ determination.

Non-stimulated AGS cells were used in these studies. Twenty-four hours after plating in the 96-well microtiter plates, the cells were washed with serum-free RPMI 1640 and the test materials, dissolved in DMSO and serum-free RPMI, were added to the wells to achieve final concentrations of 25, 5.0, 0.5 and 0.05 µg/mL. Each concentration was run in duplicate. DMSO was added to the control wells in an equal volume to that contained in the test wells. Sixty minutes later, arachidonic acid was added to the wells to achieve a final concentration of 100 µM. Twenty-five µL of media were sampled from the wells 30 minutes after the addition of arachidonic acid for $PGE_2$ determination.

Cell Viability

Cell viability was assessed by a 3-(4,5-dimethylthiazol-2-yl)-2,5-diphenyltetrazolium bromide (MTT)-based colorimetric assay (Sigma, St. Louis, Mo.). The MTT solution was added directly to the wells after sampling for $PGE_2$ determination. The absorbance of each well was read at 580 nm using an ELISA plate reader. No toxicity was observed at the highest concentrations tested for any of the compounds.

Calculations

The median inhibitory concentration ($IC_{50}$) for $PGE_2$ synthesis was calculated using CalcuSyn (BIOSOFT, Ferguson, Mo.). This statistical package performs multiple drug dose-effect calculations using the median effect methods described by T-C Chou and P. Talaly [(1984) *Quantitative analysis of dose-effect relationships: the combined effects of multiple drugs or enzyme inhibitors*. Adv Enzyme Regul 22, 27-55.] hereby incorporated by reference.

Briefly, the analysis correlates the "Dose" and the "Effect" in the simplest possible form: $fa/fu=(C/C_m)^m$, where C is the concentration or dose of the compound and Cm is the median-effective dose signifying the potency. Cm is determined from the x-intercept of the median-effect plot. The fraction affected by the concentration of the test material is fa and the fraction unaffected by the concentration is fu (fu=1−fa). The exponent m is the parameter signifying the sigmoidicity or shape of the dose-effect curve. It is estimated by the slope of the median-effect plot.

The median-effect plot is a graph of x=log(C) vs y=log(fa/fu) and is based on the logarithmic form of Chou's median-effect equation. The goodness of fit for the data to the median-effect equation is represented by the linear correlation coefficient r of the median-effect plot. Usually, the experimental data from enzyme or receptor systems have an r>0.96, from tissue culture an r>0.90 and from animal systems an r>0.85. In the cell-based studies reported here, all linear correlation coefficients were greater than 0.90. Experiments were repeated three times on three different dates. The percent inhibition at each dose was averaged over the three independent experiments and used to calculate the median inhibitory concentrations reported.

Results

The highly specific COX-2 inhibitor diisofluorophosphate exhibited a median inhibitory concentration in A549 cells of 1.19 µg/mL and did not inhibit $PGE_2$ synthesis in AGS cells at the highest concentration tested of 25 µg/mL (Table 3). Rofecoxib, and celexocib, selective COX-2 drugs, were 27-, and 14-times, respectively, more potent inhibitors of $PGE_2$ synthesis in the target A549 cells than in the non-target AGS gastric mucosal cells. This finding demonstrates not only COX-2 selectivity, but also target-tissue selectivity consistent with their low gastrointestinal toxicity. Nimensulide, another new, selective COX-2 inhibitor was equally as potent in the inhibition of $PGE_2$ synthesis in both cell lines. The anti-inflammatory agent acetaminophen, purported to inhibit an unidentified isozyme of COX (COX-3) and having low gastrointestinal toxicity, inhibited $PGE_2$ biosynthesis in A549 cells but had no effect on $PGE_2$ synthesis in AGS gastric mucosal cells.

Alternatively and consistent with their demonstrated clinical gastric toxicity, ibuprofen, aspirin and indomethacin all exhibited more inhibition of $PGE_2$ synthesis in the AGS cell line than in the target A549 cells. Salicylic acid, an anti-inflammatory agent that inhibits the expression of COX-2 with little gastric irritation, was inactive in both cell models.

TABLE 3

Median inhibitory concentrations for test comoounds in the A549 and AGS cell lines.

| Compound | $IC_{50}$ A549 [µg/mL] | $IC_{50}$ AGS [µg/mL] | $IC_{50}$ AGS/ $IC_{50}$ A549 |
|---|---|---|---|
| Diisofluorophosphate | 1.19 | >25 | >21 |
| Rofecoxib | 0.081 | 2.21 | 27.3 |
| Celexocib | 0.004 | 0.055 | 13.8 |
| Nimensulide | 0.10 | 0.11 | 1.0 |
| Ibuprofen | 0.10 | 0.05 | 0.50 |
| Aspirin | 0.48 | 0.09 | 0.19 |
| Indomethacin | 0.033 | 0.002 | 0.002 |
| Salicylic acid | >25 | >25 | >1 |
| Acetaminophen | 0.607 | >25 | >41 |

These results validate the use of the AGS gastric mucosal cell line to evaluate potential gastrointestinal toxicity of anti-inflammatory agents capable of inhibiting the synthesis of $PGE_2$. They also demonstrate cellular specificity in the action of COX-inhibiting compounds. A ratio of 1 for $IC_{50}$ AGS/ $IC_{50}$ A549 indicates $IC_{50}$s that are the same for both the AGS cell and A549 cells. If the ratio is higher than 1 for $IC_{50}$ AGS/$IC_{50}$ A549, then the inhibition of $PGE_2$ is lower for the AGS cells. A lower inhibition of $PGE_2$ in AGS cells is favorable because AGS cell line expresses more COX-1, which maintains mucosal homeostasis.

Example 3

Inhibition of $PGE_2$ Synthesis in Stimulated and Nonstimulated Murine Macrophages by Hops (*Humulus lupulus*) Compounds and Deriviatives Summary This example illustrates the potency of hops fractions and derivatives to inhibit COX-2 synthesis of $PGE_2$ preferentially over COX-1 synthesis of $PGE_2$ in the murine macrophage model.

Chemicals and Reagents

Bacterial lipopolysaccharide (LPS; B E. coli 055:B5) was from Sigma (St. Louis, Mo.). Hops fractions (1) alpha hop (1% alpha acids; AA), (2) aromahop OE (10% beta acids and 2% isomerized alpha acids, (3) isohop (isomerized alpha acids; IAA), (4) beta acid solution (beta acids BA), (5) hexahop gold (hexahydro isomerized alpha acids; HHIAA), (6) redihop (reduced isomerized-alpha acids; RIAA), (7) tetrahop (tetrahydro-iso-alpha acids THIAA) and (8) spent hops were obtained from Betatech Hops Products (Washington, D.C., U.S.A.). The spent hops were extracted two times with equal volumes of absolute ethanol. The ethanol was removed by heating at 40° C. until a only thick brown residue remained. This residue was dissolved in DMSO for testing in RAW 264.7 cells. Unless otherwise noted, all standard reagents were obtained from Sigma (St. Louis, Mo.) and were the purest commercially available. All other chemicals and equipment were as described in Examples 1 and 2.

Cell Culture

RAW 264.7 cells, obtained from American Type Culture Collection (Catalog #TIB-71, Manassas, Va.), were grown in Dulbecco's Modification of Eagle's Medium (DMEM, Mediatech, Herndon, Va.) and maintained in log phase. The DMEM growth medium was made by adding 50 mL of heat inactivated FBS and 5 mL of penicillin/streptomycin to a 500 mL bottle of DMEM and storing at 4° C. The growth medium was warmed to 37° C. in water bath before use.

On day one of the experiment, the log phase RAW 264.7 cells were plated at $8\times10^4$ cells per well in 0.2 mL growth medium per well in a 96-well tissue culture plate in the morning. At the end of the day one (6 to 8 h post plating), 100 µL of growth medium from each well were removed and replaced with 100 µL fresh medium.

A 1.0 mg/mL stock solution of LPS, used to induce the expression of COX-2 in the RAW 264.7 cells, was prepared by dissolving 1.0 mg of LPS in 1 mL DMSO. It was vortexed until dissolved and stored at 4° C. Before use, it was melted at room temperature or in a 37° C. water bath.

On day two of the experiment, test materials were prepared as 1000× stock in DMSO. In 1.7 mL microfuge tubes, 1 mL DMEM without FBS was added for test concentrations of 0.05, 0.10, 0.5, and 1.0 µg/mL. Two µL of the 1000×DMSO stock of the test material was added to the 1 mL of medium without FBS. The tube contained the final concentration of the test material concentrated 2-fold and the tube placed in an incubator for 10 minutes to equilibrate to 37° C.

For COX-2 associated $PGE_2$ synthesis, 100 µL of medium were removed from each well of the cell plates prepared on day one and replaced with 100 µL of equilibrated 2× final concentration of the test compounds. Cells were then incubated for 90 minutes. Twenty µL of LPS were added to each well of cells to be stimulated to achieve a final concentration of 1 µg LPS/mL and the cells were incubated for 4 h. The cells were further incubated with 5 µM arachidonic acid for 15 minutes. Twenty-five µL of supernatant medium from each well was transferred to a clean microfuge tube for the determination of $PGE_2$ released into the medium.

Following the LPS stimulation, the appearance of the cells was observed and viability was determined as described in Example 2. No toxicity was observed at the highest concentrations tested for any of the compounds. Twenty-five µL of supernatant medium from each well was transferred to a clean microfuge tube for the determination of $PGE_2$ released into the medium. $PGE_2$ was determined and reported as previously described in Example 1.

For COX-1 associated $PGE_2$ synthesis, 100 µL of medium were removed from each well of the cell plates prepared on day one and replaced with 100 µL of equilibrated 2× final concentration of the test compounds. Cells were then incubated for 90 minutes. Next, instead of LPS stimulation, the cells were incubated with 100 µM arachidonic acid for 15 minutes. Twenty-five µL of supernatant medium from each well was transferred to a clean microfuge tube for the determination of $PGE_2$ released into the medium. The appearance of the cells was observed and viability was determined as described in Example 2. No toxicity was observed at the highest concentrations tested for any of the compounds. Twenty-five µL of supernatant medium from each well was transferred to a clean microfuge tube for the determination of $PGE_2$ released into the medium. $PGE_2$ was determined and reported as previously described in Example 1. The median inhibitory concentrations ($IC_{50}$) for $PGE_2$ synthesis from both COX-2 and COX-1 were calculated as described in Example 2.

TABLE 4

COX-2 and COX-1 inhibition in RAW 264.7 cells by hop fractions and derviatives

| Test Material | COX-2 $IC_{50}$ [µg/mL] | COX-1 $IC_{50}$ [µg/mL] | COX-1/COX-2 |
|---|---|---|---|
| Alpha hop (AA) | 0.21 | 6.2 | 30 |
| Aromahop OE | 1.6 | 4.1 | 2.6 |
| Isohop (IAA) | 0.13 | 18 | 144 |
| Beta acids (BA) | 0.54 | 29 | 54 |
| Hexahop (HHIAA) | 0.29 | 3.0 | 11 |
| Redihop (RIAA) | 0.34 | 29 | 87 |
| Tetrahop (THIAA) | 0.20 | 4.0 | 21 |
| Spent hops (EtOH) | 0.88 | 21 | 24 |

As seen in Table 4, all hops fractions and derivative selectively inhibited COX-2 over COX-1 in this target macrophage model. This was a novel and unexpected finding. The extent of COX-2 selectivity for the hops derivatives IAA and RIAA, respectively, 144- and 87-fold, was unanticipated. Such high COX-2 selectivity combined with low median inhibitory concentrations, has not been previously reported for natural products from other sources.

Example 4

Hops Compounds and Derivatives are not Direct Cyclooxygenase Enzyme Inhibitors

Summary

This example illustrates that hops compounds and derivatives do not inhibit $PGE_2$ synthesis in A549 pulmonary epithelial cells at physiologically relevant concentrations when tested using the WHMA-COX-2 protocol.

Chemicals

Hops and hops derivatives used in this example were previously described in Example 3. All other chemicals were obtained from suppliers as described in Examples 1 and 2.

Cells

A549 (human pulmonary epithelial) Cells were obtained from the American Type Culture Collection (Manassas, Va.) and sub-cultured according to the instructions of the supplier. The cells were routinely cultured at 37° C. with 5% $CO_2$ in RPMI 1640 containing 10% FBS, with 50 units penicillin/mL, 50 µg streptomycin/mL, 5% sodium pyruvate, and 5% L-glutamine. On the day of the experiments, exponentially growing cells were harvested and washed with serum-free RPMI 1640.

Log phase A549 cells were plated at $8\times10^4$ cells per well with 0.2 mL growth medium per well in a 96-well tissue culture plate. For the determination of $PGE_2$ inhibition by the test compounds, the procedure of Warner et al. [(1999) *Non-steroid drug selectivities for cyclo-oxygenase-1 rather than cyclo-oxygenase-2 are associated with human gastrointestinal toxicity: a full in vitro analysis*. Proc Natl Acad Sci USA 96, 7563-7568], also known as the WHMA-COX-2 protocol was followed with no modification. Briefly, 24 hours after plating of the A549 cells, interleukin-1β (10 ng/mL) was added to induce the expression of COX-2. After 24 hr, the cells were washed with serum-free RPMI 1640 and the test materials, dissolved in DMSO and serum-free RPMI were added to the wells to achieve final concentrations of 25, 5.0, 0.5 and 0.05 μg/mL. Each concentration was run in duplicate. DMSO was added to the control wells in an equal volume to that contained in the test wells. Sixty minutes later, A23187 (50 μM) was added to the wells to release arachidonic acid. Twenty-five μL of media were sampled from the wells 30 minutes later for $PGE_2$ determination.

Cell viability was assessed as previously described in Example 2. No toxicity was observed at the highest concentrations tested for any of the compounds. $PGE_2$ in the supernatant medium was determined and reported as previously described in Example 1.

The median inhibitory concentration ($IC_{50}$) for $PGE_2$ synthesis was calculated as previously described in Example 2.

Results

At the doses tested, the experimental protocol failed to capture a median effective concentration of any of the hops extracts or derivatives. Since the protocol requires the stimulation of COX-2 expression prior to the addition of the test compounds, the likely answer to the failure of the test materials to inhibit $PGE_2$ synthesis is that their mechanism of action is to inhibit the expression of the COX-2 isozyme and not activity directly. While some direct inhibition can be observed using the WHMA-COX-2 protocol, this procedure is inappropriate in evaluating the anti-inflammatory properties of hops compounds or derivatives of hops compounds.

Example 5

Lack of Inhibition of $PGE_2$ Synthesis in Gastric Mucosal Cells by Hops (*Humulus lupulus*) Compounds and Deriviatives Summary This example illustrates the lack of $PGE_2$ inhibition by hops fractions and in the AGS human gastric mucosal cell line implying low gastric irritancy potential of these compounds.

Chemicals and reagents were used as described in Example 3. AGS cells were grown and used for testing hops compounds and derivatives as described in Example 2. $PGE_2$ was determined and reported as previously described in Example 1. The median inhibitory concentrations ($IC_{50}$) for $PGE_2$ synthesis from AGS cells were calculated as described in Example 2.

TABLE 5

Lack of $PGE_2$, inhibition in AGS gastric mucosal cells by hop fractions and derviatives

| Test Material | $IC_{50}$ AGS [μg/mL] |
|---|---|
| Alpha hop (AA) | >25 |
| Aromahop OE | >25 |
| Isohop (IAA) | >25 |
| Beta acids (BA) | >25 |
| Hexahop (HHIAA) | >25 |

TABLE 5-continued

Lack of $PGE_2$, inhibition in AGS gastric mucosal cells by hop fractions and derviatives

| Test Material | $IC_{50}$ AGS [μg/mL] |
|---|---|
| Redihop (RIAA) | >25 |
| Tetrahop (THIAA) | >25 |
| Spent hops (EtOH) | >25 |

As seen in Table 5, all hops fractions and derivatives were unable to inhibit $PGE_2$ synthesis by 50% or more at the highest concentrations tested in the AGS gastric mucosal cell line. Based on the anti-inflammatory potency exhibited by these fractions in target macrophages, this was a novel and unexpected finding.

Example 6

Inhibition of $PGE_2$ Synthesis by Rosemary Extract and Compounds Found in Rosemary Summary This example illustrates the anti-inflammatory effect of rosemary extract and compounds commonly found in rosemary, carnosic acid, ursolic acid and oleanolic acid in target cells and the effect of rosemary extract and oleanolic acid on $PGE_2$ synthesis in gastrointestinal cells.

Equipment used, chemicals, cell handing and calculation of median inhibitory concentrations were performed as previously described in Examples 1, 2 and 3. Carnosic acid, ursolic acid and oleanolic acid were obtained from Sigma (St. Louis, Mo.). The rosemary extract was a hexane extract obtained from selected leaves of *Rosmarinus officinalis* by mean (95%+/−3% rosemary extract) that complied with US regulation (21 CFR 101-22). It was determined by HPLC analysis that the extract contained a minimum of 11% phenolic diterpenes (consisting of carnosic acid, carnosol, methyl carnosate, rosemadial, rosemarinic acid), 4.9% min carnosic acid, and a minimum of 7.6% the sum of carnosol+ carnosic acid. The carnosic acid was purchased from Sigma (St. Louis, Mo.) and the oleanolic acid (80%) was obtained from Sabinsa (121 Ethel Road West, Piscataway, N.J.).

TABLE 6

$PGE_2$ inhibition in RAW 264.7 and AGS cells by a rosemary extract, carnosic acid, ursolic acid, and oleanolic acid.

| Test Material (COX-2/COX-1)† | RAW 264.7 $IC_{50}$ [μg/mL] | RAW or AGS $IC_{50}$ [μg/mL] | COX-1/ COX-2 |
|---|---|---|---|
| Rosemary extract (RAW/AGS) | 0.51 | 4.0 | 7.8 |
| Carnosic acid (RAW/RAW) | 0.50 | 231 | 470 |
| Ursolic acid (RAW/RAW) | 1.91 | 33 | 17 |
| Oleanolic acid (RAW/RAW) | 1.15 | 19 | 17 |
| Oleanolic acid (RAW/AGS) | 1.15 | 5.0 | 4.3 |

†Indicates the cell lines used to estimate inhibitor effects, respectively, on COX-2 or COX-1 synthesis of $PGE_2$.
In all cases, LPS-stimulated RAW 264.7 cells were used to determine median inhibitory concentrations of COX-2 mediated $PGE_2$ synthesis. For the estimation of the effects of test materials on COX-1-mediated synthesis, either non-stimulated RAW 264.7 or non-stimulated AGS cells were used.

Results

All test materials exhibited potent inhibition of $PGE_2$ synthesis in LPS-stimulated RAW 264.7 cells indicating inhibition of the COX-2 isozyme (Table 6). Surprisingly, the rosemary extract was more potent than ursolic and oleanolic acids and equal to pure carnosic acid in potency with a median inhibitory concentration of 0.5 μg test material/mL medium. Since the rosemary extract contained only 11% carnosic acid or derivative, the inference is that the interaction of the carnosic acid derivatives or the myriad of other compounds in the rosemary extract were acting in concert or synergistically to provide such a potent inhibition of COX-2. Alternatively, one of the compounds previously identified in rosemary and listed earlier has extremely high potency for inhibiting COX-2 mediated synthesis of $PGE_2$.

In non-stimulated RAW 264.7 cells, the pure compounds were relatively inactive exhibiting $IC_{50}$ values of 231, 33 and 19 µg/mL, respectively, for carnosic, ursolic and oleanolic acids. This indicated a strong preference for COX-2 inhibition over COX-1 for synthesis of $PGE_2$ in the RAW 264.7 target cell model. This extent of COX isozyme selectivity has never been reported in the literature and was an unexpected result. In the AGS gastric mucosal cell line, however, both the rosemary extract and oleanolic acid exhibited potent inhibition of $PGE_2$ synthesis.

Example 7

Synergistic Inhibition of $PGE_2$ Synthesis in Target Cells by Hops $CO_2$-Extract in Combination with Triterpenoids Oleanolic Acid and Ursolic Acid Equipment used, chemicals, cell handing and calculation of median inhibitory concentrations were performed as previously described in Examples 1, 2 and 3. The hops CO2-extract was purchased from Hopunion, (Yakama, Wash.) and contained 30 to 60% alpha-acids and 15 to 45% beta-acids. Oleanolic and ursolic acids and were obtained from Sigma (St. Louis, Mo.) and were the highest purity commercially available (>98%).

Synergy of test components was quantified using the combination index (CI) parameter. The CI of Chou-Talaly is based on the multiple drug-effect and is derived from enzyme kinetic models (Chou, T.-C. and Talalay, P. (1977) A simple generalized equation for the analysis of multiple inhibitions of Michaelis-Menten kinetic systems. J. Biol. Chem. 252: 6438-6442). The equation determines only the additive effect rather than synergism or antagonism. However, we define synergism as a more than expected additive effect, and antagonism as a less than expected additive effect as proposed by Cho and Talalay Using the designation of CI=1 as the additive effect, we obtain for mutually exclusive compounds that have the same mode of action or for mutually non-exclusive drugs that have totally independent modes of action the following relationships: CI<1, =1, and >1 indicating synergism, additivity and antagonism, respectively.

Results

The 4:1 ($CO_2$-extract:triterpenoid) combination tested in RAW 264.7 cells exhibited potent synergy over the entire dose-response curve. Combination indexes computed for both test materials at the $IC_{50}$, $IC_{75}$ and $IC_{90}$ are presented in Table 7. As described in this example, the synergy of these combinations covered a concentration range of 0.001 to 50 µg/mL of each component of the combination.

TABLE 7

Computed Combination Indexes for the dose-response curves of 1:4 combinations of a $CO_2$-extract of hops and the triterpenes oleanolic and ursolic acid

| Test Material | $CI_{50}$ | $CI_{75}$ | $CI_{90}$ | Mean CI |
|---|---|---|---|---|
| $CO_2$-Extract:Oleanolic acid [1:4] | 0.514 | 0.461 | 0.414 | 0.463 |
| $CO_2$-Extract:Ursolic acid [1:4] | 0.529 | 0.650 | 0.806 | 0.662 |

Example 8

Synergistic Inhibition of $PGE_2$ Synthesis by Hops Combinations with an Extract of Rosemary in Target and Nontarget Cells Summary This example illustrates synergy of combinations of reduced isomerized alpha acids and rosemary extract on target A549 cells and synergistic antagonism of rosemary inhibition of $PGE_2$ synthesis in AGS gastric mucosal cells.

Equipment used, chemicals, cell handing and calculation of median inhibitory concentrations were performed as previously described in Examples 1, 2, 3 and 4. Several differences in the protocol for testing in the A549 cells were incorporated in this example. First, test materials were added to the medium 60 minutes prior to stimulation with IL-1β. Second, in the determination of dose-response curves, 5 µM arachidonic acid was used in place of the calcium ionophore A23187. Synergy of the combinations was computed as described in Example 7.

Results

Table 8 shows $PGE_2$ inhibition by reduced isomerized alpha-acids, rosemary extract and a 2:1 combinations of reduced isomerized alpha-acids and rosemary extract in IL-1β stimulated A549 cells. This cell line represents a model target cell for anti-inflammatory efficacy. Median inhibitory concentrations for reduced isomerized alpha-acids and rosemary extract independently were, respectively, 0.84 and 1.3 µg/mL. The 2:1 combination of reduced isomerized alpha-acids and rosemary extract exhibited synergy at and below the median inhibitory concentration of the combination.

Table 9 shows inhibition of $PGE_2$ synthesis in the human gastric AGS cells. These cells represent a model for gastrointestinal toxicity of prostaglandin inhibitors. Test materials exhibiting inhibition of $PGE_2$ synthesis in these cells would be expected to demonstrate gastric irritation and ulceration with chronic use. The inhibition of $PGE_2$ synthesis by rosemary extract was synergistically antagonized by a 2:1 combination of reduced isomerized alpha-acids and rosemary extract. This unexpected result represents a novel finding of synergistic antagonism.

TABLE 8

Median inhibitory concentrations and combination index for $PGE_2$ inhibition by reduced isomerized alpha-acids, rosemary extract and a combination of isomerized alpha-acids and rosemary extract in IL-1β-stimulated A549 cells

| Test Material | $IC_{50}$ [µg/mL] | Combination Index < 1.0† [µg/mL] |
|---|---|---|
| Reduced isomerized alpha-acids (RIAA) | 0.84 | |
| Rosemary extract | 1.3 | |
| RIAA:Rosemary 2:1 | 0.48 | At 0.48 and below |

†The combination index was less than 1 over the portion of the dose-response curve at and below the IC50 value indicating synergistic inhibition of $PGE_2$ synthesis by the combination at these concentrations.

TABLE 9

Synergy of a 1:1 combination of reduced isomerized alpha-acids with rosemary extract resulting in a reduction of $PGE_2$ inhibition in AGS gastric mucosal cells.

| Test Material | $IC_{50}$ [μg/mL] | Combination Index |
|---|---|---|
| Reduced isomerized alpha-acids (RIAA) | >25 | — |
| Rosemary | 4.0 | — |
| RIAA:Rosemary 1:1 | >25 | >1.0† |

†The combination index was greater than 1 over the entire dose-response curve indicating synergistic antagonism of $PGE_2$ inhibition by the combination.

While this example only presents the combination of rosemary extract with one of the hops derivative, reduced isomerized alpha-acids, it would be obvious for one skilled in the art to assume to expect the same results with other hops derivatives that also show no $PGE_2$ inhibition with AGS cells at dose as high as 25 μg/mL. Examples of these hops derivatives would include isomerized-alpha acids, hexahydro-isomerized alpha acids, tetrahydro-iso-alpha acids and extracts of spent hops.

Example 9

Synergistic Inhibition of $PGE_2$ Synthesis by Reduced Isomerized Alpha-Acids and Oleanolic Acid in Target Cells with no Effect on $PGE_2$ Synthesis in Nontarget Cells Summary This example illustrates that reduced isomerized alpha-acids exhibit strong synergy with the triterpene oleanolic acid in the inhibition of $PGE_2$ synthesis is the target A549 cells and synergistically antagonize oleanolic acid inhibition of $PGE_2$ synthesis in gastric cells.

Equipment used, chemicals, cell handing and calculation of median inhibitory concentrations were performed as previously described in Examples 1, 2, 3 and 4. Several differences in the protocol for testing in the A549 cells were incorporated in this example. First, test materials were added to the medium 60 minutes prior to stimulation with IL-1β. Second, in the determination of dose-response curves, A549 cells remained in the presence of test material overnight before the sampling of media for $PGE_2$ determination. Synergy of the combinations was computed as described in Example 7. Reduced isomerized alpha-acids were obtained as a one percent aqueous solution from John Haas, Inc. (Yakima, Wash.) and oleanolic acid was obtained from Sabinsa (Piscataway, N.J.) and was 80% pure. Synergy of the combinations was computed as described in Example 7.

Results

Table 10 shows $PGE_2$ inhibition by oleanolic acid, reduced isomerized alpha-acids and various combinations of reduced isomerized alpha-acids and oleanolic acid in A549 cells. This cell line represents a model target cell for anti-inflammatory efficacy. Median inhibitory concentrations for reduced isomerized alpha-acids and oleanolic acid independently were, respectively, 0.03 and 0.39 μg/mL. Combinations of reduced isomerized alpha-acids and oleanolic acid consisting of 10:1, 5:1, and 1:5, respectively, exhibited synergy on the dose-response curve at combined concentrations of 0.11, 0.38 and 0.76 μg/mL. Thus, when the sum of the two components was equal to or less than 0.11, 0.38 or 0.76 μg/mL, their ability to inhibit $PGE_2$ synthesis was greater than the sum of their individual activities.

TABLE 10

Median inhibitory concentrations and combination indexes for $PGE_2$ inhibition by reduced isomerized alpha-acids, oleanolic acid and four combinations of isomerized alpha-acids and oleanolic acid in IL-1β-stimulated A549 cells.

| Test Material | $IC_{50}$ [μg/mL] | Combination Index < 1.0 |
|---|---|---|
| Oleanolic acid (80% Sabinsa) | 0.390 | — |
| Reduced isomerized alpha-acids (RIAA) | 0.028 | — |
| RIAA:Oleanolic acid – [10:1] | 0.042 | At 0.11 μg/mL and below |
| RIAA:Oleanolic acid – [5:1] | 0.059 | At 0.38 μg/mL and below |
| RIAA:Oleanolic acid – [1:5] | 0.022 | At 0.76 μg/mL and below |
| RIAA:Oleanolic acid – [1:10] | 0.166 | No |

† The combination index was less than 1 over the portion of the dose-response curve at the tabulated values indicating synergistic inhibition of $PGE_2$ synthesis by the combination at and below these concentrations.

Table 11 shows inhibition of $PGE_2$ synthesis in the human gastric AGS cells. These cells represent a model for gastrointestinal toxicity of prostaglandin inhibitors. Test materials exhibiting inhibition of $PGE_2$ synthesis in these cells would be expected to demonstrate gastric irritation and ulceration with chronic use. The inhibition of $PGE_2$ synthesis by oleanolic acid was synergistically antagonized by all combinations with reduced isomerized alpha-acids. This unexpected result represents a novel finding of synergistic antagonism.

TABLE 11

Synergy of reduced isomerized alpha-acids with oleanolic acid resulting in a reduction of $PGE_2$ inhibition in AGS gastric mucosal cells

| Test Material | $IC_{50}$ [μg/mL] | Combination Index > 1.0† |
|---|---|---|
| Oleanolic acid | 5.0 | — |
| Reduced isomerized alpha-acids (RIAA | >25 | — |
| RIAA:Oleanolic acid - [10:1] | >25 | Antagonism |
| RIAA:Oleanolic acid - [5:1] | >25 | Antagonism |
| RIAA:Oleanolic acid - [1:5] | >25 | Antagonism |
| RIAA:Oleanolic acid - [1:10] | >25 | Antagonism |

†When CI > 1.0 at the $IC_{50}$, the combination is said to exhibit antagonism in the inhibition of $PGE_2$ synthesis by AGS cells.

While this example only presents the combination of oleanolic acid with one of the hops derivative, reduced isomerized alpha-acids, it would be obvious for one skilled in the art to assume to expect the same results with other hops derivatives that also show no $PGE_2$ inhibition with AGS cells at dose as high as 25 μg/mL. Examples of these hops derivatives would include isomerized-alpha acids, hexahydro-isomerized alpha acids, tetrahydro-iso-alpha acids and extracts of spent hops.

Example 10

Synergistic Inhibition of $PGE_2$ Synthesis by a Combination of Reduced Isomerized Alpha Acids with Tryptanthrin in Target Cells with No Effect on $PGE_2$ Synthesis in Nontarget Cells Summary This example illustrates a potent synergy of a 1:1 combination of reduced isomerized alpha acids and tryptanthrin on target A549 cells and synergistic antagonism of tryptanthrin inhibition of $PGE_2$ synthesis in AGS gastric mucosal cells.

Equipment used, chemicals, cell handing and calculation of median inhibitory concentrations were performed as previously described in Examples 1, 2, 3, 4 and 9. Reduced isomerized alpha-acids were obtained as a one percent aqueous solution from John Haas, Inc. (Yakima, Wash.) and tryptanthrin was obtained from Waco Chemicals (Richmond, Va.) and was the highest purity commercially available. Several differences in the protocol for testing in the A549 cells were incorporated in this example. First, test materials were added to the medium 60 minutes prior to stimulation with IL-1β. Second, in the determination of dose-response curves, A549 cells remained in the presence of test material overnight before the sampling of media for $PGE_2$ determination. Synergy of the combinations was computed as described in Example 7.

Results

Table 12 shows $PGE_2$ inhibition by reduced isomerized alpha-acids, tryptanthrin and a 1:1 combination of reduced isomerized alpha-acids and tryptanthrin in IL-1β stimulated A549 cells. This cell line represents a model target cell for anti-inflammatory efficacy. Median inhibitory concentrations for reduced isomerized alpha-acids and tryptanthrin independently were, respectively, 0.0.028 and 0.30 µg/mL. The 1:1 combination of reduced isomerized alpha-acids and tryptanthrin exhibited synergy over the entire dose-response curve.

Table 13 shows inhibition of $PGE_2$ synthesis in the human gastric AGS cells. These cells represent a model for gastrointestinal toxicity of prostaglandin inhibitors. Test materials exhibiting inhibition of $PGE_2$ synthesis in these cells would be expected to demonstrate gastric irritation and ulceration with chronic use. The inhibition of $PGE_2$ synthesis by tryptanthin was synergistically antagonized by a 1:1 combination of reduced isomerized alpha-acids and tryptanthrin or conjugates thereof. This unexpected result represents a novel finding of synergistic antagonism.

TABLE 12

Median inhibitory concentrations and combination index for $PGE_2$ inhibition by reduced isomerized alpha-acids, tryptanthrin and a combination of isomerized alpha-acids and tryptanthrin in IL-1β-stimulated A549 cells

| Test Material | $IC_{50}$ [µg/mL] | Combination Index |
| --- | --- | --- |
| Reduced isomerized alpha-acids RIAA | 0.028 | — |
| Tryptanthrin | 0.300 | — |
| RIAA:Tryptanthrin - [1:1] | $3.1 \times 10^7$ | <1.0† |

†The combination index was less than 1 over the entire dose-response curve indicating synergistic inhibition of $PGE_2$ synthesis by the combination.

TABLE 13

Synergy of combinations of reduced isomerized alpha-acids with tryptanthrin resulting in a reduction of $PGE_2$ inhibition in AGS gastric mucosal cells.

| Test Material | $IC_{50}$ [µg/mL] | Combination Index |
| --- | --- | --- |
| Reduced isomerized alpha-acids (RIAA) | >25 | — |
| Tryptanthrin | 4.2 | — |
| RIAA:Tryptanthrin - [1:1] | >25 | >1.0† |

†The combination index was greater than 1 over the entire dose-response curve indicating synergistic antagonism of $PGE_2$ inhibition by the combination.

While this example only presents the combination of tryptanthrin with one of the hops derivative, reduced isomerized alpha-acids, it would be obvious for one skilled in the art to assume to expect the same results with other hops derivatives that also show no $PGE_2$ inhibition with AGS cells at dose as high as 25 µg/mL. Examples of these hops derivatives would include isomerized-alpha acids, hexahydro-isomerized alpha acids, tetrahydro-iso-alpha acids and extracts of spent hops.

Example 11

Ex Vivo Inhibition of $PGE_2$ Synthesis by a Plasma Sample from a Human Receiving a Combination Containing Hops Derivatives, a Rosemary Extract and Oleanolic Acid Summary This example demonstrates the presence of $PGE_2$ inhibiting materials in a human subject following ingestion of a 5:5:1 combination of reduced isomerized alpha acids, rosemary extract and oleanolic acid three times per day for five days.

Equipment used, chemicals, RAW 264.7 cell handing and calculation of $PGE_2$ concentrations were performed as previously described in Examples 1, 2, and 3. Reduced isomerized alpha acids, rosemary extract and oleanolic acid were as described in Examples 3, 6 and 7, respectively. Gel caps were made to contain 200 mg reduced isomerized alpha acids, 200 mg rosemary and 40 mg oleanolic acid in an oil base. Plasma samples were obtained from a human volunteer prior to and five days after consuming three capsules per day for five days. Capsules were taken at approximately eight-hour intervals throughout the day. On the fifth day, blood was drawn one hour before taking the last capsule and 1, 2, 4 and 7 hours after dosing. All $PGE_2$ assays in plasma samples were replicated eight times. Outliers were defined and eliminated if the value was more than three standard deviations from the group mean computed without the perceived outlier. Raw data with and without the outliers were graphed. Concentrations of test material in plasma relating to percent $PGE_2$ inhibition were estimated using a standard curve of the combination in commercial plasma (Gibco, Grand Island, N.Y.).

Figure 7:
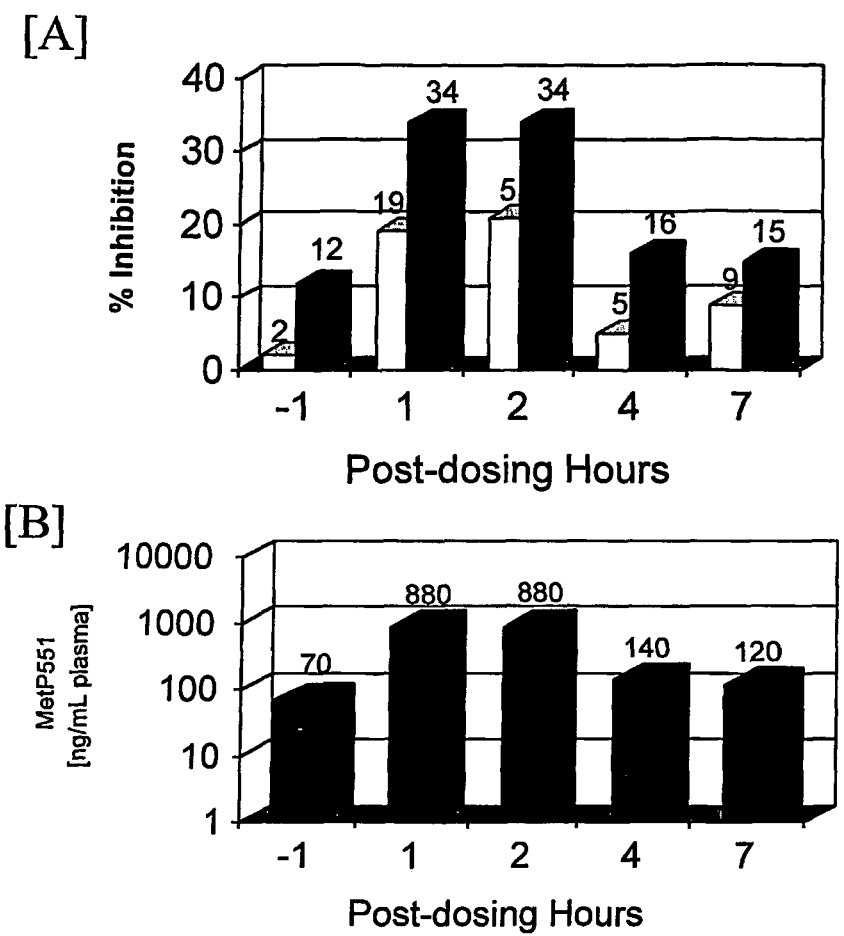
FIG. 7 [A] shows the percent inhibition of $PGE_2$ synthesis in LPS-stimulated RAW 264.7 cells by plasma samples from a human volunteer receiving 880 mg t.i.d. of a test hops derivative formulation. White bars are means of raw data and dark bars are those means computed with the elimination of outliers (never more than two of the eight replicates). The gel capsules of the test formulation contained 200 mg reduced isomerized alpha-acids, 200 mg rosemary extract and 40 mg oleanolic acid.

FIG. 7[A] illustrates the inhibition of $PGE_2$ synthesis by the plasma samples at the indicated times. A 9- to 3-fold increase in $PGE_2$ inhibition was observed during the first post-dosing hour. Effective half-life (time to reduce the ability to inhibit $PGE_2$ synthesis by one-half) of the test material was approximately four hours.

Estimates of test material relating to the observed percentage inhibition of $PGE_2$ synthesis in RAW 264.7 cells are presented in FIG. 7[B]. Using only the data with outliers removed, a 12.5-fold increase in test material concentration was noted during the first hour. A maximal concentration of 880 ng/mL plasma was seen at both the 1 and 2 post-dosing hours. The concentration half-live was approximately 2.2 hours. The lack of consistency between the effective half-life and concentration half-life may be inferred to be due to the synergy of components in the formulation. Efficacy is extended due to positive and synergistic interactions among the isomerized alpha acids, the myriad of compounds in the rosemary extract and oleanolic acid as has been demonstrated by the examples in this application.

Example 12

Normalization of Joint Function Following Trauma

A representative composition of the preferred embodiments as a dietary supplement would be in an oral formulation, i.e. tablets or gel caps that would supply one of the following combinations: 0.1 to 10 mg isocohumulone/kg per day; 0.01 to 10 mg dihydroadhumulone/kg per day, 0.01 to 10 mg tetrahydro-isocohumulone/kg per day; 0.01 to 10 mg/kg per day of hexahydro-isohumulone/kg per day for a 70 kg person.

Normalization of joint movement following physical trauma due to exercise or repetitive movement stress would be expected to occur following two to ten doses. This result would be expected in all animals.

Example 13

Normalization of Joint Function Following Trauma

A representative composition of the preferred embodiments as a dietary supplement would be in an oral formulation, i.e. tablets or gel caps that would supply one of the following combinations:
17 mg reduced isomerized alpha-acid/kg per day, 17 mg rosemary extract/kg per day and 17 mg ursolic acid/kg per day;
17 mg reduced isomerized alpha-acid/kg per day, 17 mg rosemary extract/kg per day and 3.4 mg ursolic acid/kg per day;
34 mg reduced isomerized alpha-acid/kg per day, 34 mg rosemary extract/kg per day and 3.4 mg ursolic acid/kg per day;
340 mg reduced isomerized alpha-acid/kg per day, 340 mg rosemary extract/kg per day and 3.4 mg ursolic acid/kg per day;
17 mg reduced isomerized alpha-acid/kg per day, 17 mg rosemary extract/kg per day and 85 mg ursolic acid/kg per day;
17 mg reduced isomerized alpha-acid/kg per day, 17 mg rosemary extract/kg per day and 170 mg ursolic acid/kg per day; or
17 mg reduced isomerized alpha-acid/kg per day, 17 mg rosemary extract/kg per day and 1700 mg ursolic acid/kg per day for a 70 kg person.

Normalization of joint movement following physical trauma due to exercise or repetitive movement stress would be expected to occur following two to ten doses. This result would be expected in all animals.

Example 14

Clinical Effectiveness of Lotion Formulations in the Treatment of Acne Rosacea

A lotion designed to contain one of the following:
1. 0.1% wt of the isomerized alpha-acid isocohumulone;
2. 0.1% wt of the reduced isomerized alpha-acid dihydro-adhumulone;
3. 0.1% wt of the tetrahydroisoalpha-acid tetrahydro-isocohumulone; or
4. 0.1% wt hexahydro-isohumulone is applied to affected areas of patients who have exhibited acne rosacea as diagnosed by their health practitioner and confirmed by an independent board-certified dermatologist.

Self-evaluation tests and are administered one week prior to the study to quantify the surface area affected and redness. In addition, similar variables are scored by the professional clinical staff not aware of the patients treatment status. These evaluations are repeated on Days 0, 7, 14 and 21.

Patients are randomly assigned to the test formulation or placebo at the start of the study. The test formulation and placebo are applied to the affected area one or two times per day. Treatment for health conditions such as diabetes, hypertension, etc. is allowed during the study. Scores are statistically compared between the test formulation and the placebo for each of the four observational periods. Patients treated with the composition of the preferred embodiments in a lotion formulation are considered improved if the patients' scores improve by greater than 20% from the pre-test scores within each category evaluated. The percentage of persons exhibiting improvement is compared between the combination formulations and the placebo control. The difference between the two groups is considered statistically significant if the probability of rejecting the null hypothesis when true is less than five percent.

Example 15

Clinical Effectiveness of Lotion Formulations in the Treatment of Acne Rosacea

A lotion designed to contain one of the following:
1. 0.1% wt of the alpha-acid humulone;
2. 0.1% wt of the isomerized alpha-acid isocohumulone;
3. 0.1% wt of the reduced isomerized alpha-acid dihydro-adhumulone;
4. 0.1% wt of the tetrahydroisoalpha-acid tetrahydro-isocohumulone; or
5. 0.1% wt of the hexahydroisoalpha-acid hexahydro-isohumulone is applied to affected areas of patients who have exhibited acne rosacea as diagnosed by their health practitioner and confirmed by an independent board-certified dermatologist.

Self-evaluation tests and are administered one week prior to the study to quantify the surface area affected and redness. In addition, similar variables are scored by the professional clinical staff not aware of the patients treatment status. These evaluations are repeated on Days 0, 7, 14 and 21.

Patients are randomly assigned to the test formulation or placebo at the start of the study. The test formulation and placebo are applied to the affected area one or two times per day. Treatment for health conditions such as diabetes, hypertension, etc. is allowed during the study. Scores are statistically compared between the test formulation and the placebo for each of the four observational periods. Patients treated with the composition of the preferred embodiments in a lotion formulation are considered improved if the patients' scores improve by greater than 20% from the pre-test scores within each category evaluated. The percentage of persons exhibiting improvement is compared between the combination formulations and the placebo control. The difference between the two groups is considered statistically significant if the probability of rejecting the null hypothesis when true is less than five percent.

Example 16

Clinical Effectiveness of Lotion Formulations in the Treatment of Acne Rosacea

A lotion designed to contain one of the following:
1. 0.1% wt of the alpha-acid humulone and 0.1% trypanthrin;
2. 0.1% wt of the isomerized alpha-acid isocohumulone and 0.1% trypanthrin;
3. 0.1% wt of the reduced isomerized alpha-acid dihydro-adhumulone and 0.1% tryptanthrin;
4. 0.1% wt of the tetrahydroisoalpha-acid tetrahydro-isocohumulone and 0.1% tryptanthrin; or
5. 0.1% wt of the hexahydroisoalpha-acid hexahydro-isohumulone and 0.1% tryptanthrin is applied to affected areas of patients who have exhibited acne rosacea as diagnosed by their health practitioner and confirmed by an independent board-certified dermatologist.

Self-evaluation tests and are administered one week prior to the study to quantify the surface area affected and redness. In addition, similar variables are scored by the professional clinical staff not aware of the patients treatment status. These evaluations are repeated on Days 0, 7, 14 and 21.

Patients are randomly assigned to the test formulation or placebo at the start of the study. The test formulation and placebo are applied to the affected area one or two times per day. Treatment for health conditions such as diabetes, hypertension, etc. is allowed during the study. Scores are statistically compared between the test formulation and the placebo for each of the four observational periods. Patients treated with the composition of the preferred embodiments in a lotion formulation are considered improved if the patients' scores improve by greater than 20% from the pre-test scores within each category evaluated. The percentage of persons exhibiting improvement is compared between the combination formulations and the placebo control. The difference between the two groups is considered statistically significant if the probability of rejecting the null hypothesis when true is less than five percent.

Example 17

Clinical Effectiveness of a Lotion Formulation in the Treatment of Psoriasis

This example is performed in the same manner as described in Examples 14, 15 and 16 except that the composition is applied to affected areas of patients who have exhibited psoriasis as diagnosed by their own practitioner and confirmed by an independent board-certified dermatologist. Self-evaluation tests are administered one week prior to the study to quantify the surface area affected and skin condition. In addition, similar variables are scored by the professional clinical staff not aware of the patients treatment status. These evaluations are repeated on Days 0, 7, 30 and 60.

Patients are randomly assigned to the test formulation or placebo at the start of the study. The test formulation and placebo are applied to the affected area one or two times per day. Treatment for health conditions such as diabetes, hypertension, etc. is allowed during the study. Scores are statistically compared between the test formulation and the placebo for each of the four observational periods. Patients treated with the composition of the preferred embodiments as the test lotion formulation are considered improved if the patients' scores improve by greater than 20% from the pre-test scores within each category evaluated. The percentage of persons exhibiting improvement is compared between the test formulation and the placebo control. The difference between the two groups is considered statistically significant if the probability of rejecting the null hypothesis when true is less than five percent.

Example 18

Clinical Effectiveness of a Formulation in the Treatment of Alzheimer's Disease

An oral formulation as described in Examples 12 and 13 is administered to patients who have manifested an early stage of Alzheimer's Disease (AD), as diagnosed by their practitioner and confirmed by an independent board-certified neurologist. Two weeks before the clinical trial, the patients undergo appropriate psychoneurological tests such as the Mini Mental Status Exam (MMSE), the Alzheimer Disease Assessment Scale (ADAS), the Boston Naming Test (BNT), and the Token Test (TT). Neuropsychological tests are repeated on Day 0, 6 weeks and 3 months of the clinical trial. The tests are performed by neuropsychologists who are not aware of the patient's treatment regimen.

Patients are randomly assigned to the test formulation or placebo at the start of the study. The test formulation and placebo are taken orally one or two times per day. Treatment for conditions such as diabetes, hypertension, etc. is allowed during the study. Scores are statistically compared between the test formulation and the placebo for each of the three observational periods. Without treatment, the natural course of AD is significant deterioration in the test scores during the course of the clinical trial. Patients treated with the composition of the preferred embodiments as the test formulation are considered improved if the patients' scores remain the same or improve during the course of the clinical trial.

Example 19

Oral Formulation in the Treatment and Prevention of Colon Cancer

An oral formulation as described in Examples 12 and 13 is administered to patients who have manifested an early stage of colon cancer as diagnosed by their own practitioner and confirmed by a independent board-certified oncologist.

Patients are randomly assigned to the test formulation or a placebo at the start of the study. The test formulation and placebo are taken orally one or two times per day. Treatment for conditions such as diabetes, hypertension, etc. is allowed during the study. Endoscopic evaluations are made at one, two, six and twelve months. Evidence of reappearance of the tumor during any one of the four follow-up clinical visits is considered a treatment failure. The percentage of treatment failures is compared between the test formulation and the placebo control. Under the experimental conditions described, the test material is expected to decrease the tumor incidence with respect to the control group. The difference between the two groups is considered statistically significant if the probability of rejecting the null hypothesis when true is less than five percent.

Example 20

Oral Formulation for the Treatment of Irritable Bowel Syndrome

An oral formulation as described in Examples 12 and 13 is administered to patients who have manifested irritable bowel syndrome as diagnosed by their practitioner. Normal bowel functioning is restored within 48 hours.

Example 21

Normalization of Joint Functioning in Osteoarthritis

Using compositions described in Examples 12 and 13 normalization of joint stiffness due to osteoarthritis occurs following five to twenty doses, in the presence or absence of glucosamine or chondroitin sulfate. In addition, the composition does not interfere with the normal joint rebuilding effects of these two proteoglycan constituents, unlike traditional non-steroidal anti-inflammatory agents.

Example 22

Mite Dust Allergens Activate $PGE_2$ Biosynthesis in A549 Pulmonary Cells

Summary

This example illustrates that house mite dust allergens can induce $PGE_2$ biosynthesis in pulmonary epithelial cells.

Background

Sensitivity to allergens is a problem for an increasing number of consumers. This issue has been complicated by a surprising increase in asthma over the past few years. Asthma suffers are especially sensitive to airborne allergens. Allergy rates are also on the rise. This gives rise to increased awareness of the causes of allergy symptoms and how to decrease the associated discomfort. Approximately 10% of the population become hypersensitized (allergic) upon exposure to antigens from a variety of environmental sources. Those antigens that induce immediate and/or delayed types of hypersensitivity are known as allergens. These include products of grasses, trees, weeds, animal dander, insects, food, drugs, and chemicals. Genetic predisposition of an individual is believed to play a role in the development of immediate allergic responses such as atopy and anaphylaxis whose symptoms include hay fever, asthma, and hives.

Many allergens are protein-based molecules, and these protein allergens can originate from many sources. It has been know for some time that one of the most common sources of allergens in a house is from dust mites. Of course, as is the case with all allergens, only certain people are allergic to dust mite allergens. But this group of people can be quite large in many areas, especially in hot humid areas. For example, in the southeastern United States of America, where it is both hot and humid for much of the year, the incidence of house dust mite allergies in the general population can be as high as 25%. House dust mites thrive in plush carpets, overstuffed upholstery, cushy bed comforters and the like.

Methods

Mite Dust Allergen Isolation

*Dermatophagoides farinae* are the American house dust mite. *D. farinae* were cultured on a 1:1 ratio of Purina Laboratory Chow (Ralston Purina, Co, St. Louis, Mo.) and Fleischmann's granulated dry yeast (Standard Brands, Inc. New York, N.Y.) at room temperature and 75% humidity. Live mites were aspirated from the culture container as they migrated from the medium, killed by freezing, desiccated and stored at 0% humidity. The allergenic component of the mite dust was extracted with water at ambient temperature. Five-hundred mg of mite powder were added to 5 mL of water (1:10 w/v) in a 15 mL conical centrifuge tube (VWR, Rochester, N.Y.), shaken for one minute and allowed to stand overnight at ambient temperature. The next day, the aqueous phase was filtered using a 0.2 µm disposable syringe filter (Nalgene, Rochester, N.Y.). The filtrate was termed mite dust allergen and used to test for induction of $PGE_2$ biosynthesis in A549 pulmonary epithelial cells.

Cell Culture and Treatment

This experiment involved the human airway epithelial cell line, A549 (American Type Culture Collection, Bethesda, Md.). The cells were cultured and treated as previously described in Example 2. Mite allergen was added to the culture medium to achieve a final concentration of 1000 ng/mL. Twenty-four hours later, the culture medium was sampled for $PGE_2$ concentration.

$PGE_2$ Assay

Determination of $PGE_2$ in the culture medium was performed as previously described in Example 1.

Statistical Analysis

Means of eight replicates per treatment were computed using Excel® spreadsheets (Microsoft, Redmond, Wash.).

Results

Figure 8:
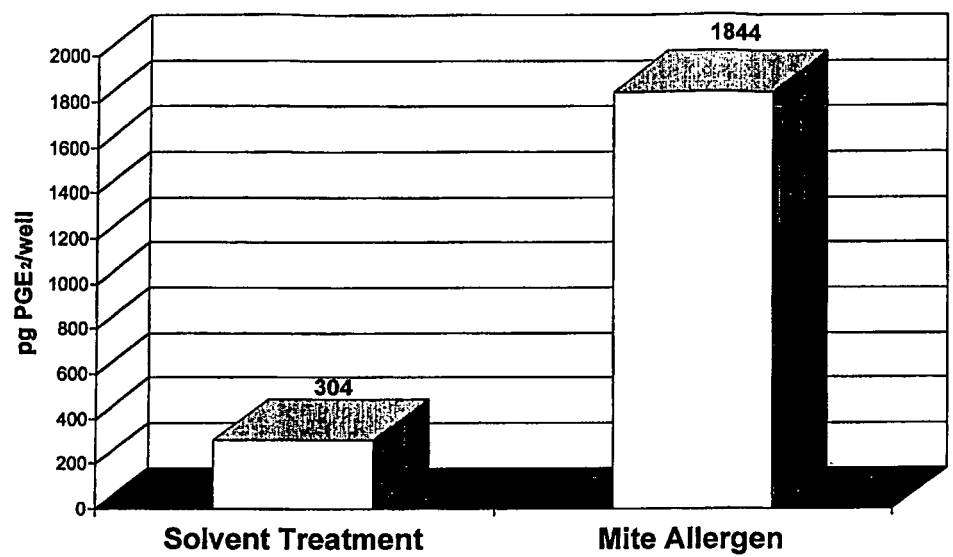
FIG. 8 illustrates the induction of $PGE_2$ synthesis by mite allergen in A549 pulmonary cells treated for 24 hours.

Mite allergen treatment increased $PGE_2$ biosynthesis 6-fold in A549 cells relative to the solvent treated controls (FIG. 8).

Example 23

Hops Derivatives Inhibit Mite Dust Allergen Activation of $PGE_2$ Biosynthesis in A549 Pulmonary Cells Summary This example illustrates that hops derivatives are capable of inhibiting the $PGE_2$ stimulatory effects of mite dust allergens in A549 pulmonary cells.

Methods

The cell line and testing procedures are as described in Example 22. In addition to mite dust allergen, test materials included Hops fractions (1) alpha hop (1% alpha acids; AA), (2) aromahop OE (10% beta acids and 2% isomerized alpha acids, (3) isohop (isomerized alpha acids; IAA), (4) beta acid solution (beta acids BA), (5) hexahop gold (hexahydro isomerized alpha acids; HHIAA), (6) redihop (reduced isomerized-alpha acids; RIAA), and (7) tetrahop (tetrahydro-iso-alpha acids (THIAA). Test materials at a final concentration of 10 µg/mL were added 60 minutes prior to the addition of the mite dust allergen.

Results

Table 15 depicts the extent of inhibition of $PGE_2$ biosynthesis by hops derivatives in A549 pulmonary cells stimulated by mite dust allergen. All hops derivatives were capable of significantly inhibiting the stimulatory effects of mite dust allergens.

TABLE 15

$PGE_2$ inhibition by hops derviatives in A549 pulmonary epithelial cells stimulated by mite dust allergen

| Test Material | Percent Inhibition of $PGE_2$ Biosynthesis |
|---|---|
| Alpha hop (AA) | 81 |
| Aromahop OE | 84 |
| Isohop (IAA) | 78 |
| Beta acids (BA) | 83 |
| Hexahop (HHIAA) | 82 |
| Redihop (RIAA) | 81 |
| Tetrahop (THIAA) | 76 |

In conclusion, it would also be useful to identify a natural formulation of compounds that would inhibit expression of COX-2, inhibit prostaglandin synthesis selectively in target cells, or inhibit inflammation response selectively in target cells.

A preferred embodiment comprises compositions containing at least one fraction isolated or derived from hops (*Humulus lupulus*). Examples of fractions isolated or derived from hops are alpha acids, isoalpha acids, reduced isoalpha acids, tetra-hydroisoalpha acids, hexa-hydroisoalpha acids, beta acids, and spent hops. Preferred compounds of fractions isolated or derived from hops, include, but are not limited to, humulone, cohumulone, adhumulone, isohumulone, isocohumulone, isoadhumulone, dihydro-isohumulone, dihydro-isocohumulone, dihydro-adhumulone, tetrahydro-isohumulone, tetrahydro-isocohumulone, tetrahydro-adhumulone, hexahydro-isohumulone, hexahydro-isocohumulone, and hexahydro-adhumulone. Preferred compounds can also bear substituents, such as halogens, ethers, and esters.

Another embodiment comprises composition containing tryptanthrin and conjugates thereof.

Other embodiments relate to combinations of components. One embodiment relates to compositions that include, as a first component, an active ingredient isolated or derived from an extract of hops and as a second component at least one member selected from the group consisting of rosemary (*Rosmarinus officinalis* L.), an extract or compound derived from rosemary, a triterpene species or derivatives or conjugates thereof, and tryptanthrin or conjugates thereof. Another embodiment relates to compositions that include, as a first component, tryptanthrin or conjugates thereof and as a second component at least one member selected from the group consisting of an active ingredient isolated or derived from an extract of hops, rosemary, an extract or compound derived from rosemary, and a triterpene species or derivatives or conjugates thereof.

Example 24

Effect of Modified Hops Component on NF-kB

Figure 9:
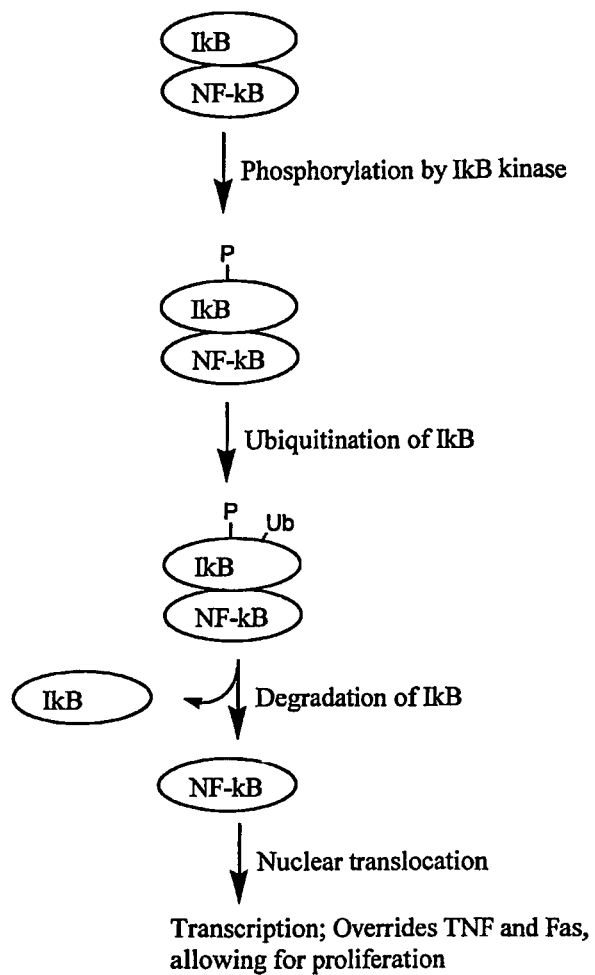
FIG. 9 shows a pathway of activation of NF-κB. In the cytoplasm, NF-κB is inhibited by IκB. An upstream activating signal may cause phosphorylation of IκB by IKK (IκB kinase). This triggers the degradation of IκB through the ubiquitin system. Once freed from IκB, the free NF-κB can then translocate to the nucleus and activate transcription.

As stated above, NF-κB, a heterodimer of the proteins p50 and RelA, is an inducible eukaryotic DNA binding protein complex that is broadly expressed and plays a pivotal role in regulating multiple biological responses, such as the inflammatory and immune responses in mammalian cells. Targets of NF-κB include IL-2, the IL-2 receptor, and acute-phase proteins of the liver. In addition to its role in immune responses, NF-κB activation overrides the apoptotic response to TNF and Fas, allowing for proliferation instead. NF-κB is cytoplasmic when inactive, maintained there by I-κB. As shown in FIG. 9, various stimuli lead to activation of IKK (IκB Kinase), which phosphorylates IκB, marking it for ubiquitination and degradation. Once IκB is degraded, NF-κB is freed to initiate transcription. Following transcriptional activation of a gene, NF-κB is also rapidly degraded.

The ability to detect activated or nondegraded NF-κB is a function of timing. Following cytokine stimulation of a cell, activated NF-κB can be detected within 30 minutes. Within hours, the activated NF-κB is degraded and only nonactivated, complexed NF-κB remains. In this example, whole cell NF-κB was determined 24 hours following trivalent stimuli of Interluken-1β (IL-1β), γ-interferon (IFN), and TNFα. By this time, activated NF-κB has been degraded and only non-activated, bound NF-κB remains. The IκB inhibitor is removed with lysis buffer and NF-κB is quantified by enzyme immunoassay following capture by dsDNA containing the NF-κB response element. Compounds or mixtures that inhibit NF-κB activation can be identified as producing an increase in NF-κB-associated color development in cell lysates that have been treated with cytokines and the test material. Since NF-κB plays a key role in regulating both inflammatory and immune responses in mammalian cells, as well as contributing to cancer cell growth and increased replication of various viruses like HIV-1, the development of agents that impair NF-κB activation or function could have important therapeutic applications.

Methods

Chemicals

NF-κB EIA kits were obtained from Active Motif (Carlsbad, Calif.). Heat inactivated Fetal Bovine Serum (FBS-HI Cat. #35-011CV), and Dulbeco's Modification of Eagle's Medium (DMEM Cat #10-013CV) was purchased from Mediatech (Herndon, Va.). Reduced isomerized-alpha acids (RIAA) were obtained from John I. Haas, Inc., Yakima, Wash. Interluken-1β (IL-1β), γ-inteferon (IFN), TNFα, vitamin D3 (VD3) and all standard chemicals were obtained from Sigma (St Louis, Mo.) and were of the highest purity commercially available.

Cell Culture and Treatment of Cells

The human monocytic cell line U937 was obtained from the American Type Culture Collection (Manasas, Va.) and subcultured according to instructions from the supplier. The cells were routinely cultured at 37° C. with 5% $CO_2$ in RPMI 1640 (Life Technologies, Grand Island, N.Y.) containing 10% FBS, with 50 units penicillin/mL, 50 µg streptomycin/mL, 5% sodium pyruvate, and 5% L-glutamine (Life Technologies). For the experiment, U937 cells were cultured in 6-well plates at 37° C. with 5% $CO_2$ in a humidified incubator for 24 hours prior to treatment with test agents. RIAA in dimethyl-sulfoxide (10 µL) was added to the cells to achieve a final concentration of 10 µg RIAA/mL 60 min prior to stimulation with VD3 (100 nM) or VD3 and the cytokine mixture (25 ng IL-1β, 150 ng IFN, and 20 ng TNFa/mL). Twenty-four hr later, the cells were washed and lysed with reagents supplied with the TransAM NFkB Chemi kit.

Protein Assay

Protein concentrations of cell lysates were determined using the NanoOrange Protein Quantitation Kit with bovine serum albumin as the standard (Molecular Probes, Eugene, Oreg.) according to the procedure supplied by the manufacturer. Fluorescence was determined using a Packard Fluoro-Count, Model BF 10000 fluorometer with the excitation filter set at 485 nm and emission filter set at 570 nm using Packard PlateReader version 3.0 software. The I-Smart program provided with the Packard PlateReader was used to calculate the protein concentration.

NF-κB Assay

The TransAM NFkB Chemi kit (Active Motiff) was used to detect nondegraded NF-κB p50 in the U937 cells. Instructions of the supplier were followed with no modification. A Bio-tek Instruments ELISA plate reader was used to record optical density at 405 nm. NF-κB was quantified and tabulated as $mOD_{405}$ units.

Statistical Analysis

Means of four to eight replicates per treatment and 95% confidence intervals were computed using standard statistical formula in Excels spreadsheets (Microsoft, Redmond, Wash.).

Results

After 24 hr of stimulation with the cytokine cocktail, the amount of nondegraded NF-κB in the U937 cells would be expected to decrease. As shown in Table 16, controls (330 mOD units) and VD3 treatments contained approximately twice the amount of NF-κB as those cells stimulated with the cytokine cocktail or VD3 plus cytokine cocktail. The addition of RIAA, however, prevented the activation and subsequent degradation of NF-κB (281 vs 122 mOD units). This was a novel and unexpected finding. The lack of activation of NF-κB is favorable because NF-κB activation overrides the apoptotic response to TNF and Fas and can cause a variety of disorders. Also shown in Table 16, with RIAA alone, there was no activation of the NF-κB complex. Therefore, hops components or modified hops components, such as RIAA, can serve to affect disorders associated with NF-κB activation since these components either do not activate NF-κB or prevent activation of NF-κB.

TABLE 16

| Treatment | NF-κB mOD units]† |
|---|---|
| Control (Dimethylsulfoxide solvent controls) | 330 |
| Vitamin D3 (100 nM) | 391 (261-420) |
| IL-1β/γ-interferon/TNFα(25/150/20 ng/mL) | 167 (110-224) |
| VD3 plus IL-1β/γ-interferon/TNFα | 122 (79-165) |
| Reduced isomerized alpha-acids (RIAA) 10 μg/mL) | 362 (301-422) |
| RIAA/VD3/IL-1β/γ-interferon/TNFα | 281 (241-321) |

†Parenthetic values are 95% confidence intervals.

In conclusion, it would be useful to identify a natural formulation of compounds that would to modulate NF-κB. Such a formulation has widespread applications. It would also be useful to identify a natural formulation of compounds that would inhibit expression of COX-2, inhibit prostaglandin synthesis selectively in target cells, or inhibit inflammation response selectively in target cells.

Example 25

Lack of Direct $PGE_2$ Inhibition by Reduced Isomerized Alpha Acids or Isomerized Alpha Acids in LPS-Stimulated RAW 264.7 Cells This example describes testing of post COX-2 (cyclooxygenase-2) induction with A23187 arachidonic acid release.

The objective of this study was to assess the ability of the hops derivatives RIAA (reduced isomerized alpha acids) (Redihop (rho-iso-alpha acids (RIAA), 29.5-30.5%, <0.2% iso-alpha acids) and IAA (isomerized alpha acids) (Isohop; iso-alpha acids (IAA), 29.5-30.5%) to function independently as direct inhibitors of COX-2 mediated $PGE_2$ biosynthesis in the RAW 264.7 cell model of inflammation.

The following methods and procedures were used. Cell culture and treatment with test material—RAW 264.7 cells (ATCC number TIB-71) were obtained from the American Type Culture Collection (Manassas, Va.) and sub-cultured according to the instructions of the supplier. In preparation for testing, cells were grown in growth Dulbecco's Modification of Eagle's medium (DMEM) with 10% fetal bovine serum, heat inactivated (FBS-HI) with penicillin/streptomycin and maintained in log phase prior to experimental setup. On day two of the experiment, cells were plated at $8 \times 10^4$ cells per well in a 96-well tissue culture plate with 200 μL growth medium per well.

Following overnight incubation at 37° C. with 5% $CO_2$, the growth medium was aspirated and replaced with 200 μL DMEM with no FBS or penicillin/streptomycin. RAW 264.7 cells were stimulated with lipopolysaccharide (LPS) (10 ng/ml final concentration) and incubated overnight to induce COX-2 expression. Eighteen hours post LPS-stimulation, test material was added followed 60 minutes later by the addition of A23187. Test materials were dissolved in dimethylsulfoxide (DMSO) as a 250-fold stock solution. Four μL of this 250-fold stock test material preparation was added to 1 mL of DMEM, and 200 μL of this solution was added to eight wells for each dose of test material. Supernatant media was sampled for prostaglandin $E_2$ ($PGE_2$) determination after 30 minutes. Median inhibitory concentrations were computed from a minimum of four concentrations over two independent experiments. The combination indeces (CIs) were computed as described below in statistical methods.

Table 17 describes the test materials used in each of two independent assays that were performed.

TABLE 17

Dosing matrix for LPS-stimulated RAW 264.7 cells followed by treatment with test material TESTING FOR DIRECT COX-2 INHIBITING ACTIVITY
PGE2 assay using undiluted and 1:20 dilution - 2 plates
9.08.03-RAW 264.7 cells treated with LPS, incubated overnight then treated with test material for 60 min followed by A23187 for 30 min

| Compound | Fraction RIAA | C3 [μg/mL] | C4 [μg/mL] | C5 [μg/mL] | C6 [μg/mL] | No. Wells |
|---|---|---|---|---|---|---|
| 1. Beta Tech RIAA | 1.00 | 100 | 10 | 1.0 | 0.10 | 8 |

| Compound | Fraction IAA | C7 [μg/mL] | C8 [μg/mL] | C9 [μg/mL] | C10 [μg/mL] | No. Wells |
|---|---|---|---|---|---|---|
| 2. Beta Tech IAA | 1.00 | 100 | 10 | 1.0 | 0.10 | 8 |
| C11 Aspirin | 1.00 | 10 | 1.0 | 0.10 | 0.010 | 8 |
| C12 APHS | | 10 | 1.0 | 0.10 | 0.010 | 8 |

Determination of $PGE_2$

A commercial, non-radioactive procedure for quantification of $PGE_2$ was employed (Caymen Chemical, Ann Arbor, Mich.) for the determination of $PGE_2$ and the recommended procedure of the manufacturer was used without modification. In summary, 50 μL of the supernatant culture medium were diluted with appropriate amounts of acetylcholinesterase-labeled tracer and $PGE_2$ antiserum, and incubated at room temperature for 18 h. Afterwards, the wells in the $PGE_2$-assay microtiter plate were emptied and rinsed with wash buffer; two-hundred μL of Ellman's reagent containing substrate for acetylcholinesterase were then added. The reaction was maintained on a slow shaker at room temperature for 1 h and the absorbance at 415 nm was determined in a Bio-tek Instruments (Model #Elx800, Winooski, Vt.) enzyme-linked immunosorbant assay (ELISA) plate reader. The manufacturer's specifications for this assay include an intra-assay coefficient of variation of <10%, cross reactivity with $PGD_2$ and $PGF_2$ of less than 1% and linearity over the range of 10-1000 pg mL$^{-1}$. The $PGE_2$ concentration was computed as pg $PGE_2$ per $10^5$ cells.

Cell Viability

Cell viability was assessed by microscopic inspection of cells prior to or immediately following sampling of the medium for $PGE_2$ assay. Cell mortality was noted when observed.

The following materials were used and obtained by the indicated manufacturers. Bacterial lipopolysaccharide (LPS; B E. coli 055:B5) was from Sigma (St. Louis, Mo.). Prostaglandin $E_2$ monoclonal antibody kit was purchased from Cayman Chemical (Ann Arbor, Mich.). Heat inactivated Fetal Bovine Serum (FBS-HI Cat. #35-011CV) and Dulbecco's Modification of Eagle's Medium (DMEM Cat #10-1013CV) was purchased from Mediatech (Herndon, Va.). Unless otherwise noted, all standard reagents were obtained from Sigma (St. Louis, Mo.) and were the purest commercially available. Test substances included RIAA and IAA obtained from Betatech Hops Products (Washington, D.C.).

The following statistical methods were used. A minimum of four concentrations (Table 1) was used to compute dose-response curves and medium inhibitory concentrations ($IC_{50s}$) for $PGE_2$ with 95% confidence intervals using CalcuSyn (BIOSOFT, Ferguson, Mo.). This statistical package performs multiple drug dose-effect calculations using the Median Effect methods described by T-C Chou and P. Talaly, Quantitative analysis of dose-effect relationships: the combined effects of multiple drugs or enzyme inhibitors. Adv Enzyme Regul 22, 27-55 (1984). Briefly, the analysis correlates the "Dose" and the "Effect" in the simplest possible form: $fa/fu=(C/C_m)^m$, where C is the concentration or dose of the compound and Cm is the median-effective dose signifying the potency. Cm is determined from the x-intercept of the median-effect plot. The fraction affected by the concentration of the test material is fa and the fraction unaffected by the concentration is fu (fu=1−fa). The exponent m is the parameter signifying the sigmoidicity or shape of the dose-effect curve. It is estimated by the slope of the median-effect plot.

The median-effect plot is a graph of x=log(C) vs. y=log(fa/fu) and is based on the logarithmic form of Chou's median-effect equation. The goodness of fit for the data to the median-effect equation is represented by the linear correlation coefficient r of the median-effect plot. Usually, the experimental data from enzyme or receptor systems have an r>0.96, from tissue culture an r>0.90 and from animal systems an r>0.85. In the cell-based studies reported here, all linear correlation coefficients were greater than 0.90. For most robust results, experiments are repeated a minimum of three times on three different dates. The percent inhibition at each dose is averaged over the three independent experiments and used to calculate the median inhibitory concentrations reported.

Synergy of test components is quantified using the combination index (CI) parameter. The CI of Chou-Talaly is based on the multiple drug-effect and is derived from enzyme kinetic models (Chou, T.-C. and Talalay, P. A simple generalized equation for the analysis of multiple inhibitions of Michaelis-Menten kinetic systems. J. Biol. Chem. 252:6438-6442 (1977). The equation determines only the additive effect rather than synergism or antagonism. However, synergism is defined in this case as a more than expected additive effect, and antagonism as a less than expected additive effect as proposed by Cho and Talalay. Using the designation of CI=1 as the additive effect, the following relationships were obtained for mutually exclusive compounds that have the same mode of action or for mutually non-exclusive drugs that have totally independent modes of action: CI<1, =1, and >1 indicating synergism, additivity and antagonism, respectively.

Two data transformations were applied where warranted. The first transformation consisted of computing the percent inhibition from the highest $PGE_2$ production produced from the lowest test concentration when the $PGE_2$ production of these low doses exceeded the $PGE_2$ production of the LPS-stimulated control. This process controls for response variability and gradients throughout the plate. The second data transformation adjusted for variance in response at the graded doses. Monte Carlo simulations using the historical variance between wells predicted that dose-response curves appear graded only 40% of the time when duplicate wells per concentration are used in a four-point dose-response curve. Thus, sorting the response by concentration before calculating the $IC_{50}$ was done in those situations in which the response did not appear graded.

Using the protocol outlined above, LPS-stimulation of $PGE_2$ production in RAW 264.7 cells ranged from 1.4-fold to 2.1-fold relative to non-stimulated cells and was somewhat dependent upon dilution of media for the $PGE_2$ assay. The $IC_{50}$ value of 8.7 µg/mL (95% CL (confidence limit)=3.9-19) computed for the aspirin positive control was consistent with published values for direct COX-2 inhibition ranging from 1.4 to 50 µg/mL (Mitchell, J. A. et al. Selectivity of nonsteroidal anti-inflammatory drugs as inhibitors of constitutive and inducible cyclooxygenase. Proc. Natl. Acad. Sci. USA 90:11693-11697 (1994); Warner, T. D. et al. Nonsteroidal drug selectivities for cyclo-oxygenase-1 rather than cyclo-oxygenase-2 are associated with human gastrointestinal toxicity: A full in vitro analysis. Proc. Natl. Acad. Sci. USA 96:7563-7568 (1999), and previous results of 3.2 µg/mL (95% CL=0.55-19) in the A549 cell line.

Figure 10:
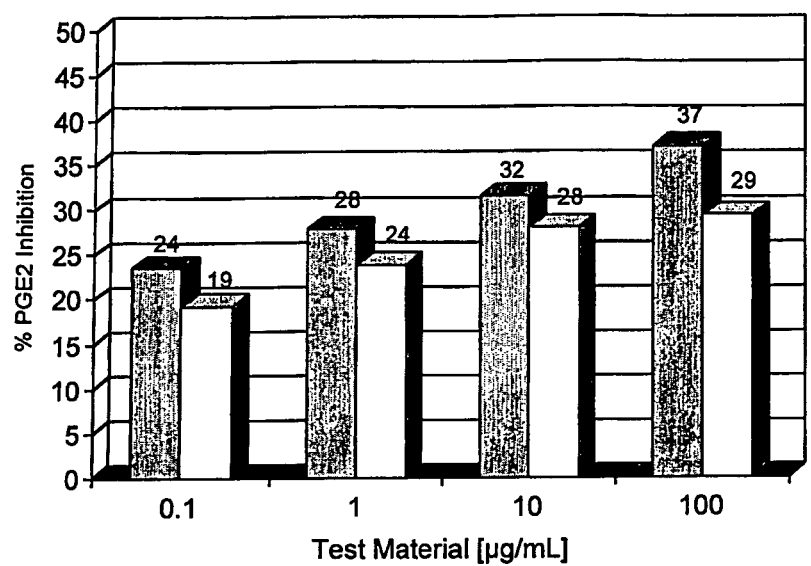
FIG. 10 shows dose-related inhibition of $PGE_2$ biosynthesis for RIAA (shaded bar) and IAA (white bar) treated RAW 264.7 cells following overnight. LPS-stimulation prior to the addition of test material.

RAW 264.7 cells were stimulated with LPS and incubated overnight to induce COX-2 expression (FIG. 10). Eighteen hours post LPS-stimulation, test material was added followed 60 minutes later by the addition of A23187. Supernatant media was sampled for $PGE_2$ determination after 30 minutes. Mean percent $PGE_2$ inhibition values were computed from a minimum of eight replicates over four concentrations and two independent experiments (FIG. 10).

Both RIAA and IAA produced modest, dose-related inhibition of $PGE_2$ in LPS-stimulated RAW 264.7 cells (FIG. 10). Over the 1000-fold increase in concentration of test material, only a 14 and 10 percent increase in inhibition was noted, respectively, for RIAA and IAA. The shallowness of the dose-response slopes resulted in $IC_{50}$ values (Table 18) in the mg/mL range for RIAA (36 mg/mL) and IAA (>1000 mg/mL). Such minimal change in response over three-log units of doses implies that the observed inhibitory effect of the hops derivatives in this cell-based assay is likely a secondary effect on the cells and not direct inhibition of COX. One possible explanation is that the hops derivatives interfere with A23187-mediated arachidonic acid release from cellular membranes.

RAW 264.7 cells were stimulated with LPS and incubated overnight to induce COX-2 expression. Eighteen hours post LPS-stimulation, test material was added followed 60 minutes later by the addition of A23187. Supernatant media was sampled for $PGE_2$ determination after 30 minutes. Median inhibitory concentrations were computed from a minimum of eight replicates at four concentrations over two independent experiments (Table 18).

TABLE 18

Median inhibitory concentrations for RIAA, IAA in RAW 264.7 cells when test material is added post overnight LPS-stimulation.

| Test Material | $IC_{50}$ [mg/mL] | 95% Confidence Interval [mg/mL] |
|---|---|---|
| RIAA | 36 | 17-79 |
| IAA | >1000 | — |

| Positive Control | $IC_{50}$ [µg/mL] | 95% Confidence Interval [µg/mL] |
|---|---|---|
| Aspirin | 8.7 µg/mL | 3.9-19 |

The results of testing RIAA and IAA for their ability to directly inhibit $PGE_2$ biosynthesis from COX-2 produced only a modest, dose-related inhibition of $PGE_2$ in LPS-stimulated RAW 264.7 cells. The shallowness of the dose-response slopes resulted in $IC_{50}$ values in the mg/mL range for RIAA (36 mg/mL) and IAA (>1000 mg/mL). The observed inhibitory effect of the hops derivatives in this cell-based assay is likely a secondary effect on the cells and not direct inhibition of COX. One possible explanation is that the hops derivatives interfere with A23187-mediated arachidonic acid release from cellular membranes.

Example 26

Analysis of Hops Activity in a Cell-Free COX Assay System

This example describes the effect of hops on COX enzyme activity.

The effect of hops on COX enzyme activity was tested in a cell-free COX assay system. The assay was performed using the Cayman Chemical COX Inhibitor Screening Assay kit (Catalog #560131; Cayman Chemical Co.; Ann Arbor Mich.). Briefly, enzyme was pre-incubated with inhibitor for ten minutes at 37° C., then the reaction was initiated with the addition of arachidonic acid. After two minutes, the reaction was stopped by the addition of HCl. The $PGH_2$ was reduced to $PGH_2$ alpha, which was then quantified using a competitive enzyme immunoassay (EIA). Each concentration was tested with two separate reactions, which were then each tested in duplicate during the EIA step.

The results of the COX enzyme assay are shown in Table 19. As can be seen, IAA and RIAA had essentially no effect on COX-1 or COX-2 enzyme activity. In contrast, the COX inhibitor indomethacin inhibited both COX-1 and COX-2.

TABLE 19

IAA and RIAA inhibition of COX acitivity.

| COX 1 ug/ml | Indomethacin % Inhibition | COX 1 ug/ml | IAA % Inhibition | COX 1 ug/ml | RIAA % Inhibition |
|---|---|---|---|---|---|
| 10 | 60.6 | 200 | 9.6 | 200 | 2.9 |
| 1 | 34.6 | 100 | 3 | 100 | 0.5 |
| 0.01 | 28.2 | 10 | 4.2 | 10 | 2.5 |
| 0.001 | −2.8 | 1 | 2.1 | 1 | 1.9 |

| COX 2 ug/ml | % Inhibition | COX 2 ug/ml | % Inhibition | COX 2 ug/ml | % Inhibition |
|---|---|---|---|---|---|
| 200 | 48.4 | 200 | 0.3 | 200 | 1.9 |
| 50 | 77.6 | 100 | −3.6 | 100 | −0.7 |
| 0.5 | 67.5 | 10 | −2 | 10 | 2.7 |
| 0.05 | 3.4 | 1 | 0.9 | 1 | 2.8 |

These results demonstrate that hops have no significant COX enzyme activity. Therefore, hops likely acts at the level of expression of COX-2.

Example 27

Gastric Mucosal Cell Model for Estimating Relative Gastrointestinal Toxicity of NSAIDs This example describes the use of a gastric mucosal cell line (AGS cells) for determining potential gastrointestinal toxicity of non-steroidal anti-inflammatory drugs.

As described in Examples 1 and 2, AGS cells provide a model system for determining potential gastrointestinal toxicity. The objective of this study was to further characterize the AGS human gastric mucosal cell line as a model for estimating relative GI toxicity (gastropathy) of COX-inhibiting compounds.

AGS cells were further characterized as a model for gastrointestinal toxicity essentially as described in Example 2. Briefly, chemicals used in the assays were obtained as follows. Commercial formulations of rofecoxib tablets and celecoxib capsules were used. $PGE_2$ EIA kits were obtained from Cayman Chemical (Ann Arbor, Mich.). Anti-COX-1 and anti-COX-2 rabbit polyclonal antisera were obtained from Upstate Biotechnology (Waltham, Mass.), and donkey anti-goat IgG-HRP was procured from Santa Cruz Biotechnology (Santa Cruz, Calif.). Heat Inactivated Fetal Bovine Serum (FBS-HI Cat. #35-011CV) and Dulbecco's Modification of Eagle's Medium (DMEM Cat #10-013CV) was purchased from Mediatech (Herndon, Va.). Interleukin-1β (IL-1β) and all standard chemicals and non-steroidal anti-inflammatory drugs (NSAIDs), unless noted, were obtained from Sigma (St Louis, Mo.) and were of the highest purity commercially available.

For cell culture, human airway epithelial cells A549 were obtained from the American Type Culture Collection (Manassas, Va.) and sub-cultured according to the instructions of the supplier. The cells were routinely cultured at 37° C. with 5% $CO_2$ in RPMI 1640 containing 10% FBS with 50 units penicillin/mL, 50 µg streptomycin/mL, 5% sodium pyruvate, and 5% L-glutamine. For treatment of the cells with test compounds, the William Harvey Modified Assay (WHMA) was used for determination of COX-2 inhibition with no modifications [Warner T D, Giuliano F, Vojnovic I, Bukasa A, Mitchell J A, Vane J R. (1999) Non-steroidal drug selectivities for cyclooxygenase-1 rather than cyclooxygensase-2 are associated with human gastrointestinal toxicity: A full in vitro analysis. Proc. Natl. Acad. Sci. USA. 96:7563-7568]. Briefly, A549 cells were exposed to IL-1β for 24 h, media was removed and human plasma (100 µL) was added together with test agents or the DMSO vehicle. For initial experiments, test agent concentrations were 25, 5, 0.5, and 0.05 µg/mL. DMSO in each microtiter well was less than 1% of the 200 µL volume; 60 min later, A23187 (50 µM) was added; after 30 min, 50 µL of the culture supernatant media was sampled and immediately assayed for $PGE_2$ as detailed elsewhere. The AGS human gastric mucosal cell line (American Type Culture Collection, Manassas, Va.) was also cultured and maintained according to recommended ATCC methodology. Sub-cultured AGS cells were grown in IMDM with 20% FBS with 50 units penicillin/mL and 50 µg streptomycin/mL; cells were maintained in log phase prior to each experiment. For $PGE_2$ assays, approximately $10^5$ cells per well were plated into 96-well plates in 200 µL growth medium per well. Cells were grown to 80% confluence and washed 3-times with IMDA media prior to addition of test agent. NSAIDs were added in 200 µL of IMDA media containing no FBS or penicillin/streptomycin. Sixty minutes following addition of the test materials, arachidonic acid (AA) was either induced with addition of the calcium ionophore A23187, or exogenously added at 100 or 5 µM AA in DMSO. Incubation at 37° C. was carried out for an additional 30 min. Fifty microliters of media were sampled for $PGE_2$ determination.

For determination of $PGE_2$, a commercial, non-radioactive procedure for quantification of $PGE_2$ was employed (Cayman Chemical, Ann Arbor, Mich.) for the determination of $PGE_2$ and the recommended procedure of the manufacturer was used without modification. Briefly, 50 µL of the supernatant culture medium, along with a serial dilution of $PGE_2$ standard samples, were mixed with appropriate amounts of acetylcholinesterase-labeled tracer and PGE$_2$ antiserum and incubated at room temperature for 18 h. Afterwards, the wells in the PGE$_2$-assay microtiter plate were emptied and rinsed with wash buffer, and 200 µL of Ellman's reagent containing substrate for acetylcholinesterase were then added. The reaction was performed on a slow shaker at room temperature for 1 h, after which absorbance at 415 nm was determined in a Bio-Tek Instrument ELISA plate reader (Model #Elx800, Winooski, Vt.). The manufacturer's specifications for this assay include an intra-assay coefficient of variation of <10%, cross reactivity with PGD$_2$ and PGF$_{2\alpha}$ of less than 1%, and linearity over the range of 10-1000 pg/mL. The PGE$_2$ concentration was recorded as pg PGE$_2$ per $10^5$ cells.

For assay calculations, a minimum of four concentrations each, with two replicates per concentration over three independent experiments, were used to compute median inhibitory concentrations (IC$_{50}$) and their 95% confidence limits for the inhibition of PGE$_2$ biosynthesis (CalcuSyn, BIOSOFT, Ferguson, Mo.). Complete dose-response curves with coefficients of determination >0.9 were obtained for all test compounds, except salicylic acid and acetaminophen for A549 and AGS cells and diisopropylfluorophosphate for AGS cells with 100 µM AA. The therapeutic index (TI) for gastrointestinal safety was computed as the log (AGS IC$_{50}$/A549 IC$_{50}$). While it has been recommended that the IC$_{80}$ should be used for the efficacy component (i.e., inhibition of PGE$_2$ synthesis in A549 cells) in the calculation of the TI, large errors are associated with estimates at the extremes of the dose-response curve. Thus, there exists greater uncertainty in ratios in which these estimates are used. Positive TI indicate low potential for GI toxicity, while negative TI indicate a higher potential for GI toxicity. Spearman's rank correlation coefficient $r_s$ was computed to quantify the degree of association between ranking of previously published TI using non-target cells and the AGS/A549 model. The parameter $r_s$ was also used to determine the degree of association between in vitro ranking of TI and ranking of clinically assessed NSAID gastropathy. The probability of a Type I error was set at the nominal 5% level.

The AGS human gastric cell line was cultured in six-well plates at 37° C. with 5% CO2 in a humidified incubator for 24 h. Cells were lysed on ice in lysis buffer and protein concentration determined. Fifty micrograms of cell lysate were solubilized and fractionated on a 10% polyacrylamide gel containing sodium dodecylsulfate. For immunoblotting, Western blotting of COX-1 and COX-2 was performed using PAGEr™ Gold Precast Gels (Bio Whittaker Molecular Applications, Rockland, Me.). RAW 264.7 cell lysates containing approximately 60 µg protein were loaded with laemmli sample buffer into the wells in a total volume of 30 µL. The vertical minigel electrophoresis chambers used were made by Savant Instruments, Inc. (Model MV 120; Holbrook, N.Y.). Gels were run at 40 mA/plate (constant current) at room temperature until the bromophenol blue stain reached the bottom of the gel, which took about 1 h. Gels were then blotted on polyvinyl fluoride transfer membranes (PVDF) (Pall Corporation, Ann Arbor, Mich.), overnight, at 500 mA and 4° C. Molecular weight markers used were the unstained, broad-range Precision Protein Standards (Bio Rad, Hercules, Calif.). The BioWest™ extended duration chemiluminescent substrate (BioImaging Systems, Upland, Calif.), a non-isotopic, horseradish peroxidase substrate kit for Western Blot detection, was used for protein visualization. Images of Western Blots were acquired using a UVP Epi Chemi II Darkroom (BioImaging Systems), and were analyzed and enhanced by LabWorks™ Image Acquisition and Analysis Software (Bio-Imaging Systems). Band intensities were evaluated through densitometric analysis, computed using ScanAnalysis® software (BIOSOFT, Ferguson, Mo.), and recorded as arbitrary Density Units (DU).

The AGS cell line constitutively expressed both COX-1 and COX-2, with COX-1 expression approximately 4 times greater than COX-2 expression (see Example 1). These results are in agreement with recently published work (Fan et al., Interleukin-1beta induces cyclo-oxygenase-2 expression in gastric cancer cells by the p38 and p44/42 mitogen-activated protein kinase signaling pathways. J Gastroenterol Hepatol. 16:1098-104 (2001)) using the AGS cell line, in which constitutive expression of both cyclooxygenase enzymes was demonstrated.

Table 20 shows the median inhibitory concentration (IC50) for PGE2 biosynthesis of select NSAID in the A549 and AGS cell model.

TABLE 20

Median inhibitory concentrations (IC$_{50}$) for PGE$_2$ $_{biosynthesis\ of}$ select NSAID in the A549 and AGS cell model.†

| | | AGS Gastric Mucosal Cells | | |
|---|---|---|---|---|
| Compounds | A549 A23187 [µM] | A23187 [µM] | 100 µM Arachidonate [µM] | 5 µM Arachidonate [µM] |
| DIFP†† | 6.5 (1.5-28) | 359 (125-1022) | >136 | 217 (141-185) |
| Rofecoxib | 0.24 (0.15-0.45) | 5.5 (2.7-11) | 12 (2.3-64) | 21 (5.8-79) |
| Celecoxib | 0.21 (0.01-4.2) | 0.063 (0.02-0.22) | 17 (2.5-113) | 9.4 (3.9-23) |
| Nimensulide | 0.32 (0.16-0.65) | 0.12 (0.0081-1.7) | 73 (25-211) | 75 (52-104) |
| Naproxen | 28 (1.3-600) | 0.83 (0.24-2.8) | 167 (16-1735) | 313 (91-1039) |
| Ibuprofen | 12 (6.8-19) | 2.8 (1.3-5.8) | 6.3 (1.4-29) | 107 (38-291) |
| Aspirin | 18 (3.0-106) | 2.9 (1.4-5.6) | 6.0 (2.9-12) | 18 (9.4-37) |
| Salicylic acid | 4246 (355-50971) | 1065 (94-12217) | 112 (69-181) | 7848 (1775-34565) |
| Acetaminophen | 238 (6.62-9589) | 535 (179-1616) | 346 (192-609) | 3815 (1152-12649) |

TABLE 20-continued

Median inhibitory concentrations (IC$_{50}$) for PGE$_2$ biosynthesis of select NSAID in the A549 and AGS cell model.†

| | | AGS Gastric Mucosal Cells | | |
|---|---|---|---|---|
| Compounds | A549 A23187 [μM] | A23187 [μM] | 100 μM Arachidonate [μM] | 5 μM Arachidonate [μM] |
| Indomethacin | 8.1 (2.6-26) | 0.0042 (0.00042-0.039) | 0.0025 (0.000028-0.20) | 0.0056 (0.002-0.011) |

†Parenthetic values are 95% confidence intervals of the IC$_{50}$ estimate.
††DIFP = diisofluorophosphate.

Figure 11:
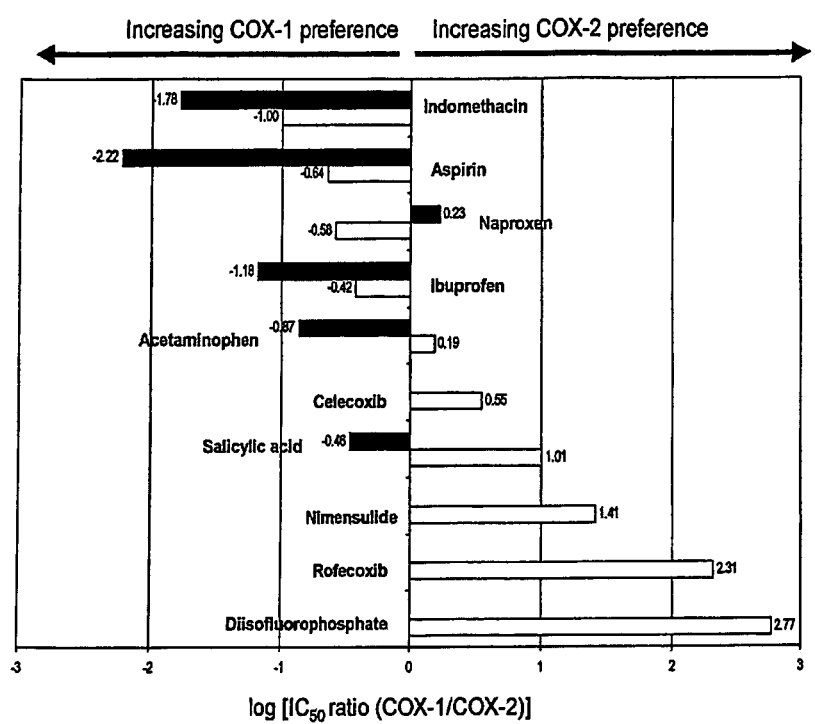
FIG. 11 shows comparison of log $IC_{50}$ ratios and ranking of potential gastropathy. Log $IC_{50}$ ratios using the William Harvey Modified Assay (WHMA) are expressed WHMA COX-1/WHMA COX-2 from Warner, et al. (white bars) and Mitchell, et al. (dark bars) are shown in [A] with log $IC_{50}$ ratios (AGS/WHMA COX-2) for AGS cells treated with A23187 [B], 100 μM arachidonic acid [C], or 5 μM arachidonic acid [D]. Values to the right of 0 indicate decreasing probability of gastropathy, whereas values to the left of 0 indicate increasing probability of gastropathy.
Figure 11:
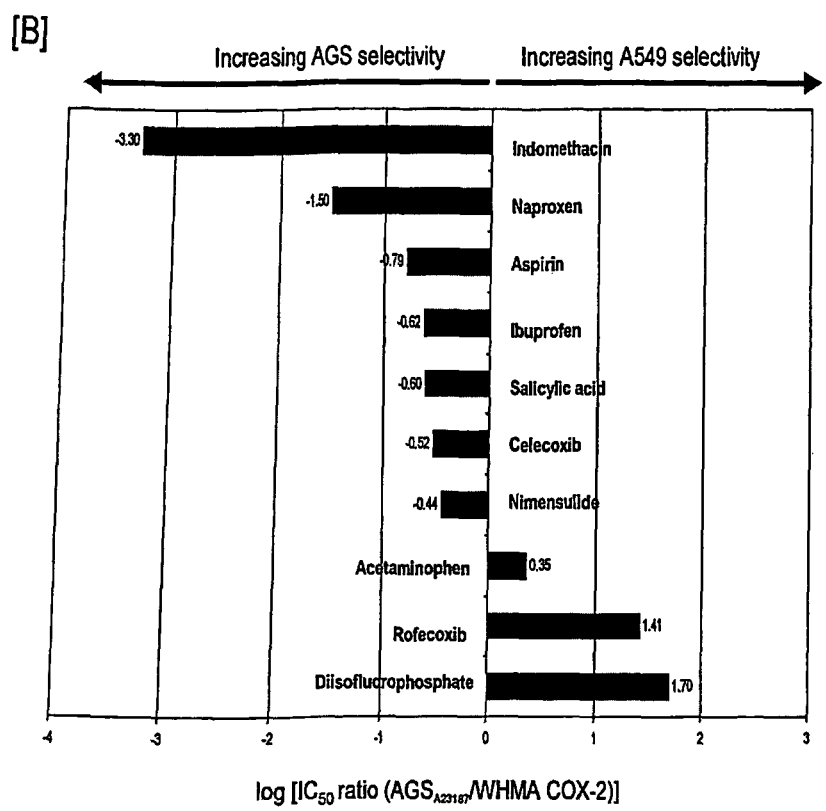
Figure 11:
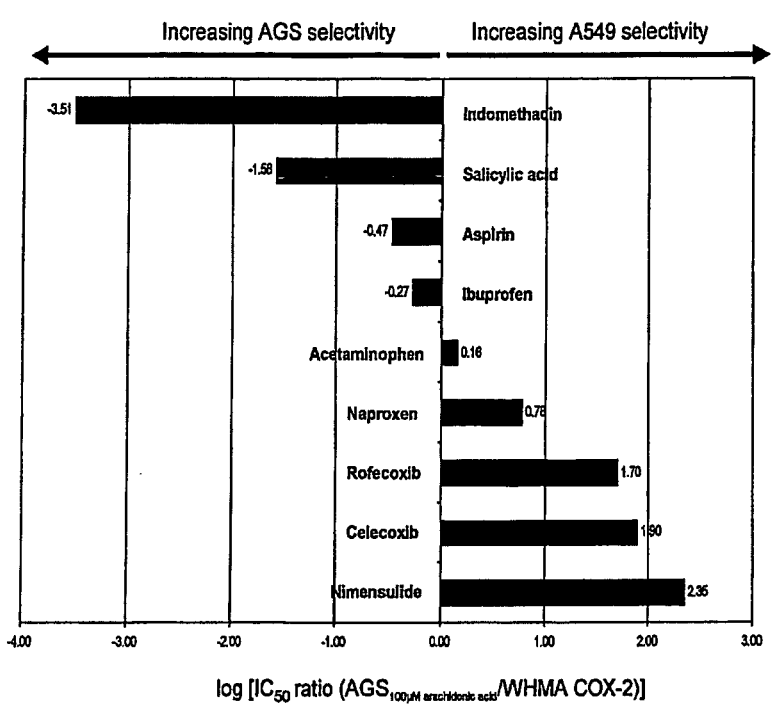
Figure 11:
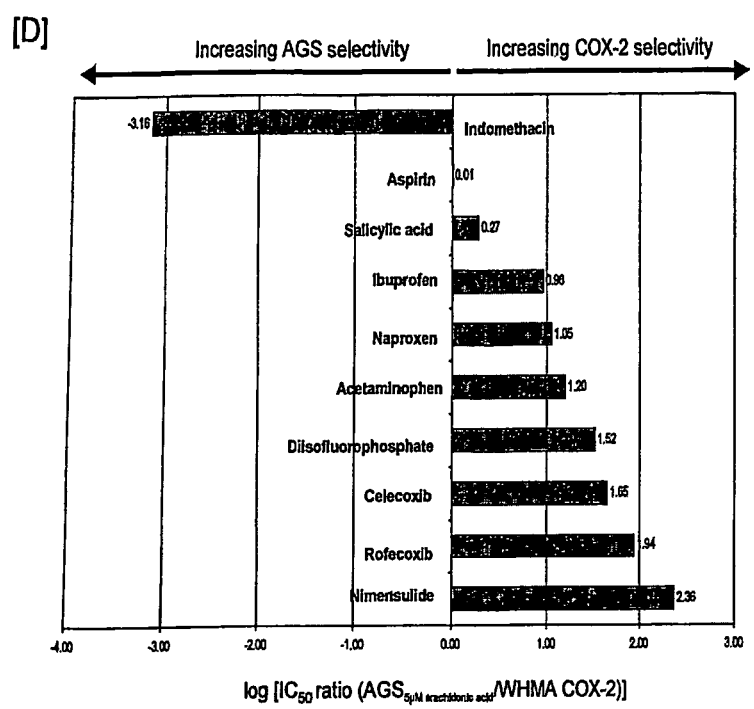

FIG. 11 shows a comparison of Log IC$_{50}$ ratios and ranking of potential gastropathy. Log IC$_{50}$ ratios using the William Harvey Modified Assay (WHMA) are expressed WHMA COX-1/WHMA COX-2 from Warner, et al. (Nonsteroidal drug selectivities for cyclo-oxygenase-1 rather than cyclo-oxygensase-2 are associated with human gastrointestinal toxicity: A full in vitro analysis. Proc. Natl. Acad. Sci. USA. 96:7563-7568(1999))(white bars) and Mitchell, et al. (Selectivity of nonsteroidal antiinflammatory drugs as inhibitors of constitutive and inducible cyclooxygenase. Proc. Natl. Acad. Sci. USA. 90:11693-11697 (1994))(blue bars) are shown in FIG. 11A, with log IC$_{50}$ ratios (AGS/WHMA COX-2) for AGS cells treated with A23187 FIG. 11B), 100 μM arachidonic acid (FIG. 11C), or 5 μM arachidonic acid (FIG. 11D). Values to the right of 0 indicate decreasing probability of gastropathy, whereas values to the left of 0 indicate increasing probability of gastropathy.

As shown in FIG. 11, the relationship between previously published data and the three AGS protocols was examined. The log [IC$_{50}$ ratio (WHMA COX-1/WHMA COX-2)] was computed from published data (FIG. 11A) and compared to the log [IC$_{50}$ ratios (AGS/WHMA COX-2)] for the A23187 (FIG. 11B), 100 μM arachidonic acid (FIG. 11C), and 5 μM arachidonic acid (FIG. 11D) protocols. Ranking of compounds from lowest to greatest GI toxicity potential was strikingly similar among the models and within AGS protocols. Interestingly, only rofecoxib and indomethacin showed the least and most potential GI toxicity, respectively, in all AGS protocols. Rank estimates of TI were similar to rank TI computed using platelets (COX-1) and A549 cells (COX-2) with $r_s$=0.903, p<0.01 for A23187; 0.733, p=0.02 for 100 μM AA; and 0.77, p<0.02 for 5 μM AA. Quantitatively, however, the AGS/A549 model exhibited lower TI than the platelet/A549 model. A23187-mediated AA release, 100 μM AA addition, and 5 μM AA addition provided rank estimates of GI toxicity significantly associated with clinical rankings of NSAID gastropathy, respectively ($r_s$=0.933, p<0.01; 0.783, p<0.01; 0.683, p=0.05). A23187 ranking of NSAIDs from lowest to greatest potential for GI toxicity was rofecoxib<acetaminophen<nimensulide<celecoxib<salicylic acid<ibuprofen<aspirin<naproxen<indomethacin.

As described in Example 1 and as seen in normal gastric mucosal cells, the AGS cell line constitutively expresses both COX-1 and COX-2. The use of AGS and A549 cells provided rank estimates of TI that were qualitatively similar to rank TI computed using platelets (COX-1) and A549 cells with $r_s$=0.903, p<0.01 for A23187; 0.733, p=0.02 for 100 μM AA; and 0.770, p<0.02 for 5 μM AA. Quantitatively, the AGS/A549 model exhibited lower TI than the platelet/A549 model. A23187-mediated AA release, as well as the 100 μM and 5 μM AA-addition protocols provided rank estimates of GI toxicity significantly associated with clinical rankings of NSAID gastropathy, at $r_s$=0.933, p<0.01; 0.783, p<0.01; and 0.683, p=0.05, respectively. A23187 ranking of NSAIDs from lowest to greatest potential for GI toxicity was rofecoxib<acetaminophen<nimensulide<celecoxib<salicylic acid<ibuprofen<aspirin<naproxen<indomethacin.

These results further demonstrate that the AGS human gastric mucosal cell line can serve as a model for assessing the gastrointestinal effects of COX-inhibiting compounds. The AGS derived data indicate that inhibition of gastric PGE$_2$ biosynthesis underlies the human gastropathy of NSAIDs.

A preferred embodiment comprises compositions containing at least one fraction isolated or derived from hops (*Humulus lupulus*). Examples of fractions isolated or derived from hops are alpha acids, isoalpha acids, reduced isoalpha acids, tetra-hydroisoalpha acids, hexa-hydroisoalpha acids, beta acids, and spent hops. Preferred compounds of fractions isolated or derived from hops, include, but are not limited to, humulone, cohumulone, adhumulone, isohumulone, isocohumulone, isoadhumulone, dihydro-isohumulone, dihydro-isocohumulone, dihydro-adhumulone, tetrahydro-isohumulone, tetrahydro-isocohumulone, tetrahydro-adhumulone, hexahydro-isohumulone, hexahydro-isocohumulone, and hexahydro-adhumulone. Preferred compounds can also bear substituents, such as halogens, ethers, and esters.

Another embodiment comprises composition containing tryptantin and conjugates thereof.

Other embodiments relate to combinations of components. One embodiment relates to compositions that include, as a first component, an active ingredient isolated or derived from an extract of hops and as a second component at least one member selected from the group consisting of rosemary (*Rosmarinus officinalis* L.), an extract or compound derived from rosemary, a triterpene species or derivatives or conjugates thereof, and tryptanthrin or conjugates thereof. Another embodiment relates to compositions that include, as a first component, tryptanthrin or conjugates thereof and as a second component at least one member selected from the group consisting of an active ingredient isolated or derived from an extract of hops, rosemary, an extract or compound derived from rosemary, and a triterpene species or derivatives or conjugates thereof.

It will be readily apparent to those skilled in the art that various changes and modifications of an obvious nature may be made without departing from the spirit of the invention, and all such changes and modifications are considered to fall within the scope of the invention as defined by the appended claims. Such changes and modifications would include, but not be limited to, the incipient ingredients added to affect the capsule, tablet, lotion, food or bar manufacturing process as well as vitamins, herbs, flavorings and carriers. Other such changes or modifications would include the use of other herbs or botanical products containing the combinations of the preferred embodiments disclosed above. Many additional modifications and variations of the embodiments described herein may be made without departing from the scope, as is apparent to those skilled in the art. The specific embodiments described herein are offered by way of example only.

What is claimed is:

1. An anti-inflammatory composition comprising anti-inflammatory effective amounts of a first component selected from the group consisting of dihydro-isohumulone, dihydro-isocohumulone, dihydro-isoadhumulone, tetrahydro-isohumulone, tetrahydro-isocohumulone, tetrahydro-isoadhumulone, hexahydro-isohumulone, hexahydro-isocohumulone, and hexahydro-isoadhumulone; and as a second component, at least one member selected from the group consisting of rosemary, an extract derived from rosemary, a compound derived from rosemary, and a triterpene species.

2. The composition of claim 1, wherein the first component is derived from hops.

3. The composition of claim 1, wherein the compound derived from rosemary is selected from the group consisting of 1,8-cineole, 19-alpha-hydroxyursolic acid, 2-β-hydroxyoleanolic acid, 3-O-acetyloleanolic acid, 3-O-acetylursolic acid, 6-methoxy-luteolin-7-glucoside, 6-methoxyluteolin, 6-methoxyluteolin-7-glucoside, methoxyluteolin-7-methyl-ether, 7-ethoxy-rosmanol, 7-methoxy-rosmanol, alpha-amyrin, alpha-humulene, alpha-hydroxyhydrocaffeic acid, alpha-pinene, alpha-terpinene, alpha-terpinenyl acetate, alpha-terpineol, alpha-thujone, apigenin, apigenin-7-glucoside, curcumene, benzyl-alcohol, β-amyrenone, β-amyrin, β-elemene, β-pinene, betulin, betulinic acid, borneol, bornyl-acetate, caffeic acid, camphene, camphor, carnosic acid, carnosol, carvacrol, carvone, caryophyllene, caryophyllene-oxide, chlorogenic acid, diosmetin, gamma-terpinene, hesperidin, isoborneol, limonene, luteolin, luteolin-3'-O-(3"-O-acetyl)-β-D-glucuronide, luteolin-3'-O-(4"-O-acetyl)-β-D-glucuronide, luteolin-3'-O-β-D-glucuronide, luteolin-7-glucoside, methyl-eugenol, myrcene, neo-chlorogenic acid, nepetin, octanoic acid, oleanolic acid, p-cymene, piperitenone, rosmanol, rosmaric acid, rosmaricine, rosmaridiphenol, rosemarinic acid, rosmarinol, rosmariquinone, sabinene, sabinyl acetate, salicylates, salicylic acid-2-β-D-glucoside, squalene, terpinen-4-ol, terpinolene, thymol, trans-anethole, trans-carveol, ursolic acid, verbenone, and zingiberene.

4. The composition of claim 1, wherein the triterpene species is selected from the group consisting of 18-a-glycyrrhetinic acid, 18-β-glycyrrhetinic acid, 2-a-3-a-dihydrooxyurs-12-3n-28-onic acid, 3-a-hydroxyursolic acid, 3-oxo-ursolic acid, betulin, betulinic acid, celastrol, eburicoic acid, friedelin, glycyrrhizin, gypsogenin, oleanolic acid, oleanolic acid-3-acetate, pachymic acid, pinicolic acid, sophoradiol, soyasapogenol A, soyasapogenol B, tripteris, triptophenolide, tumulosic acid, ursolic acid, ursolic acid-3-acetate, uvaol, and β-sitosterol.

5. The composition of claim 1, wherein the composition comprises about 0.5 to 10,000 mg of the first component.

6. The composition of claim 1, wherein the composition comprises about 0.5 to 5,000 mg of the second component, and wherein the second component is selected from the group consisting of rosemary, an extract derived from rosemary, and a compound derived from rosemary.

7. The composition of claim 1, wherein the composition comprises about 0.035 to 3,500 mg of the triterpene species.

8. The composition of claim 1, wherein the composition comprises about 0.001 to 10 weight percent of the first component.

9. The composition of claim 1, wherein the composition comprises about 0.001 to 10 weight percent of the second component.

10. The composition of claim 1, wherein a ratio of the first component to the second component is in the range of about 100:1 to about 1:100.

11. The composition of claim 1, wherein the composition further comprises a pharmaceutically acceptable carrier.

12. The composition of claim 1, further comprising glucosamine.

* * * * *

UNITED STATES PATENT AND TRADEMARK OFFICE
CERTIFICATE OF CORRECTION

PATENT NO. : 8,486,457 B2  
APPLICATION NO. : 10/532388  
DATED : July 16, 2013  
INVENTOR(S) : Matthew L. Tripp et al.

Page 1 of 1

It is certified that error appears in the above-identified patent and that said Letters Patent is hereby corrected as shown below:

ON THE TITLE PAGE, under the heading "Related U.S. Application Data:"

Item (60) should state:

-- This application is the U.S. National Phase under 35 U.S.C. § 371 of International Application No. PCT/US03/33362, filed on October 20, 2003, which claims priority to US Application No. 10/464,410, filed on June 18, 2003 (now US Patent No. 8,142,819), and US Application No. 10/464,834, filed on June 18, 2003 (now abandoned), and US Application No. 10/400,293, filed on March 26, 2003 (now abandoned), and US Application No. 10/401,283, filed on March 26, 2003 (now abandoned), and US Provisional Application No. 60/450,237, filed February 25, 2003 (now expired), and US Provisional Application No. 60/420,383, filed October 21, 2002 (now expired). --

Signed and Sealed this
Twentieth Day of May, 2014

Michelle K. Lee
*Deputy Director of the United States Patent and Trademark Office*